(12) United States Patent
Gadewar et al.

(10) Patent No.: US 10,081,588 B2
(45) Date of Patent: Sep. 25, 2018

(54) PRODUCTION OF BUTYL ACETATE FROM ETHANOL

(71) Applicant: ResCurve, LLC, Santa Barbara, CA (US)

(72) Inventors: Sagar B. Gadewar, Goleta, CA (US); Brian Christopher Vicente, Santa Barbara, CA (US); Peter K. Stoimenov, Goleta, CA (US)

(73) Assignee: ResCurve, LLC, Santa Barbara, CA (US)

( * ) Notice: Subject to any disclaimer, the term of this patent is extended or adjusted under 35 U.S.C. 154(b) by 0 days.

(21) Appl. No.: 15/101,251

(22) PCT Filed: Dec. 3, 2014

(86) PCT No.: PCT/US2014/068439
§ 371 (c)(1),
(2) Date: Jun. 2, 2016

(87) PCT Pub. No.: WO2015/085002
PCT Pub. Date: Jun. 11, 2015

(65) Prior Publication Data
US 2016/0297737 A1    Oct. 13, 2016

Related U.S. Application Data

(60) Provisional application No. 61/911,832, filed on Dec. 4, 2013.

(51) Int. Cl.
| | | |
|---|---|---|
| *C07C 67/03* | (2006.01) | |
| *C07C 29/34* | (2006.01) | |
| *C07C 67/40* | (2006.01) | |
| *B01D 3/00* | (2006.01) | |
| *B01J 8/02* | (2006.01) | |
| *B01J 19/00* | (2006.01) | |
| *C07C 67/54* | (2006.01) | |

(52) U.S. Cl.
CPC .............. *C07C 67/03* (2013.01); *B01D 3/009* (2013.01); *B01J 8/0278* (2013.01); *B01J 19/0046* (2013.01); *C07C 29/34* (2013.01); *C07C 67/40* (2013.01); *C07C 67/54* (2013.01); *B01J 2208/00893* (2013.01); *B01J 2208/025* (2013.01); *B01J 2219/0059* (2013.01); *B01J 2219/0072* (2013.01); *B01J 2219/00759* (2013.01); *Y02P 20/127* (2015.11); *Y02P 20/582* (2015.11)

(58) Field of Classification Search
CPC ..... B01D 3/009; B01J 19/0046; B01J 8/0278; B01J 2208/00893; B01J 2208/025; B01J 2219/0059; B01J 2219/0072; B01J 2219/00759; C07C 29/34; C07C 67/03; C07C 67/40; C07C 67/54; Y02P 20/127; Y02P 20/582
See application file for complete search history.

(56) References Cited

U.S. PATENT DOCUMENTS

| | | | |
|---|---|---|---|
| 1,992,480 | A | 2/1935 | Fuchs et al. |
| 2,525,829 | A | 10/1950 | Royer et al. |
| 2,645,667 | A | 7/1953 | Burgoyne |
| 3,714,236 | A | 1/1973 | Wright, Jr. et al. |
| 4,052,424 | A | 10/1977 | Vanderspurt |
| 4,220,803 | A | 9/1980 | Marcinkowsky et al. |
| 4,379,028 | A | 4/1983 | Berg et al. |
| 4,435,595 | A | 3/1984 | Agreda et al. |
| 4,440,946 | A | 4/1984 | Summerville et al. |
| 4,523,027 | A | 6/1985 | Kummer et al. |
| 4,569,726 | A | 2/1986 | Berg et al. |
| 4,645,570 | A | 2/1987 | Sridhar et al. |
| 4,825,013 | A | 4/1989 | Quarderer et al. |
| 4,996,007 | A | 2/1991 | Chao et al. |
| 5,194,675 | A | 3/1993 | Joerg et al. |
| 5,334,751 | A | 8/1994 | Lemanski et al. |
| 6,407,295 | B1 | 6/2002 | Kaizik et al. |
| 6,632,330 | B1 | 10/2003 | Colley et al. |

(Continued)

FOREIGN PATENT DOCUMENTS

| | | |
|---|---|---|
| BR | 9104652 A | 4/1993 |
| CN | 85105799 A | 11/1986 |

(Continued)

OTHER PUBLICATIONS

Yamamoto et al., "The Direct Conversion of Ethanol to Ethyl and Methyl Acetates Catalyzed by Iridium Complex," Chemistry Letters , vol. 38, No. 11 (2009), pp. 1106-1107. (Year: 2009).*
Marcu et al., "Catalytic valorization of bioethanol over Cu—Mg—Al mixed oxide catalysts," Catalysis Today 147 (2009) 231-238. (Year: 2009).*
Sushkevich, et al., "Mechanistic Study of Ethanol Dehydrogenation over Silica Supported Silver," ChemCatChem 2013, 5, 2367-2373. (Year: 2013).*
Foreign communication from a related application—Extended European Search Report of Application No. 14754744.2 dated Nov. 21, 2016, 10 pages.
Foreign communication from a related application—First Office Action, Chinese Application No. 201480009376.7 dated Jul. 29, 2016, with English translation, 13 pages.
Gines, Marcelo J. L., et al., "Bifunctional Condensation Reactions of Alcohols on Basic Oxides Modified by Copper and Potassium," Journal of Catalysis, 1998, pp. 155-172, vol. 176, Academic Press.
Sharma, M. M., et al., "Industrial Applications of Reactive Distillation, Part I," 2002, 28 pages, Wiley-VHC Verlag GmbH & Co. KGaA.
Tsuchida, Takashi, et al., "Reaction of ethanol over hydroxyapatite affected by Ca/P ratio of catalyst," Journal of Catalysis, 2008, pp. 183-189, vol. 259, Elsevier, Inc.
Filing receipt and specification for international application entitled "Ethyl acetate production," filed Oct. 20, 2010 as International application No. PCT/US2010/002806.
Filing receipt and specification for provisional patent application entitled "Production of butanols and ethyl acetate," by Sagar B. Gadewar, et al., filed Feb. 19, 2013 as U.S. Appl. No. 61/766,484.

(Continued)

*Primary Examiner* — Pancham Bakshi
*Assistant Examiner* — Mark R Luderer
(74) *Attorney, Agent, or Firm* — Conley Rose, P.C.; Andrew M. Metrailer

(57) ABSTRACT

A reactive distillation method comprises introducing a feed stream to a reactive distillation column, wherein the feed stream comprises ethanol, contacting the feed stream with one or more catalysts in the reactive distillation column during a distillation, and removing butyl acetate during the distillation from the reactive distillation column as a bottoms stream. The feed stream reacts in the presence of the one or more catalysts to produce a reaction product comprising ethyl acetate, butanol, and water, wherein the butanol and the ethyl acetate react to produce a reaction product comprising the butyl acetate.

30 Claims, 18 Drawing Sheets

(56) References Cited

U.S. PATENT DOCUMENTS

| | | | |
|---|---|---|---|
| 6,809,217 | B1 | 10/2004 | Colley et al. |
| 7,700,810 | B2 | 4/2010 | Kourtakis et al. |
| 7,700,811 | B2 | 4/2010 | Kourtakis et al. |
| 7,700,812 | B2 | 4/2010 | Kourtakis et al. |
| 7,700,813 | B2 | 4/2010 | Kourtakis et al. |
| 7,705,192 | B2 | 4/2010 | Kourtakis et al. |
| 7,745,672 | B2 | 6/2010 | Kourtakis et al. |
| 8,071,823 | B2 | 12/2011 | Ozer et al. |
| 8,080,684 | B2 | 12/2011 | Hassan et al. |
| 8,080,698 | B2 | 12/2011 | Eng |
| 8,304,587 | B2 | 11/2012 | Warner et al. |
| 8,318,989 | B2 | 11/2012 | Kourtakis et al. |
| 8,558,025 | B2 | 10/2013 | Gadewar |
| 8,562,921 | B2 | 10/2013 | Gadewar |
| 9,018,427 | B2 | 4/2015 | Gadewar et al. |
| 9,079,851 | B2 | 7/2015 | Gadewar et al. |
| 2006/0178524 | A1 | 8/2006 | Zuber et al. |
| 2010/0160693 | A1 | 6/2010 | Kourtakis et al. |
| 2012/0035390 | A1 | 2/2012 | Gadewar |
| 2012/0165577 | A1 | 6/2012 | Fagan et al. |
| 2013/0197266 | A1 | 8/2013 | Gadewar et al. |
| 2014/0012037 | A1 | 1/2014 | Gadewar et al. |

FOREIGN PATENT DOCUMENTS

| | | |
|---|---|---|
| CN | 1255476 A | 6/2000 |
| CN | 101065345 A | 10/2007 |
| EP | 0101910 A1 | 3/1984 |
| EP | 0151886 A1 | 8/1985 |
| EP | 0201105 A1 | 11/1986 |
| EP | 0331021 A1 | 9/1989 |
| EP | 1829851 A1 | 9/2007 |
| EP | 2679303 A1 | 1/2014 |
| FR | 2743060 A1 | 7/1997 |
| GB | 287846 | 4/1929 |
| GB | 312345 | 8/1930 |
| GB | 470773 | 8/1937 |
| JP | 59025334 A | 2/1984 |
| JP | H0753676 A | 10/1988 |
| JP | 5186392 A | 7/1993 |
| JP | 2009220105 A | 10/2009 |
| SU | 362814 A1 | 12/1972 |
| WO | 2011131609 A2 | 10/2011 |
| WO | 2012004572 A1 | 1/2012 |
| WO | 2013055334 A1 | 4/2013 |
| WO | 2013116492 A1 | 8/2013 |
| WO | 2014130465 A1 | 8/2014 |
| WO | 2015085002 A1 | 6/2015 |
| WO | 2017031439 A1 | 2/2017 |

OTHER PUBLICATIONS

Filing receipt and specification for provisional patent application entitled "Production of ethyl acetate and butyl acetates from ethanol," by Sagar B. Gadewar, et al., filed Dec. 4, 2013 as U.S. Appl. No. 61/911,832.

Notice of Allowance dated Jun. 20, 2016 (8 pages), U.S. Appl. No. 14/023,125, filed Sep. 10, 2013.

Filing receipt and specification for provisional patent application entitled "Production of higher alcohols from ethanol," by Brian Christopher Vicente, et al., filed Dec. 5, 2013 as U.S. Appl. No. 61/912,235.

Filing receipt and specification for provisional patent application entitled "Ethyl acetate production," by Sagar B. Gadewar, filed Oct. 20, 2009 as U.S. Appl. No. 61/253,349.

Foreign communication from a related counterpart application—International Search Report and Written Opinion, PCT/US2011/056015, dated May 24, 2012, 8 pages.

Foreign communication from a related counterpart application—International Preliminary Report on Patentability, PCT/US2011/056015, dated Apr. 15, 2014, 6 pages.

Foreign communication from a related counterpart application—International Search Report and Written Opinion, PCT/US2013/024104, dated May 30, 2013, 12 pages.

Inui, Kanichiro, et al., "Direct synthesis of ethyl acetate from ethanol carried out under pressure," Journal of catalysis, 2002, pp. 207-215, vol. 212, Elsevier Science.

Inui, Kanichiro, et al., "Effective formation of ethyl acetate from ethanol over Cu—Zn—Zr—Al—O catalyst," Journal of Molecular Catalysis A: Chemical, 2004, pp. 147-156, vol. 216, Elsevier B.V.

Machine translation (9 pages) of French U.S. Pat. No. 2743060 A1 issued on Jul. 4, 1997.

Santacesaria, E., et al., "Ethanol dehydrogenation to ethyl acetate by using copper and copper chromite catalysts," Chemical Engineering Journal, 2012, pp. 209-220, vol. 179, Elsevier B.V.

Smith, Michael B., "March's advanced organic chemistry: reactions, mechanisms, and structure," 7th edition, 2013, 8 pages of cover, publishing information, and contents, John Wiley & Sons, Inc.

Takeshita, Kenji, et al., "Reduced copper catalyzed conversion of primary alcohols into esters and ketones," Bulletin of the Chemical Society of Japan, Sep. 1978, pp. 2622-2627, vol. 51, No. 9.

Tsai, Reui-Chiang, et al., "Design and control of the side reactor configuration for production of ethyl acetate," Ind. Eng. Chem. Res., 2008, pp. 9472-9484, vol. 47, No. 23, American Chemical Society.

Vogel, Arthur Israel, "Vogel's textbook of practical organic chemistry," 5th edition, revised by Brian S. Furniss, et al., 1989, 15 pages of cover, publishing information, and contents, John Wiley & Sons, Inc.

Yang, Ke Wu, et al., "One-step synthesis of n-Butanol from ethanol condensation over alumina-supported metal catalysts," Chinese Chemical Letters, 2004, pp. 1497-1500, vol. 15, No. 12.

Foreign communication from a related counterpart application—International Search Report and Written Opinion, PCT/US2014/053894, dated Oct. 31, 2014, 9 pages.

Foreign communication from a related counterpart application—Search Report, European Application No. 11873809.5 dated Apr. 15, 2015, 7 pages.

Foreign communication from a related counterpart application—International Preliminary Report on Patentability, PCT/US2013/024104, dated Aug. 5, 2014, 9 pages.

Foreign communication from a related counterpart application—International Search Report and Written Opinion, PCT/US2014/016957, dated Jun. 27, 2014, 9 pages.

Le Valant, Anthony et al., "Hydrogen production from raw bioethanol over Rh/MgAl2O4 catalyst impact of impurities: Heavy alcohol, aldehyde, ester, acid and amine," Catalysis Today, 2008, vol. 138, Nos. 3-4, pp. 169-174.

Xia, Ke et al. "Analysis of the catalytic activity induction and deactivation of PtIn/Mg(Al)O catalysts for propane dehydrogenation reaction," RSC Advances, Jul. 14, 2015 (e-pub), vol. 5, No. 79, pp. 64689-64695.

Galvita, Vladimir et al., "Ethane dehydrogenation on Pt/Mg(Al)O and PtSn/Mg(Al)O catalysts," Journal of Catalysis, 2010, vol. 271, No. 2, pp. 209-219.

Hui, Sun, Multifunctional and multi-staged reactors for liquid fuel generation from renewable feedstocks, 2012, PhD Thesis.

Foreign communication from a related counterpart application—International Search Report and Written Opinion, PCT/US2014/068439, dated Feb. 26, 2015, 12 pages.

Foreign communication from a related counterpart application—International Preliminary Report on Patentability, PCT/US2014/068439, dated Jun. 16, 2016, 9 pages.

Foreign communication from a related counterpart application—International Search Report and Written Opinion, PCT/US2016/047805, dated Nov. 28, 2016, 20 pages.

Foreign communication from a related counterpart application—International Preliminary Report on Patentability, PCT/US2016/047805, dated Mar. 1, 2018, 18 pages.

Specification and Electronic Acknowledgment Receipt of U.S. Appl. No. 15/753,064 entitled, "Composition of Catalysts for Conversion of Ethanol to N-Butanol and Higher Alcohols," filed Feb. 15, 2018, 53 pages.

* cited by examiner

PRODUCTION OF BUTYL ACETATE FROM ETHANOL

CROSS-REFERENCE TO RELATED APPLICATIONS

This application is a filing under 35 U.S.C. 371 of International Application No. PCT/US2014/068439 filed Dec. 3, 2014, entitled "Production of Butyl Acetate from Ethanol," which claims the benefit of U.S. Provisional Application No. 61/911,832 filed on Dec. 4, 2013 which is incorporated herein by reference in its entirety for all purposes.

BACKGROUND

N-butyl acetate can be produced commercially from butyl alcohol and acetic acid by esterification using sulfuric acid as catalyst. In this process, acetic acid, butanol, and sulfuric acid are heated in a reactor to 89° C. to form the n-butyl acetate. Vapors containing butyl acetate, butanol, and water are removed and condensed. The top layer is fed to low boiler column where unreacted alcohol is flashed off and recycled to the reactor. The crude ester mixture undergoes a second distillation to separate the butyl acetate from other by-products. The n-butanol used in this process is usually derived by hydroformylation of propene followed by hydrogenation, while acetic acid is produced commercially by a number of methods such as methanol carbonylation, acetaldehyde oxidation, and ethylene oxidation.

The commercial production of n-butanol and acetic acid both rely on petroleum and natural gas based feedstocks. Further, the production of n-butyl acetate from these reactants requires a multitude of steps involving a number of intermediate products. All of these factors result in a relatively high price for n-butyl acetate.

SUMMARY

In an embodiment, a reactive distillation method comprises introducing a feed stream to a reactive distillation column, wherein the feed stream comprises ethanol, contacting the feed stream with one or more catalysts in the reactive distillation column during a distillation, and removing butyl acetate during the distillation from the reactive distillation column as a bottoms stream. The feed stream reacts in the presence of the one or more catalysts to produce a reaction product comprising ethyl acetate, butanol, and water, wherein the butanol and the ethyl acetate react to produce a reaction product comprising the butyl acetate. The method may also include removing ethyl acetate, butanol, or both during the distillation from the reactive distillation column in the bottoms stream. The method may also include increasing a ratio of the amount of the butyl acetate to the ethyl acetate, butanol, or both in the bottoms stream by increasing the pressure in the reactive distillation column. The method may also include increasing a ratio of the amount of the butyl acetate to the ethyl acetate, butanol, or both in the bottoms stream by providing a non-reactive packing in a lower portion of the reactive distillation column. The method may also include contacting the bottoms stream with a hydrogenation catalyst and hydrogen to hydrogenate at least a portion of a contaminant in the bottoms stream, and separating the hydrogenated portion of the contaminant from the bottoms stream. The hydrogenation catalyst may comprise a Group VIII metal, a Group VI metal, or any combination thereof. The catalyst may comprise a Guerbet reaction catalyst, a solid base multicomponent oxide catalyst, a solid acid/base bifunctional catalyst, a zeolite with alkali counterions, a magnesium oxide catalyst, an oxide powder catalyst, or any combination thereof. The catalyst may comprise a hydroxyapatite Guerbet reaction catalyst, a solid base Guerbet reaction catalyst, or a combination thereof. The catalyst may comprise a catalyst component represented by the formula:

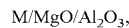

where M represents palladium, rhodium, nickel, or copper, or oxides thereof. The catalyst may comprise a hydroxyapatite represented by the formula:

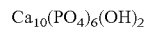

where the ratio of calcium to phosphorus (Ca:P) is between about 1.5 and about 1.8. The catalyst may comprise an apatite structure satisfying the formula:

where M represents calcium, strontium, magnesium, barium, lead, cadmium, iron, cobalt, nickel, zinc, or hydrogen, wherein M' represents phosphorus, vanadium, arsenic, carbon, or sulfur, wherein X represents a fluorine, chlorine, bromine, or a hydroxide, and wherein a is about 10, b is about 3, c is about 6, and the ratio of a to c is between about 1.5 and about 1.8. The catalyst may comprise a calcium phosphate, a calcium phosphate carbonate, a calcium pyrophosphate, a magnesium phosphate, a magnesium phosphate carbonate, a magnesium pyrophosphate or any combination thereof. The catalyst may comprise magnesium oxide, magnesium hydroxide, magnesium phosphate hydrate ($Mg_3(PO_4)_2 \cdot 8H_2O$), calcium oxide, calcium hydroxide, calcium fluoride, calcium silicate (wollastonite), calcium sulfate dihydrate (gypsum), lithium phosphate, aluminum phosphate, titanium dioxide, fluorapatite ($Ca_{10}(PO_4)_6F_2$), tetracalcium phosphate ($Ca_4(PO_4)_2O$), hydrotalcite, talc, kaolin, sepiolite, or any combination thereof. The catalyst may comprise at least one catalytic component selected from the group consisting of: copper, copper oxide, barium, barium oxide, ruthenium, ruthenium oxide, rhodium, rhodium oxide, platinum, platinum oxide, palladium, palladium oxide, rhenium, rhenium oxide, silver, silver oxide, cadmium, cadmium oxide, zinc, zinc oxide, zirconium, zirconium oxide, gold, gold oxide, thallium, thallium oxide, magnesium, magnesium oxide, manganese, manganese oxide, aluminum, aluminum oxide, chromium, chromium oxide, nickel, nickel oxide, iron, iron oxide, molybdenum, molybdenum oxide, sodium, sodium oxide, sodium carbonate, strontium, strontium oxide, tin, tin oxide, and any mixture thereof. The catalyst may comprise a multi-component catalyst. The multi-component catalyst may comprise a first catalyst component and a second catalyst component, wherein the first catalyst component is configured to convert at a portion of the ethanol in the feed stream to the ethyl acetate, and wherein the second catalyst component is configured to convert at least a portion of the ethanol in the feed stream into the butanol and water. The method may also include removing a side stream from the reactive distillation column, contacting the side stream with a side reactor catalyst, wherein the side stream reacts in the presence of the side reactor catalyst to produce butyl acetate, and reintroducing the butyl acetate produced in the presence of the side reactor catalyst to the reactive distillation column. The method may also include removing a side stream from the reactive distillation column, contacting the side stream with a side reactor catalyst, wherein the side stream reacts in the presence of the side reactor catalyst to produce at least one of ethyl acetate or butanol, and reintroducing the at least one of ethyl acetate or butanol produced in the presence of the side reactor catalyst to the reactive distillation column. The method may also include removing a plurality of side streams from the reactive distillation column, introducing each of the plurality of side streams into a corresponding plurality of side reactors, contacting each respective side stream with a side reactor catalyst in the corresponding side reactor, and reintroducing the at least one of ethyl acetate, butanol, or butyl acetate produced in each side to the reactive distillation column. Each side reactor of the plurality of side reactors may comprise a side reactor catalyst, and each respective side stream may react in the presence of the side reactor catalyst to produce at least one of ethyl acetate, butanol, or butyl acetate. The method may also include introducing a second feed stream comprising hydrogen to the reactive distillation column.

In an embodiment, a reactive distillation method comprises introducing a feed stream to a reactive distillation column, wherein the feed stream comprises ethanol, contacting the feed stream with one or more catalysts during a distillation, wherein the feed stream reacts in the presence of the one or more catalysts, producing a reaction product comprising butyl acetate based on the contacting, and removing butyl acetate during the distillation from the reactive distillation column as a bottoms stream. The one or more catalysts may be disposed in the reactive distillation column. The one or more catalysts can be disposed in a side reactor in fluid communication with the reactive distillation column. The method may also include removing a side stream from the reactive distillation column, contacting the side stream with the one or more catalysts in the side reactor, reintroducing the butyl acetate produced in the presence of the one or more catalysts to the reactive distillation column. The side stream can react in the presence of the one or more catalysts to produce butyl acetate. The method may also include removing a side stream from the reactive distillation column, contacting the side stream with the one or more catalysts in the side reactor, and reintroducing the at least one of ethyl acetate or butanol produced in the presence of the one or more catalysts to the reactive distillation column. The side stream can react in the presence of the one or more catalysts to produce at least one of ethyl acetate or butanol. The method may also include removing a plurality of side streams from the reactive distillation column, introducing each of the plurality of side streams into a corresponding plurality of side reactors, contacting each respective side stream with the catalyst in the corresponding side reactor, reintroducing the at least one of ethyl acetate, butanol, or butyl acetate produced in each side to the reactive distillation column. Each side reactor of the plurality of side reactors can comprise a catalyst of the one or more catalysts, and each respective side stream can react in the presence of the catalyst to produce at least one of ethyl acetate, butanol, or butyl acetate. The method may also include removing the bottoms stream from the reactive distillation column, where the bottoms stream comprises the butyl acetate and ethyl acetate, separating at least a portion of the ethyl acetate from the butyl acetate, and recycling the ethyl acetate to the reactive distillation column. The method may also include adjusting a pressure of the reactive distillation column to increase butyl acetate production. The method may also include producing butanol and ethyl acetate based on the contacting of the feed stream with the one or more catalysts during the distillation, contacting the butanol and the ethyl acetate with the one or more catalysts, and producing the butyl acetate based on the contacting of the butanol and the ethyl acetate with the one or more catalysts.

In an embodiment, a reactive distillation system comprises a feed stream comprising ethanol, and a reactive distillation column. The reactive distillation column comprises: one or more catalysts disposed within the reactive distillation column, an ethanol feed configured to pass the feed stream comprising ethanol over at least a portion of the one or more catalysts to produce ethyl acetate and butanol, an overhead product hydrogen removal passage, and a bottoms product butyl acetate removal passage. The one or more catalysts are configured to cause ethyl acetate and butanol to react in the presence of the one or more catalysts to produce butyl acetate. The system can also include a side reactor in fluid communication with the reactive distillation column, an inlet in fluid communication with the side reactor and the reactive distillation column, and configured to pass a fluid from the reactive distillation column over the second catalyst, and an outlet in fluid communication with the side reactor and the reactive distillation column, and configured to pass the fluid from the outlet of the side reactor to the reactive distillation column. The side reactor comprises a second catalyst. The inlet can be coupled to the reactive distillation column below the outlet, and the fluid can be a vapor. The inlet can be coupled to the reactive distillation column above the outlet, and the fluid can be a liquid. The system can also include a second side reactor in fluid communication with the reactive distillation column, a second inlet in fluid communication with the second side reactor and the reactive distillation column, and configured to pass a second fluid from the reactive distillation column over the third catalyst, and a second outlet in fluid communication with the second side reactor and the reactive distillation column, and configured to pass the second fluid from the second outlet of the second side reactor to the reactive distillation column. The second side reactor can comprise a third catalyst. The distillation column can also include a hydrogenation catalyst disposed within the reactive distillation column, and the reactive distillation system can also include a hydrogen feed in fluid communication with the reactive distillation column and configured to pass hydrogen over at least a portion of the hydrogenation catalyst.

In an embodiment, a reactive distillation method comprises contacting a first feed stream comprising ethanol with a first catalysts, producing ethyl acetate in a first product stream in response to contacting the first feed stream with the first catalyst, separating at least a portion of the ethyl acetate from the first product stream, contacting a second feed stream comprising ethanol with a second catalysts, producing butanol in a second product stream in response to contacting the second feed stream with the second catalyst, separating at least a portion of the butanol from the second product stream, introducing the portion of the ethyl acetate and the portion of the butanol into a reactive distillation column as one or more feed streams, contacting the ethyl acetate and butanol within the reactive distillation column, producing a reaction product comprising butyl acetate based on the contacting, and removing butyl acetate during the distillation from the reactive distillation column as a bottoms stream. Contacting the ethyl acetate and butanol within the reactive distillation column can occur in the presence of one or more catalysts. The one or more catalysts can be disposed in one or more side reactors. Contacting the first feed stream with the first catalyst can occur within a first reactive distillation column, and/or contacting the second feed stream with the second catalyst can occur within a second reactive distillation column.

These and other features will be more clearly understood from the following detailed description taken in conjunction with the accompanying drawings and claims.

BRIEF DESCRIPTION OF THE DRAWINGS

For a more complete understanding of the present disclosure and the advantages thereof, reference is now made to the following brief description, taken in connection with the accompanying drawings and detailed description.

DETAILED DESCRIPTION

Figure 1A:
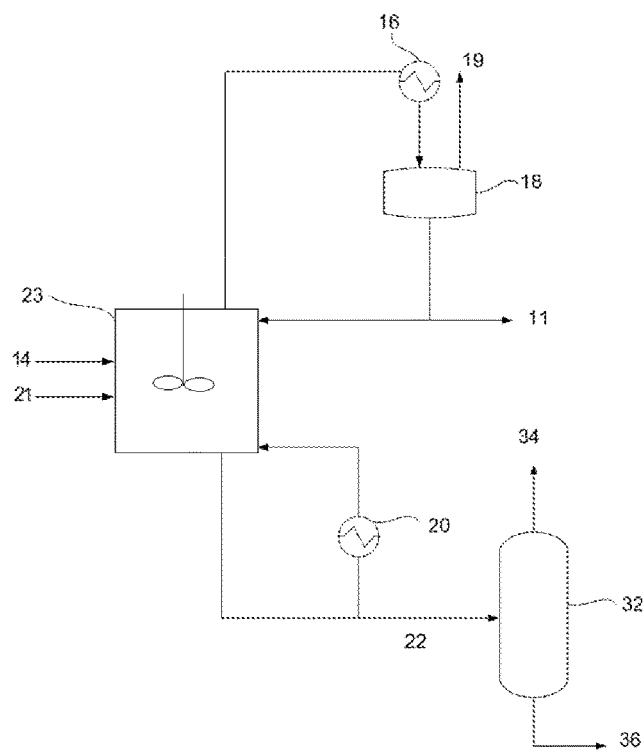
FIGS. 1(a) and 1(b) show a simplified schematic of a reactive distillation system according to an embodiment.

A reactive distillation system and process are disclosed herein for producing butyl acetate from ethanol, and in some embodiments to produce butyl acetate and ethyl acetate. Reactive distillation beneficially allows the process to occur in a single reactor/distillation column where the catalyst can be positioned as reactive packing. This configuration allows for continuous operation where reactant can be added and heavier and lighter products can be removed as needed from the bottom and top of the column, respectively. In operation, the vapors condense and evaporate continuously on the catalyst surface where the reactions take place. By varying operational parameters such as temperature, pressure and reflux ratio the reaction can be carried out to a high level of conversion. Recirculation of aldehydes and other intermediates can be used to ensure reaction to desirable n-butyl acetate and improve feedstock utilization.

The n-butyl acetate production process is based on the conversion of ethanol into ethyl acetate and n-butanol followed by transesterification of ethyl acetate and n-butanol. Both ethyl acetate and n-butanol can be made from ethanol via dehydrogenation and dehydration reactions, respectively. In some embodiments, the process can use a single bifunctional catalyst that would carry out several reactions simultaneously. The catalyst may be capable of converting ethanol into both ethyl acetate and n-butanol, as well as catalyze the transesterification of ethyl acetate and n-butanol to give n-butyl acetate and ethanol, which is internally recycled in the reactive distillation column. In an embodiment, the catalyst comprises an alcohol dehydrogenation component to facilitate the first step in the reaction to generate acetaldehyde, which is an intermediate for the reaction that can generate ethyl acetate and/or n-butanol. When the dehydrogenation component comprises copper (e.g., copper metal, copper oxide, etc.), the catalyst may also be a catalyst of the Tishchenko mechanism reaction where ethanol and acetaldehyde react to form ethyl acetate. The second functionality can catalyze the aldol condensation of acetaldehyde to n-butanol and may be either an acidic or a basic catalyst component. The transesterification reaction of ethyl acetate and n-butanol to n-butyl acetate and ethanol does not need to be catalyzed, however it may be catalyzed by an acidic and/or a basic catalyst center. In some embodiments, a plurality of catalysts can be used where each catalyst is targeted to one or more of the reactions.

In the first step of the reaction sequence for producing butyl acetate, ethanol is reversibly dehydrogenated to form acetaldehyde.

$$C_2H_5OH \rightleftharpoons CH_3CHO + H_2 \qquad \text{(Eq. 1)}$$

Acetaldehyde is a reactive species that may follow one of several different reaction pathways. In the presence of a solid catalyst with strong basic functionality, an aldol condensation is the most likely pathway that leads to the formation of higher aldehydes (e.g. as shown in Eq. 2), which, in a reaction medium rich in hydrogen, would be hydrogenated to the corresponding alcohols (e.g., as shown in Eqs. 2-4)

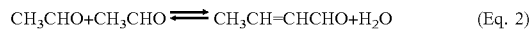

$$CH_3CHO + CH_3CHO \rightleftharpoons CH_3CH{=}CHCHO + H_2O \qquad \text{(Eq. 2)}$$

$$CH_3CH{=}CHCHO + H_2 \rightleftharpoons CH_3CH_2CH_2CHO \qquad \text{(Eq. 3)}$$

$$CH_3CH_2CH_2CHO + H_2 \rightleftharpoons CH_3CH_2CH_2CH_2OH \qquad \text{(Eq. 4)}$$

The butanol produced may comprise n-butanol. The other desirable reaction pathway for acetaldehyde that takes place over the bifunctional catalyst is the Tishchenko reaction (e.g., as shown in Eq. 5).

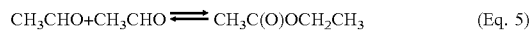

$$CH_3CHO + CH_3CHO \rightleftharpoons CH_3C(O)OCH_2CH_3 \qquad \text{(Eq. 5)}$$

The aldol condensation reaction and the Tishchenko reaction occur at similar reaction conditions, making it possible to target the preparation of a catalyst for which the rates of ethyl acetate and n-butanol generation are quite similar. In an embodiment, the catalyst comprises a plurality of active components, with each component's activity matched so that ethyl acetate and n-butanol are generated in nearly equal molar ratios.

In a reactive distillation process in which the reactions above are taking place simultaneously, ethyl acetate and n-butanol may be concentrated in the lower portion of the column, with ethanol, hydrogen, and water concentrating toward the upper portion of the column. The transesterification reaction of ethyl acetate and n-butanol to n-butyl acetate and ethanol does not need to be catalyzed and can occur even if no catalyst is present in the lower portion of the column. The presence of a catalyst can accelerate the rate of the reaction towards equilibrium. In the lower portion of the column, the ethyl acetate and n-butanol can undergo a transesterification reaction, yielding n-butyl acetate product and ethanol (e.g., as shown in Eq. 6).

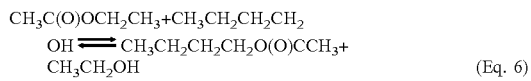

(Eq. 6)

A transesterification reaction is a reaction where either the alcohol or the acid moiety of the ester gets reversibly exchanged with another. In this case, the transesterification is of the alcoholysis type where the ethyl alcohol moiety is reversibly replaced by n-butanol to form n-butyl acetate and ethanol. The process of transesterification can be catalyzed by either acid or base. Since the aldol condensation catalyst can also be catalyzed by either an acid or base, a suitable transesterification catalyst may be present in the reactive distillation column, and thus, catalyze the transesterification reaction.

In the reactive distillation configuration, butyl acetate can be removed from the reboiler to allow the transesterification reaction to proceed further than what is expected from the equilibrium between butanol and ethyl acetate. Hydrogen is removed from the top of the column as light byproduct while lighter ethanol, acetaldehyde can be removed as a distillate stream which is dehydrated and refluxed back into the reactive distillation column. Water can be carried into the distillate stream due to the formation of lower boiling azeotrope between ethanol and water.

The overall reaction taking place in the reactive distillation column is the following:

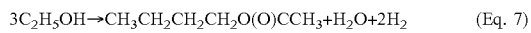

(Eq. 7)

The raw material of this process may comprise only ethanol, which may present an advantage relative to other processes requiring multiple feedstocks. In addition, bio-derived ethanol may be used to allow the process to be operated from renewable ethanol sources. Further, the present system and method may utilize base-metal catalysts, which may be relatively inexpensive.

While the reaction described above is discussed in the context of n-butanol, other isomers of butyl acetate can also be made via the same trans-esterification reaction when the appropriate butanol isomer is a by-product of the ethyl acetate process catalysts (in particular sec-butyl acetate from 2-butanol). If a bio-ethanol with a high concentration of iso-butanol is used as a feed it may be possible to recover iso-butyl acetate from the reaction process.

In chemical processing, chemical reaction and the purification of the desired products by distillation may be carried out sequentially. The performance of this chemical process structure may be improved by the integration of reaction and distillation in a single multifunctional process unit. As noted above, this integration concept is called "reactive distillation." The reaction may occur within the same vessel, or a second vessel in fluid communication with a separation vessel may be considered a reactive distillation. For example, a side reactor carrying out a reaction that is in fluid communication with a distillation column that removes at least a portion of the products would be considered a reactive distillation process. As advantages of this integration, chemical equilibrium limitations may be overcome, higher selectivities may be achieved, the heat of reaction may be used in situ for distillation, auxiliary solvents may be avoided, azeotropic and/or closely boiling mixtures may be more easily separated, or any combination thereof. Increased process efficiency and reduction in overall capital costs may result from the use of this approach.

A reactive distillation system comprises at least one separator (e.g., a distillation tower) in which a reaction is occurring. In general, suitable separators may include any process equipment suitable for separating at least one inlet stream into a plurality of effluent streams having different compositions, states, temperatures, and/or pressures. For example, the separator may be a column having trays, packing, or some other type of complex internal structure. Examples of such columns include scrubbers, strippers, absorbers, adsorbers, packed columns, and distillation columns having valve, sieve, or other types of trays. Such columns may employ weirs, downspouts, internal baffles, temperature control elements, pressure control elements, or any combination thereof. Such columns may also employ some combination of reflux condensers and/or reboilers, including intermediate stage condensers and reboilers. In an embodiment, the reactive distillation system described herein may comprise a distillation tower having at least one catalyst disposed therein.

As indicated above, the present systems and methods provide for the production of butyl acetate at a relatively low cost, along with plants or distillation systems with significantly reduced complexity using reactive distillation. The present disclosure further provides improved processes for the production of butyl acetate from an ethanol feed or from a feedstock comprising a major proportion of ethanol and a minor proportion of impurities such as water. While not commonly present in alcohol feed streams, impurities that can poison the particular catalyst used should be limited, avoided and/or removed. For example, sulfur or nitrogen heterocyclic compounds can frequently act as catalyst poisons and, if present, should be removed before introducing the ethanol feed stream to the reactive distillation column. In an embodiment, the ethanol feed stream may comprise water. The presence of water in the ethanol feed does not severely reduce the performance of the catalysts, which may tolerate up to about 5% water by weight in the ethanol feed. Ethanol conversion may be reduced when using an ethanol source with significant water content. The use of an alcohol feed comprising a small amount of water may be advantageous by allowing for the use a potentially less expensive alcohol source in the form of the alcohol/water azeotrope (e.g., about 4.4% water by weight in an ethanol feed).

The present systems and methods provide a reactive distillation system in which ethanol is fed to a reactive distillation column. In an embodiment, ethanol may be the sole or primary component of the feed. Reference to a "single feed" to a reactive distillation column means that the column has only one chemical feed stream supplying intended reactant(s) to the column. Nonetheless, such a single feed distillation column may have multiple entry points for the reactant, or recycling feed streams where a part of the reactant liquid or a partial distillate is drawn from the column and fed back into the column at a different point, e.g., to achieve improved separation and/or more complete reaction.

The single feed may comprise a single reactant such as ethanol. A "single ethanol feed" refers to a single feed stream in which ethanol is the sole or at least the primary constituent. The single feed may also comprise more than one reactant, such as a feed stream of ethanol and water. A "single ethanol and water feed" thus refers to a single feed stream in which ethanol and water are the sole or at least the primary constituents. In contrast, the term "dual feed" in the context of a distillation column refers to two separate chemical feed streams. For example, in some of the present embodiments, dual feeds can include an ethanol feed stream and a separate hydrogen feed stream.

In a simplistic form, as shown in FIG. 1(a), the reactive distillation system may comprise a continuous stirred-tank reactor (CSTR) charged with a catalyst that is coupled to a phase separator and configured for the production of butyl acetate. In an embodiment, the production of butyl acetate may be accomplished by passing the feed stream 14, which comprises a feed of ethanol, into the CSTR 23 wherein the feed mixes and contacts the dehydrating catalyst under conditions where ethyl acetate and butanol are formed followed by the reaction of the ethyl acetate and butanol to form butyl acetate and ethanol. Water and hydrogen are formed as byproducts during the reaction within the CSTR 23. An optional second feed stream 21 comprising hydrogen may also be introduced into the CSTR 23. As the conversions proceed, the resulting liquid mixture may pass to a phase from which the water leaves as distillate 34 and butyl acetate can leave as a bottom product 36. Phase separator 32 may be any phase separator, which is a vessel that separates an inlet stream into a substantially vapor stream and a substantially liquid stream, such as a knock-out drum, flash drum, reboiler, condenser, or other heat exchanger. Such vessels also may have some internal baffles, temperature control elements, pressure control elements, or any combination thereof, but generally lack any trays or other type of complex internal structure commonly found in columns. A vapor phase may pass out of the CSTR 23 and pass to a condenser 41. The vapor phase may comprise the hydrogen and a portion of the water and unreacted ethanol. The water and ethanol may be condensed and separated in a separator 18. The hydrogen may leave the separator 18 as an overhead stream 19. The liquid stream may be divided into an outlet stream 11 and a reflux stream passing back to the CSTR 23.

Figure 1B:
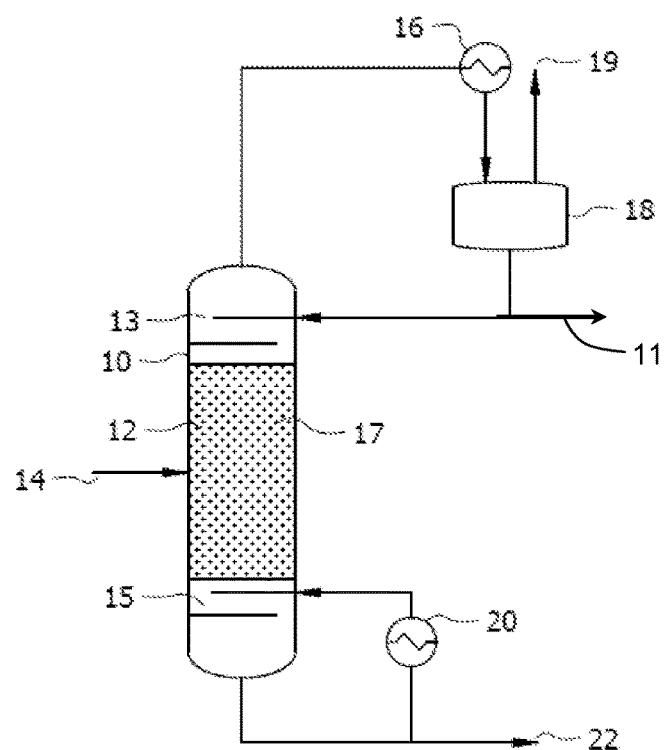

An embodiment of a reactive distillation column with a single feed of ethanol is shown schematically in FIG. 1(b). Column 10 contains a generally central catalyst zone 12, and usually will include a top stage or non-reactive rectifying section 13 and a bottom stage or non-reactive stripping section 15. The ethanol feed 14 may be fed to the middle part of the reactive distillation column. While illustrated as having the catalyst 17 disposed within the central portion of the column 10, the catalyst 17 may be located only above or below the ethanol feed location. In an embodiment, the catalyst 17 may be disposed only above the feed location, and the lower portion of the column 10 may comprise trays, packing, or the like to provide a stripping section. In some embodiments, the catalyst 17 may be disposed only below the feed location, and the upper portion of the column 10 may comprise trays, packing, or the like to provide a rectifying section.

Distillate removed at the top of the column is passed through a partial condenser 16, and water can be separated from lower boiling constituents in reflux tank 18. Lower boiling constituents may leave the system as an overhead product stream 19, which in an embodiment may comprise hydrogen and trace amounts of water, ethanol, butanol, one or more reaction byproducts, or any combination thereof. The condensate (e.g., the reflux), or at least some portion thereof, can be cycled back to the column for further reaction and/or separation. Condensate not cycled back to the column leaves as overhead product stream 11. The condensate can comprise the majority water and, in some embodiments, minor amounts of ethanol and/or butanol. In an embodiment, a portion of the condensate comprising water and ethanol may be dehydrated and returned to the column 10. The bottoms product can be passed through reboiler 20, where a portion of the bottoms product is converted to vapor and introduced back to the lower portion of the column. The remaining bottoms product may pass out of the system as product stream 22. Alternatively, only a portion of the bottoms product may be passed through reboiler 20, with the vapor portion passing back to the lower portion of the column and the remainder of the bottoms product being combined with any bottoms product bypassing the reboiler 20 and passing out of the system as product stream 22 for further processes and/or use as a final product. The product stream 22 may comprise the butyl acetate along with potentially any side products produced by the reaction. Some trace amounts of the ethanol, ethyl acetate, and/or butanol may be present in the bottom stream 22. The column reflux and reboil ratios may be maintained such that essentially pure butyl acetate can be obtained as the bottoms product. In an embodiment, the bottoms product stream 22 may comprise greater than about 90%, greater than about 95%, greater than about 96%, greater than about 97%, greater than about 98%, greater than about 99%, or greater than about 99.5% butyl acetate by weight. In some embodiments, a mixture of ethyl acetate and butyl acetate may be present in the bottom stream 22, where the ethyl acetate and butyl acetate can be separated to generate two product streams.

During operation, the reactants and products flow through the reactor/column reacting and flashing along the length of the reactor/column. In an embodiment, the reaction of the reactants and/or products may occur in the catalyst zone 12, and the reactions may occur in the vapor and/or liquid phase. Specific catalysts useful in the reactive distillation systems and methods disclosed herein are discussed in more detail below. In an embodiment, the reaction of ethanol over the catalysts can occur in a vapor phase in which the ethanol is passed over the catalyst for a given residence time consistent with the desired selectivity and/or conversion. In an embodiment, the reaction of ethanol over the catalysts can occur in a liquid phase reaction where the catalyst can be dispersed in a liquid reactant mixture and/or reactants contact the catalyst in condensed state. A vapor phase reaction and liquid phase reaction would generally occur at similar temperatures, and the pressure of each reaction would depend on the state (e.g., vapor and/or liquid) of the reactants contacting the catalyst(s).

Hydrogen and water can be produced, along with potential side products, due to the reaction over the catalyst. The removal of the overhead stream 11 comprising water, which may occur by flashing, increases the extent of reaction. In general, the water concentration increases from the middle part of the column towards the top of the column. A partial condenser 16 allows water to be removed as a distillate and/or recycled back to the top of the reactive distillation column. At pressures of about 0.1 bar or higher, an azeotrope occurs between ethanol and water. This azeotrope may result in the overhead product 11 that leaves the top of the reactive distillation column 10 containing unreacted ethanol in addition to water. In an embodiment, any unreacted ethanol leaving condenser 16 as overhead stream 11 can be fed to a dehydration unit to produce a dehydrated ethanol stream, which can then be recycled back to column 10 as feed.

The column 10 can be operated at any suitable pressure between about 1 atm and about 80 atm. In an embodiment, the column 10 may be operated at a pressure ranging from about 1 atm to about 5 atm, about 5 atm to about 10 atm, about 10 atm to about 20 atm, about 15 atm to about 20 atm, about 15 atm to about 30 atm, about 20 atm to about 30 atm, about 20 atm to about 50 atm, about 30 atm to about 40 atm, about 40 atm to about 50 atm, or about 50 atm to about 60 atm, about 60 atm to about 70 atm, about 60 atm to about 80 atm, or about 70 atm to about 80 atm. The temperature profile in the column is dictated by the mixture boiling point along the height of the column. In an embodiment the temperature within the column may range from about 100° C. to about 400° C., about 150° C. to about 350° C., about 200° C. to about 325° C., about 230° C. to about 300° C., or about 260° C. to about 300° C. The column 10 may comprise any number of stages equivalent to a number of theoretical stages sufficient to effect the reaction and separation of the butyl acetate to a desired purity. In an embodiment, the number of stages or the number of height equivalents of a theoretical plate (HETP) may range from about 1 to about 100, including for example from about 1 to about 10, about 10 to about 20, about 10 to about 50, about 20 to about 30, about 20 to about 70, about 30 to about 40, about 30 to about 50, about 30 to about 100, about 50 to about 70, about 50 to about 100, or about 70 to about 100.

In a reactive distillation process for making butyl acetate, the temperature of the reactants in contact with the catalyst in the column can be controlled by adjusting the operating pressure of the column. By increasing the pressure, and therefore temperature, a greater yield of butyl acetate can be realized. Similarly, by decreasing the operating pressure, and therefore temperature, the process can be adjusted to make less butyl acetate. Also, by selectively locating the catalyst section within the column 10, the temperature within the catalytic section can be controlled, thereby controlling the product distribution. For example, the heavier reactants including ethyl acetate and butanol may be concentrated in the lower portion of the column. By placing the butyl acetate production catalyst in the lower portion of the column, the reaction conditions and reactant concentrations may enable a greater yield of butyl acetate.

An alternative process for making butyl acetate directly from ethanol in a reactive distillation column with a single catalyst is to use multiple catalysts in a single process. In a reactive distillation column, the reactive sections could include one or more catalysts for a first product (e.g., ethyl acetate, butanol, etc.) production and one or more catalysts for butyl acetate production. The catalysts in each section can be configured to react at the temperature in the portion of the column in which the catalyst(s) are located.

In an embodiment, the systems and methods may also include hydrogenating contaminants or reaction byproducts in the bottoms stream or in the reacted fluid after it has passed over the conversion catalyst. Species that may be produced as byproducts in the reaction may include aldehydes, such as acetaldehyde, n-butyraldehyde, and/or crotonaldehyde; ethers, such as ethyl ether and n-butyl ether, and/or one or more alcohols. Some of these byproducts boil at temperatures close to the boiling point of butyl acetate and may be difficult to separate.

Figure 2:
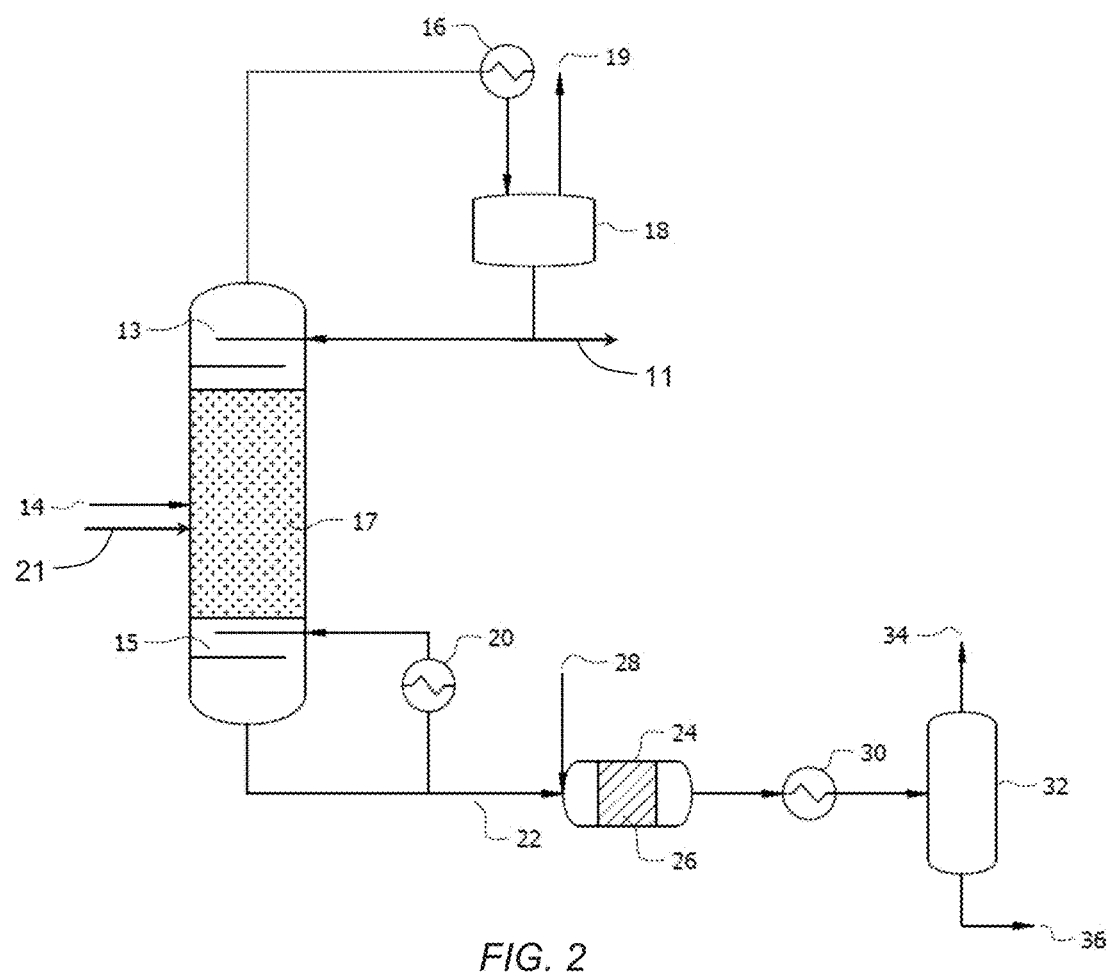
FIG. 2 shows a simplified schematic of a reactive distillation system according to still another embodiment.

FIG. 2 shows a process schematic where the bottoms product 22 from the reactive distillation column 10 illustrated in FIG. 1(b) is sent to a hydrogenation reactor 24 comprising a hydrogenation catalyst 26 with a hydrogen co-feed 28. Suitable hydrogenation catalyst(s) may comprise various components and are described in more detail herein. At least a portion of the byproducts can be hydrogenated, pass through heat exchanger 30, and can then be separated using a separator 32. The separator 32 may comprise any of the types of separators described herein with respect to the reactive distillation system. Alternatively or in addition to the separators already described, the separator 32 may be a phase separator, which is a vessel that separates an inlet stream into a substantially vapor stream and a substantially liquid stream, such as a knock-out drum, flash drum, reboiler, condenser, or other heat exchanger. Such vessels also may have some internal baffles, temperature control elements, pressure control elements, or any combination thereof, but generally lack any trays or other type of complex internal structure commonly found in columns. The separator also may be any other type of separator, such as a membrane separator. In a specific embodiment, the separator is a knockout drum. Finally, the separator may be any combination of the aforementioned separators arranged in series, in parallel, or combinations thereof. In an embodiment, separator 32 comprises a distillation column. The outlet of the hydrogenation reactor 24 may be passed through a heat exchanger 30 (e.g., a condenser) and cooled before entering the separator 32. The heat exchanger 30 may be any equipment suitable for heating or cooling one stream using another stream. Generally, the heat exchanger 30 is a relatively simple device that allows heat to be exchanged between two fluids without the fluids directly contacting each other. Examples of suitable heat exchangers 30 include, but are not limited to, shell and tube heat exchangers, double pipe heat exchangers, plate fin heat exchangers, bayonet heat exchangers, reboilers, condensers, evaporators, and air coolers. In the case of air coolers, one of the fluids comprises atmospheric air, which may be forced over tubes or coils using one or more fans.

The bottoms product stream 36 from the separator 32 may comprise butyl acetate and may have a purity of greater than about 90%, greater than about 95%, greater than about 96%, greater than about 97%, greater than about 98%, greater than about 99%, or greater than about 99.5% by weight. Unconverted ethanol, butanol, and/or ethyl acetate as well as any hydrogenated byproducts may be removed as an overhead product 34, and may be used, for example, as fuel or a feed to one or more processes. In an embodiment, the separator 32 may be operated between a pressure of 1 atm and 80 atm. In an embodiment, the bottoms product stream 36 may pass to another separator. The separator may then separate the bottoms product stream into a butyl acetate stream and a byproduct stream comprising one or more hydrogenation products produced in the hydrogenation reactor 26.

Figure 3:
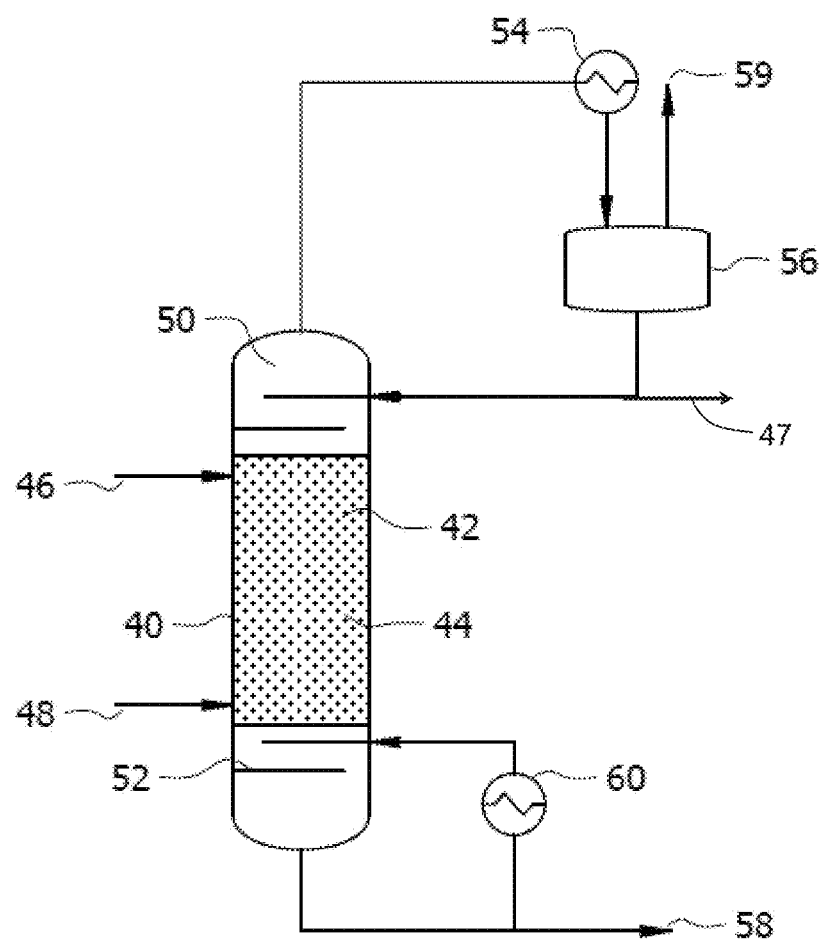
FIG. 3 shows a simplified schematic of a reactive distillation system according to yet another embodiment.

In another embodiment of the invention, the reactive distillation column has two feeds. A schematic for the double feed reactive distillation column is schematically illustrated in FIG. 3. The feed stream comprising the ethanol feed may be fed to the upper part of the column (upper feed stream 46), and hydrogen may be fed to the lower part of the column (lower feed stream 48). This system includes column 40 containing catalyst 42 in catalyst zone 44, and commonly may include a top stage or non-reactive rectifying section 50 and a bottom stage or non-reactive stripping section 52. In the illustrated system, upper feed stream 46 is delivered at or near the top of the catalyst zone 44, and the lower feed stream 48 is delivered at or near the bottom of catalyst zone 44. In an embodiment, upper feed stream 46 comprises ethanol. It should be recognized that columns can be designed with the upper feed stream 46 in other locations, e.g., within the catalyst zone 44 but above the lower feed stream 48, such as from the approximate middle of the catalyst zone 44 to the top of the column 40. Similarly, columns with the lower feed stream 48 in other locations can also be designed, e.g., with the lower feed stream 48 from the approximate middle of the catalyst zone 44 to the bottom of the column 40 or even higher within the catalyst zone 44 but below the upper feed stream 46. In an embodiment, the upper feed stream 46 and the lower feed stream 48 are separated sufficiently to allow byproduct hydrogenation to be substantially completed before hydrogen from the lower feed reaches substantial concentrations of the ethanol being dehydrogenated to ethyl acetate and/or butanol. Examples of conversion catalysts suitable for use in the production of the ethyl acetate, butanol, and the subsequent butyl acetate are described in more detail herein.

Due to boiling point differences, hydrogen, ethanol, and water tend to move towards the top of the column 40 and the ethyl acetate, butanol, and butyl acetate tend to move towards the bottom of the column 40. Byproducts such as acetaldehyde, n-butyraldehyde, and ethyl ether may be produced during the reaction and may move up in the column 40. At least a portion of the byproducts, if present, can be condensed in condenser 54 (e.g., a partial condenser, or a total condenser), passed through reflux tank 56, and recycled back to column 40 as reflux. A product stream 47 comprising water is taken out as distillate from the reflux tank 56. Hydrogen can leave the reflux tank 56 as an overhead stream 59. In an embodiment, product stream 47 further may comprise unreacted ethanol from the feed and can contain a portion of the byproducts (e.g., acetaldehyde, n-butyraldehyde, ethyl ether, crotonaldehyde, etc.). The product stream 47 comprising the ethanol and water can be fed to a dehydration unit to produce a dehydrated ethanol stream, which can then be recycled back to column 40 as feed. A portion of the bottom draw is taken out as the butyl acetate product stream 58, while the remaining portion is passed through reboiler 60 to be recycled to the column 40. In an embodiment, the bottom draw may be passed through a reboiler (e.g., similar to reboiler 60) and optionally passed to a separator where the vapor portion may pass to the column 40 while at least a portion of the remainder is taken out as the butyl acetate product stream 58. The stream passing through the reboiler 60 provides the evaporation effect and vapor flow for operating the column 40. In an embodiment, the product stream 58 may comprise the butyl acetate produced in the column 40 and potentially any side products produced by the reaction.

Byproducts can be produced in the reaction. The lower hydrogen feed 48 is useful in hydrogenating the by-products to produce components that can be more easily separated from the butyl acetate products. The ratio of the ethanol feed to the hydrogen feed can beneficially be adjusted to minimize the amount of close boiling byproducts. In an embodiment, the molar ratio of the ethanol to hydrogen ranges from about 1:10 to about 1000:1, e.g., from about 1:10 to about 1:1, from about 1:1 to about 5:1, from about 1:1 to about 10:1, from about 5:1 to about 25:1, from about 5:1 to about 50:1, from about 10:1 to about 50:1, from about 10:1 to about 100:1, from about 50:1 to about 200:1, from about 50:1 to about 400:1, from about 100:1 to about 500:1, from about 100:1 to about 1000:1, from about 200:1 to about 1000:1, or from about 500:1 to about 1000:1. Water and hydrogen from the reaction leave at the top of the column. In an embodiment, the column 40 may operate at any of the conditions (e.g., operating pressure, operating temperature, etc.) discussed herein with respect to column 10 in FIG. 1(*b*). In addition, the column 40 may have any number of stages, and in an embodiment have any number of stages as described with respect to column 10 in FIG. 1(*b*).

Figure 4:
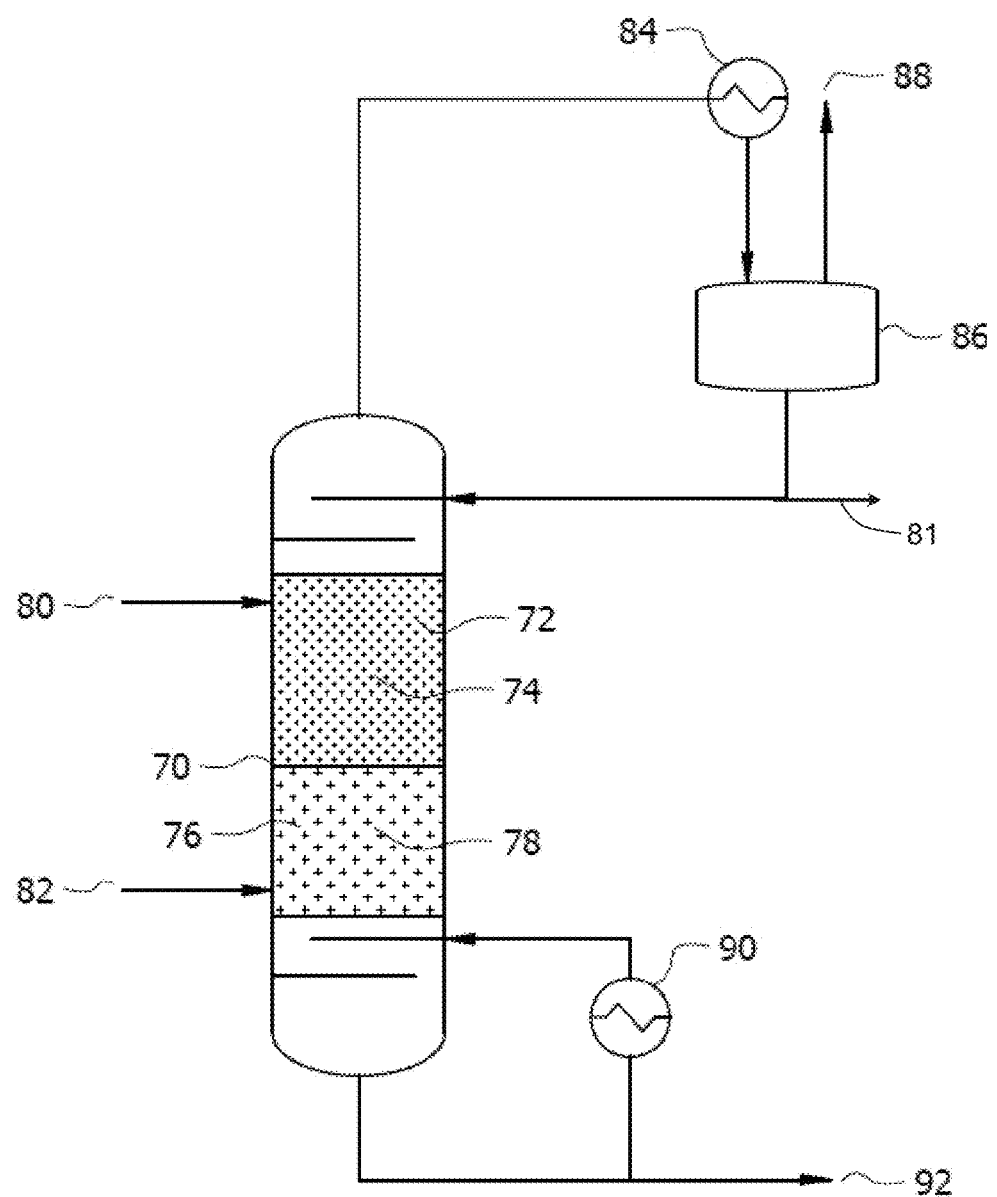
FIG. 4 shows a simplified schematic of a reactive distillation system according to yet another embodiment.

As schematically illustrated in FIG. 4, the reactive distillation column 70 has two feeds 80, 82 and uses two catalyst zones, identified as an upper zone 72 containing Catalyst A 74 and a lower catalyst zone 76 containing Catalyst B 78. Upper feed stream 80 is fed to the upper part of the column 70 (upper feed stream). The upper feed stream 80 may comprise ethanol. A lower feed stream 82 is fed to the lower part of the column 70 (lower feed stream). The lower feed stream 82 may comprise hydrogen The molar ratio of the ethanol to hydrogen may fall within any of the ranges described above with respect to FIG. 3 (e.g., from about 1:10 to about 1000:1, and all sub-ranges). The ethanol may react over the upper catalyst (Catalyst A 74) to produce ethyl acetate, butanol, and/or butyl acetate from the reaction of the ethyl acetate and butanol. Examples of suitable upper catalysts are described in more detail herein with respect to the conversion catalysts. As with previous schematic designs shown, the column 70 will usually include a top stage or non-reactive rectifying section 71 and a bottom stage or non-reactive stripping section 79.

Due to boiling point differences, hydrogen, ethanol, and water may move towards the top of the column 70 and the ethyl acetate, butanol, and butyl acetate may move towards the bottom of the column 70. Byproducts such as acetaldehyde, n-butyraldehyde, and ethyl ether may be produced during the reaction. At least a portion of the byproducts, if present, can be condensed in condenser 84 and recycled back to the reaction zone through reflux tank 86. The lower hydrogen feed stream 82 can be useful in hydrogenating the by-products over the lower catalyst to produce components that can be separated easily from the butyl acetate product, where the lower catalyst can comprise a hydrogenation catalyst. Examples of hydrogenation catalysts are described in more detail herein. In some embodiments, the lower catalyst may also comprise a catalyst used to convert ethyl acetate and butanol to butyl acetate, where the lower catalyst can be the same or different than the upper catalyst.

An overhead product stream comprising water from the reaction leaves at the top of the column 70. In an embodiment, the overhead product stream may further comprise unreacted ethanol. The overhead product stream can be at least partially condensed in condenser 84, and the stream can then be passed to a separator 86. The hydrogen present in the product stream can leave the system as overhead stream 88. A liquid stream can leave the separator 86 and be split into two or more streams. A portion of the liquid stream can leave the system as the product stream 81, which can comprise ethanol and water. The product stream 81 can be fed to a dehydration unit to produce a dehydrated ethanol stream, which can then be recycled back to column 70 as feed (e.g., as part of feed stream 80). A remaining portion of the liquid stream can be returned to the column 70 as reflux. A portion of the bottom draw is taken out as the product stream 92, while the remaining portion is passed through reboiler 90 to be recycled to the column 70. In an embodiment, the bottom draw may be passed through a reboiler (e.g., similar to reboiler 90) and optionally passed to a separator where the vapor portion may pass to the column 70 while at least a portion of the remainder is taken out as the butyl acetate product stream 92. The stream passing through the reboiler 90 provides the evaporation effect and vapor flow for operating the column 70. The product stream 92 may comprise the butyl acetate produced in the column potentially along with any byproducts produced by the reaction. Subsequent purification of product stream 92 comprising butyl acetate may be needed to remove the hydrogenated byproducts from the butyl acetate, e.g., using a separator such as that as shown in FIG. 2 as separator 32, which in an embodiment may comprise a distillation column.

In an embodiment, the column 70 may operate at any of the conditions (e.g., operating pressure, operating temperature, etc.) discussed herein with respect to column 10 in FIG. 1(*b*). In addition, the column 70 may have any number of stages, and in an embodiment the column 70 may have any number of stages as described with respect to column 10 in FIG. 1(*b*).

In the dual feed systems described above with respect to FIGS. 3 and 4, the hydrogen feed should be at a sufficiently low level that it does not significantly adversely affect the dehydration of the ethanol in the zone above, while being effective to hydrogenate the undesirable byproducts. Feed rates of hydrogen can be adjusted empirically to optimize this balance. Commonly, the ratio of the ethanol:hydrogen can be in a range of about 500:1 to 1:1 molar ratio, more commonly about 500:1 to 10:1 or 500:1 to 100:1.

In an embodiment, one or more side reactors can be connected to a reactive distillation column to increase the catalyst holdup for improved reactant conversion. In the side reactor embodiment, the side reactor feed is withdrawn from the distillation column and the reactor effluent is returned back to the same column. An adequate amount of catalyst may be arranged in a side reactor system where traditional reactor types and catalyst structures can be used. Also, the reaction conditions within the side reactor such as temperature can be adjusted independently of those prevailing in the distillation column by appropriate heat exchange. Further, the flow rates of the side reactors can be selectively controlled to provide a desired space velocity through the side reactor. In some embodiments, the reaction may occur within the side reactors over a catalyst, and a catalyst may not be present within the distillation column.

Figure 5A:
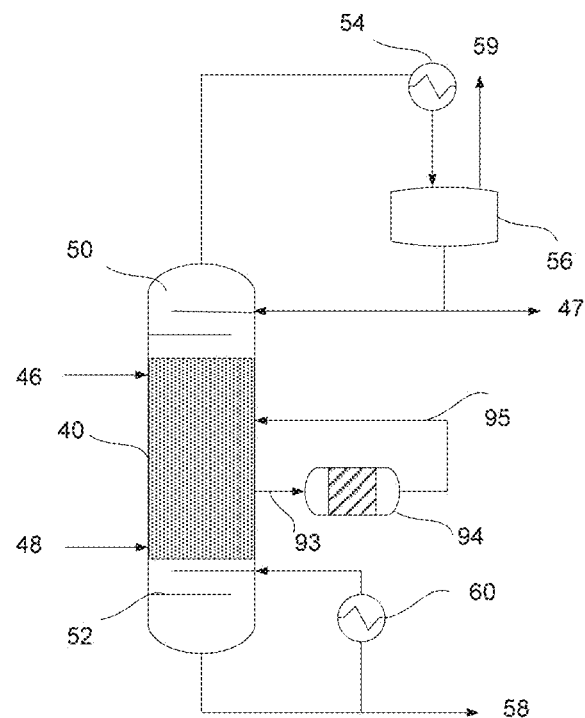
FIGS. 5(a) and 5(b) show a simplified schematic of a reactive distillation system according to an embodiment.
Figure 5B:
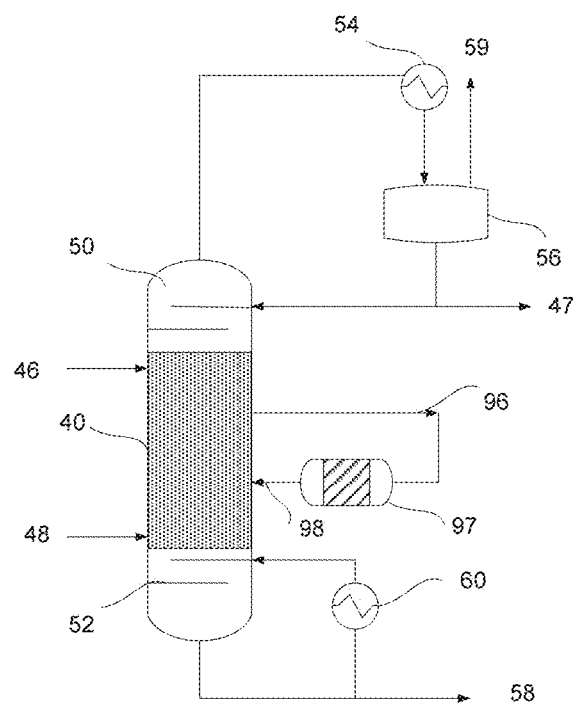

Schematics for a side reactor reactive distillation column with a conversion catalyst are shown in FIGS. 5(*a*) and 5(*b*). A single side reactor is shown in FIGS. 5(*a*) and 5(*b*), however, multiple side reactors can be used along the length of the reactive distillation column. FIG. 5(*a*) shows a configuration where the feed stream 93 to the side reactor 94 is bottom up and vapor phase. In an embodiment, the ethanol and/or the ethyl acetate and butanol may react over the catalyst within the side reactor 94 in the vapor phase. The outlet from side reactor 94 is stream 95 which is sent back to the distillation column 40 at any location in the column 40 above the location of feed stream 93. FIG. 5(*b*) shows a configuration where the feed stream 96 to the side reactor 97 is top down and liquid phase. In an embodiment, the ethanol and/or the ethyl acetate and butanol may react over the catalyst within the side reactor 97 in the liquid phase. The outlet from side reactor 97 is stream 98 which is sent back to the distillation column 40 at any location in the column 40 below the location of feed stream 96. The side reactors 94 and 97 each contain one or more conversion catalyst for converting ethanol to ethyl acetate and butanol and/or converting the ethyl acetate and butanol to butyl acetate and ethanol. Examples of suitable conversion catalysts are described in more detail herein. In some embodiments, only one or more of the side reactors may comprise a catalyst, and there may not be a catalyst located within the reactive distillation column 40.

The use of a side reactor using a liquid feed may allow for the reaction to occur in the liquid phase. While not intending to be limited by theory, it is believed that the dehydration of ethanol to produce a butanol and/or ethyl acetate may occur over the conversion catalysts described herein in the liquid phase. The use of a liquid phase reaction may allow for reactive distillation to be effectively used for converting the ethanol into butanol and/or ethyl acetate, and/or producing butyl acetate from the butanol and ethyl acetate.

While illustrated as a bottom up vapor phase design and a top down liquid phase design in FIGS. 5(*a*) and 5(*b*), the side reactors 94, 97 may also operate bottom up using a liquid phase draw from the column 40 and top down using a vapor phase draw from the column with the appropriate equipment such as pumps, compressors, valves, piping, etc. In an embodiment, the side reactors 94, 97 may be implemented as a single reactor vessel, or as a plurality of reactor vessels arranged in series and/or parallel. In an embodiment, a plurality of side reactors may be implemented as shown in FIGS. 5(*a*) and 5(*b*) along the length of the column as needed. In addition, when both the column 40 and the side reactor 94 comprise catalysts, the conversion catalyst in both the column 40 and the side reactor 94 may convert ethanol into ethyl acetate and butanol and/or convert ethyl acetate and butanol into butyl acetate and ethanol, though the specific conversion catalysts (e.g., catalyst compositions, catalyst forms, catalyst component loadings, or any combination thereof) in each of the column 40 and the side reactor 94, 97 may be the same or different. Suitable conversion catalysts for converting the ethanol into butyl acetate may be selected based on the expected operating conditions, which may vary between the column 40 and the side reactor 94, 97. In some embodiments, the product selection can be tuned through the use of the catalyst selection in the column 40 and the side reactor 94, 97. For example, the conversion catalyst in the column 40 may be configured to produce ethyl acetate and/or butanol, and the conversion catalyst in the side reactor 94, 97 may be configured to produce butyl acetate. By controlling the flow of the fluids within the column, the product distribution can be tuned to produce ethyl acetate, butanol, and/or butyl acetate. In some embodiments, the production of butanol may result in the production of butyl acetate, and by controlling the flows and conditions in the side reactors and the column, the product distribution between ethyl acetate and butyl acetate can be controlled to produce a desired ratio.

Schematics for a side reactor reactive distillation with two feeds and using two catalyst zones are shown in FIG. 6. In this embodiment, an upper feed 80 of ethanol may be fed to the upper catalyst zone, and a lower feed 82 of hydrogen may be fed to the lower catalyst zone. A single side reactor is shown for each catalyst zone in the reactive distillation column 70, however, multiple side reactors along the length of the reactive distillation column 70 can be used for each catalyst zone. FIG. 6(*a*) shows a configuration where the top zone feed stream 99 to the side reactor 100 is bottom up and vapor phase. The bottom zone feed stream 102 to another side reactor 103 is also bottom up and vapor phase. The outlet from side reactor 100 is stream 101 which is sent back to the distillation column at any location in the column above the location of feed stream 99. The outlet from side reactor 103 is stream 104 which is sent back to the distillation column at any location in the column above the location of feed stream 102.

FIG. 6(*b*) shows a configuration where the top zone feed stream 105 to the side reactor 106 is top down and liquid phase. The bottom zone feed stream 108 to another side reactor 109 is also top down and liquid phase. The outlet from side reactor 106 is stream 107 which is sent back to the distillation column at any location in the column below the location of feed stream 105. The outlet from side reactor 109 is stream 110 which is sent back to the distillation column at any location in the column below the location of feed stream 108. Examples of suitable catalysts for side reactors 100 and 106 may include any of the conversion catalysts described in more detail herein. Examples of hydrogenation catalysts for side reactors 103 and 109 include any of the hydrogenation catalysts described in more detail herein. In some embodiments, one or more of the side reactors may comprise a catalyst, and there may not be a catalyst located within the reactive distillation column.

Figure 6A:
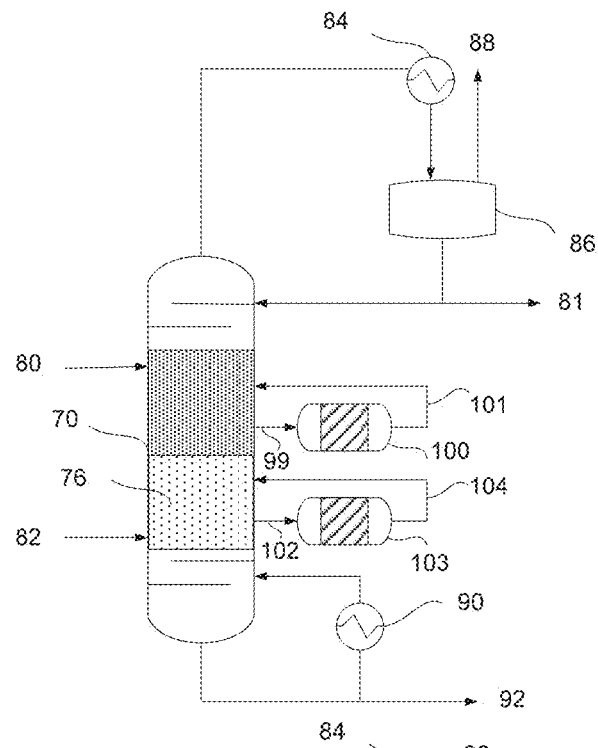
FIGS. 6(a) and 6(b) show a simplified schematic of a reactive distillation system according to another embodiment.
Figure 6B:
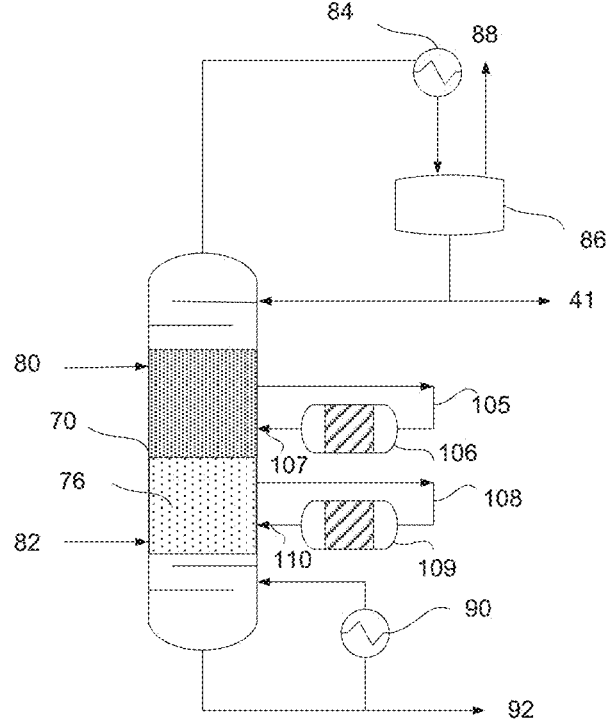

While illustrated as a bottom up vapor phase design and a top down liquid phase design in FIGS. 6(a) and 6(b), the side reactors 100, 103, 106, 109 may also operate bottom up using a liquid phase draw from the column 70 and top down using a vapor phase draw from the column 70 with the appropriate equipment such as pumps, compressors, valves, piping, etc. In an embodiment, the side reactors 100, 103, 106, 109 may be implemented as a single reactor vessel, or as a plurality of reactor vessels arranged in series and/or parallel. In an embodiment, a plurality of side reactors may be implemented as shown in FIGS. 6(a) and 6(b) along the length of the column as needed. In addition, the respective conversion catalysts in both the column 70 and the side reactors 100, 106 may convert a feed comprising ethanol into ethyl acetate and butanol and/or convert ethyl acetate and butanol to butyl acetate and ethanol, though the specific conversion catalysts (e.g., catalyst compositions, catalyst forms, catalyst component loadings, or any combination thereof) in each of the column 40 and the side reactors 100, 106 may be the same or different. A suitable conversion catalyst for converting ethanol into ethyl acetate and butanol and/or converting ethyl acetate and butanol to butyl acetate and ethanol may be selected based on the expected operating conditions, which may vary between the column 40 and the side reactors 100, 106. Similarly, the respective catalysts in both the column 70 and the side reactors 103, 109 may comprise hydrogenation catalysts, though the specific catalysts (e.g., catalyst compositions, catalyst forms, catalyst component loadings, or any combination thereof) in each of the column 70 and the side reactors 103, 109 may be the same or different. Suitable hydrogenation catalysts may be selected based on the expected operating conditions, which may vary between the column 70 and the side reactors 100, 106. In some embodiments, the respective catalysts in the side reactors 103, 109 may comprise a conversion catalyst for converting ethanol into ethyl acetate and butanol and/or converting ethyl acetate and butanol to butyl acetate and ethanol.

In the reactive distillation systems of FIGS. 5(a), 5(b), 6(a), and 6(b), the composition of product stream 58, 92 may be adjusted by controlling the flow rate between the reactive distillation column 40, 70 and the side reactors 94, 97, 100, 103, 106, 109. In an embodiment, a system for the production of butyl acetate, ethyl acetate, and/or butanol comprises a reactive distillation column 40, 70 and one or more side reactors 94, 97, 100, 106 charged with one or more conversion catalysts. The reactive distillation column 40, 70 can be optionally charged with one or more conversion catalysts. During continuous operation, flow rates 93/95, 96/98, 99/101, 105/107 between the column 40, 70 and the one or more side reactors 94, 97, 100, 106 may be adjusted to achieve a desired composition of the product stream 58, 92. In an embodiment, the flow rates 93/95, 96/98, 99/101, 105/107 between the column 40, 70 and the one or more side reactors 94, 97, 100, 106 can be adjusted to balance the molar production of ethyl acetate and butanol. The resulting product streams can then react in a side reactor or the reactive distillation column to produce butyl acetate. In an embodiment, adjustments to the flow rates 93/95, 96/98, 99/101, 105/107 may be made by a control system.

As a general proposition, the number of side reactors and the type of catalyst with which the column and each side reactor are individually charged can be selected to accommodate a desired variety of feedstocks, a desired range of product compositions, or a combination thereof during operation of the reactive distillation column. During continuous operation, the flow rates between the side reactors and the column can be adjusted (e.g., selectively tuned) to respond to changes in feedstock, to achieve a desired product composition, or a combination thereof. The ability to adjust the flow rates between the side reactors and the column advantageously allows feedstocks to be changed when market fluctuations in price and availability favor the use of a feedstock having a different composition (e.g. lower quality, higher water content, etc.). The ability to adjust the flow rates between the side reactors and the column advantageously allows feed quality to be maintained despite fluctuations in feedstock composition during continuous operation. The ability to adjust and/or control the flow rates between the side reactors and the column may also allow for the reduction or elimination of undesirable byproducts to advantageously increase the purity of the desired products.

While described in the context of reactive distillation, the production of butyl acetate can also proceed by introducing ethyl acetate and butanol into a reactor such as a fixed bed reactor comprising a conversion catalyst. The ethyl acetate and butanol can react within the reactor to produce butyl acetate and ethanol. The ethanol can be separated from the product stream to produce a butyl acetate product. Any unreacted reactants can be separated and recycled to the inlet of the reactor for further reaction.

Figure 7:
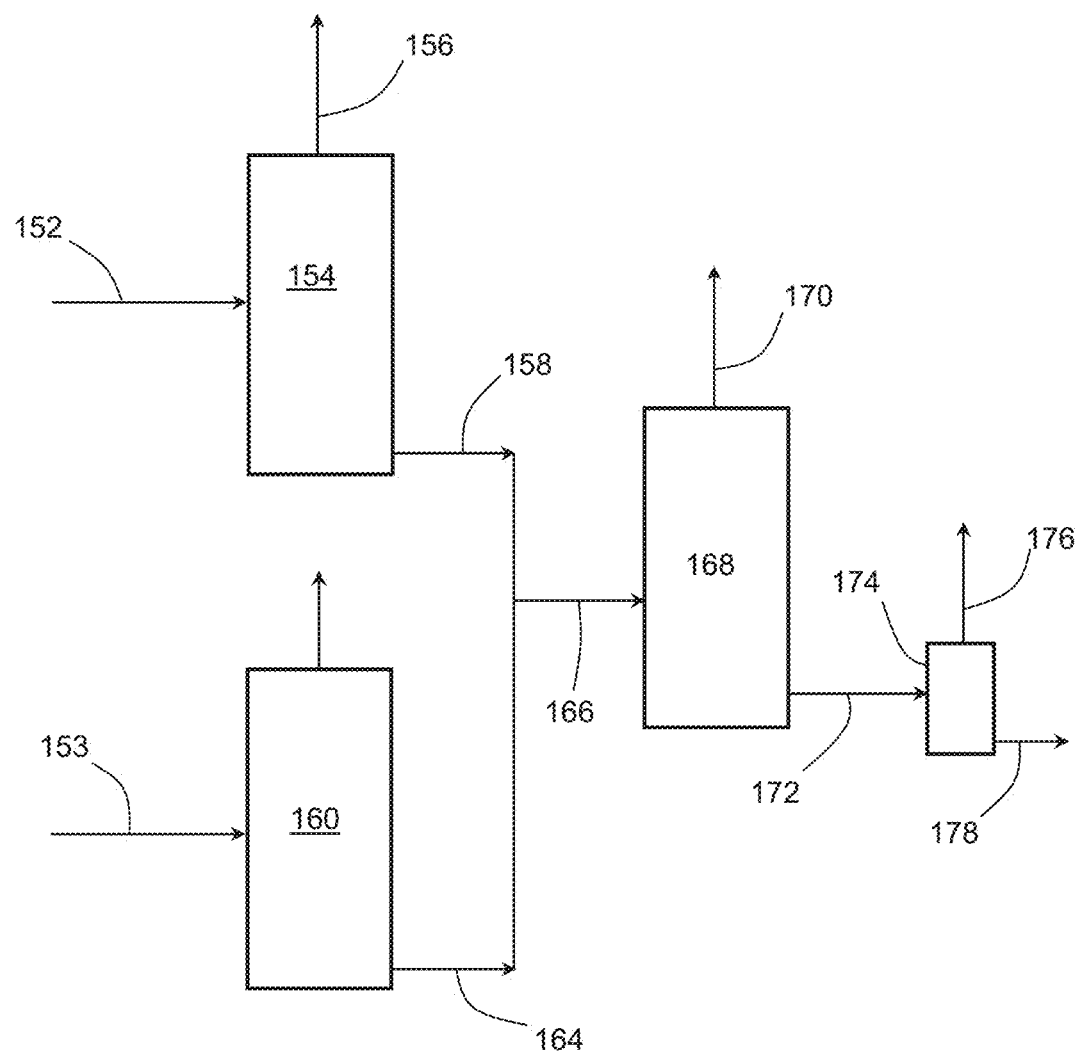
FIG. 7 shows a simplified schematic of a multi-reactor system according to an embodiment.

In some embodiments, separate reactor units can be used to produce ethyl acetate and butanol, which can then be separated and combined in a third reactor unit to produce butyl acetate. FIG. 7 illustrates an embodiment of this type of system. In this configuration, ethanol can be fed to a first reactor unit 154 in an inlet stream 152. The reactor unit 154 can include any suitable reactor such as a fixed bed reactor having a separator such as a distillation column downstream of the reactor. In some embodiments, the reactor unit 154 can comprise a reactive distillation unit as described with respect to any of FIGS. 1(a) to 6(b). The ethanol can be converted to ethyl acetate, hydrogen, and water in the reactor unit 154. The hydrogen and water can leave as a single or combined product stream 156. The resulting ethyl acetate stream 158 can be passed to a downstream reactor to product butyl acetate.

Similarly, ethanol can be fed to a second reactor unit 160 in an inlet stream 153. The reactor unit 160 can include any suitable reactor such as a fixed bed reactor having a separator such as a distillation column downstream of the reactor. In some embodiments, the second reactor unit 160 can comprise a reactive distillation unit as described with respect to any of FIGS. 1(a) to 6(b). The ethanol can be converted to butanol, hydrogen, water, and potential a number of byproducts in the reactor unit 160. The hydrogen, water, and byproducts can leave as a single or combined product stream 162. The resulting butanol stream 164 can be passed to a downstream reactor to product butyl acetate.

The ethyl acetate stream 158 from the reactor unit 154 can be combined with the butanol stream 164 from the second reactor unit 160 and reacted in the presence of a catalyst in a third reactor unit 168. The resulting reaction product can include hydrogen, water, ethanol, and the product butyl acetate. The hydrogen, water, and ethanol can leave individual product streams or a single product stream 170. The ethanol can be further separated and recycled to the inlet of the reactor unit 154 and/or the second reactor unit 160 to further produce reactants for the butyl acetate reaction. The butyl acetate stream 172 can be further separated as needed to create a butyl acetate stream 178 having a desired purity. Any components in the butyl acetate stream 172 from the third reactor unit 168 can leave as product stream 176.

Figure 8:
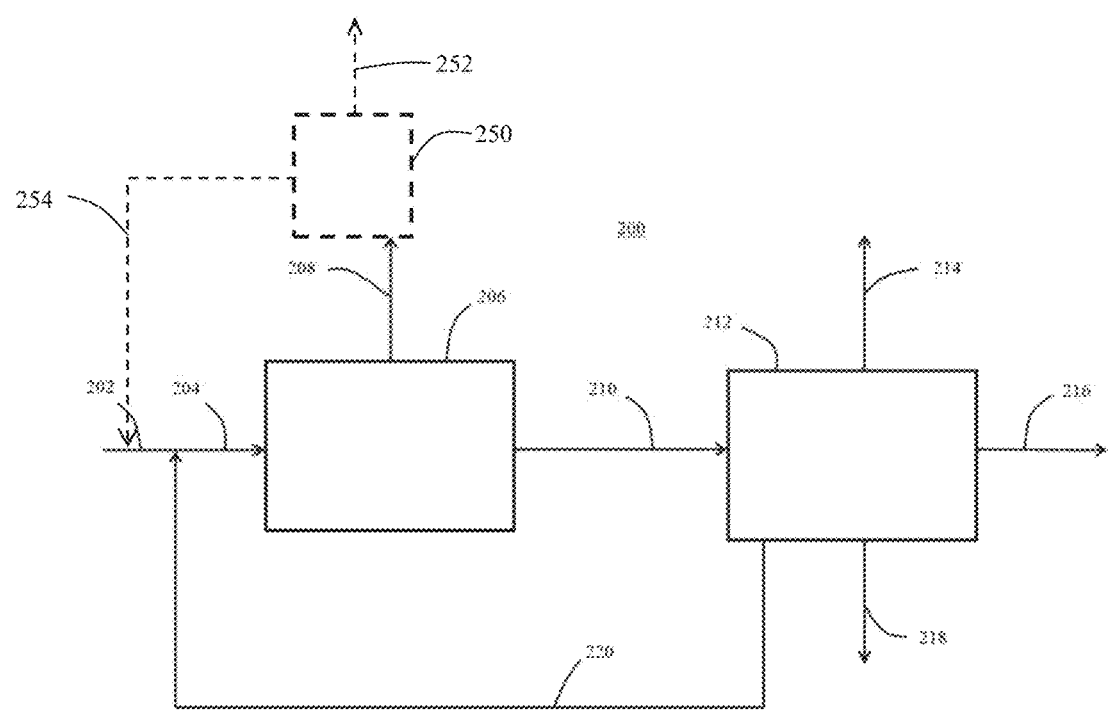
FIG. 8 illustrates a schematic flow diagram of a reactive distillation system with a recycle according to an embodiment.

As schematically illustrated in FIG. 8, a butyl acetate production process may comprise a products separation section 212 for use in separating the product stream and allowing at least a portion of any unreacted ethanol and/or ethyl acetate/butanol to be recycled to the inlet of the process. The products separation section may be configured to provide at least one product stream comprising a single reaction product such as ethanol, butanol, ethyl acetate, butyl acetate, or another reaction product having a purity of greater than about 90%, greater than about 95%, greater than about 96%, greater than about 97%, greater than about 98%, greater than about 99%, or greater than about 99.5% by weight. In an embodiment, a separation train may be used to produce a plurality of streams that each predominately comprise a single reaction product such as ethanol, butanol, ethyl acetate, butyl acetate, or another reaction product having a purity of greater than about 90%, greater than about 95%, greater than about 96%, greater than about 97%, greater than about 98%, greater than about 99%, or greater than about 99.5% by weight. At least one additional stream may be produced comprising the remaining components of the product stream from the reactive distillation column. In an embodiment, a plurality of streams are produced in the separation section comprising a stream predominantly comprising butanol, a stream predominantly comprising ethyl acetate, a stream comprising water, a stream comprising ethanol, a stream comprising butyl acetate, a heavies stream comprising one or more reaction products with boiling points above the boiling point of butyl acetate, or any combination thereof. In an embodiment, one or more streams comprising ethanol, ethyl acetate, and/or butanol, if present, may be recycled to the reactive distillation column.

As schematically illustrated in FIG. 8, a system 200 for producing butyl acetate may comprise a feed stream 202 comprising ethanol that may be optionally combined with a recycle stream 220 comprising ethanol to form the inlet stream 204 to the reactive distillation system 206. The system 200 may be useful for embodiments in which there is an incomplete conversion of the ethanol and/or an incomplete conversion of the intermediate reactants ethyl acetate and butanol to butyl acetate in the reactive distillation system 206. While illustrated as being combined prior to introduction to the reactive distillation system 206, the feed stream 202 and the recycle stream 220 may be fed individually to the reactive distillation system 206. In an embodiment, the reactive distillation system 206 may comprise any of the reactive distillation systems described with respect to FIGS. 1-7 herein. The reactive distillation system 206 may produce an overhead product stream 208 and a bottoms product stream 210. The overhead product stream 208 may comprise water, hydrogen, unreacted ethanol, potentially ethyl acetate and/or butanol, or any combination thereof and may generally correspond to any of the streams 11, 47, and/or 81 as illustrated in FIGS. 1-7. Similarly, the bottoms product stream 210 may comprise butyl acetate, ethyl acetate, ethyl butyrate, 2-pentanone, propanol, additional reaction products, possibly water, and/or any combination thereof. In an embodiment, the bottoms product stream 210 may correspond to any of the streams 22, 36, 58, and/or 92 as illustrated in FIGS. 1-7.

An optional overhead separation section 250 may receive the overhead product stream 208 from the reactive distillation system 206. The overhead separation section 250 may be configured to separate water from any ethanol in the overhead product stream 208, which may be present at a water-alcohol azeotrope such as a water-ethanol azeotrope, to allow the feed ethanol to be recycled to the system while removing the water to drive the reaction within the reactive distillation system 206. The overhead separation section 250 may comprise any number or type of separation units, which may employ pressure- and/or temperature-swing distillation, pressure- and/or temperature-swing adsorption, membrane-based separation, molecular sieve separation, any other suitable separation technology, or any combination thereof, all of which may be used to remove a desired amount of water from the overhead product stream 208. The overhead separation section 250 may produce a recycle stream 254 comprising ethanol and an outlet stream 252 comprising water. The recycle stream 254 may comprise the ethanol for use as a feed for the reactive distillation system 206. In some embodiments, the recycle stream 254 may not be recycled to the reactive distillation system, but rather may exit the system 200 as a separate product stream. While illustrated as being combined prior to introduction to the reactive distillation system 206, the feed stream 202 and the recycle stream 254 (as well as recycle stream 220) may be fed individually to the reactive distillation system 206.

A products separation section 212 may receive the bottoms product stream 210 from the reactive distillation system 206, and, in some embodiments, the overhead product stream 208. The products separation section 212 may comprise any number or type of separation units, which may employ pressure- and/or temperature-swing distillation, pressure- and/or temperature-swing adsorption, membrane-based separation, cryogenic distillation, any other suitable separation technology, or any combination thereof, all of which may be used to generate a desired product distribution. The products separation section 212 may generally produce one or more product streams such as product stream 216. The butyl acetate product stream 216 may comprise butyl acetate having a purity of greater than about 90%, greater than about 95%, greater than about 96%, greater than about 97%, greater than about 98%, greater than about 99%, or greater than about 99.5% by weight. In addition to the butyl acetate product stream 216, one or more additional streams may be produced by the products separation section 212. In an embodiment, a lights product stream 214 may be produced. The lights product stream 214 may comprise water, ethanol, ethyl acetate, other light components, or any combination thereof. In an embodiment, a heavies product stream 218 may comprise one or more reaction products (e.g., one or more aldehydes, ketones, heavy alcohols, any combination thereof, etc.). In an embodiment, a recycle stream 220 may be produced. The recycle stream may comprise ethanol for use as a feed for the reactive distillation system 206. In some embodiments, the ethanol stream may not be recycled to the reactive distillation system, but rather may exit the system 200 as a separate product stream. Each of the potential product streams 214, 216, 218, and/or 220 may exit the system as separate product stream and/or exit the system 200 for use as fuel and/or as a feed to additional downstream processes. While illustrated as separate streams 214, 216, 218, and/or 220, one or more of these streams may exit the system 200 as a combined product stream.

The butyl acetate production process may produce a variety of products. For example, the process may produce one or more alcohols such as butanol, propanol, 1-hexanol, 1-octanol, 2-ethyl-1-butanol, 2-ethyl-1-hexanol, butanediol, and heavier alcohols. The process may also produce various additional products such as ethyl acetate, ethyl butyrate, 2-pentanone, propanol, and/or water. Various side products may also be produced that can result in a complex mixture of components that can be difficult to separate. This complex mixture may exhibit a number of binary azeotropes, ternary azeotropes, and possibly azeotropes containing four or more components. Some of the azeotropes can be homogeneous, while others can be heterogeneous. These azeotropes can give rise to distillation boundaries in the composition space that, along with the azeotropes, act as barriers for distillation and limit the ability to achieve high recovery and/or purity of the desired products using distillation alone. When water is present in a sufficient amount, the system may also comprise a multiple liquid phase region, with vapor-liquid-liquid and/or liquid-liquid equilibrium tie-lines that cross some of these boundaries. In some embodiments, a product separation system can exploit this characteristic of the system and comprise a separation sequence comprising distillation columns and decanters. This system may be capable of producing one or more high purity product streams such as a high purity butyl acetate stream, and potentially one or more other valuable byproduct streams.

Figure 9:
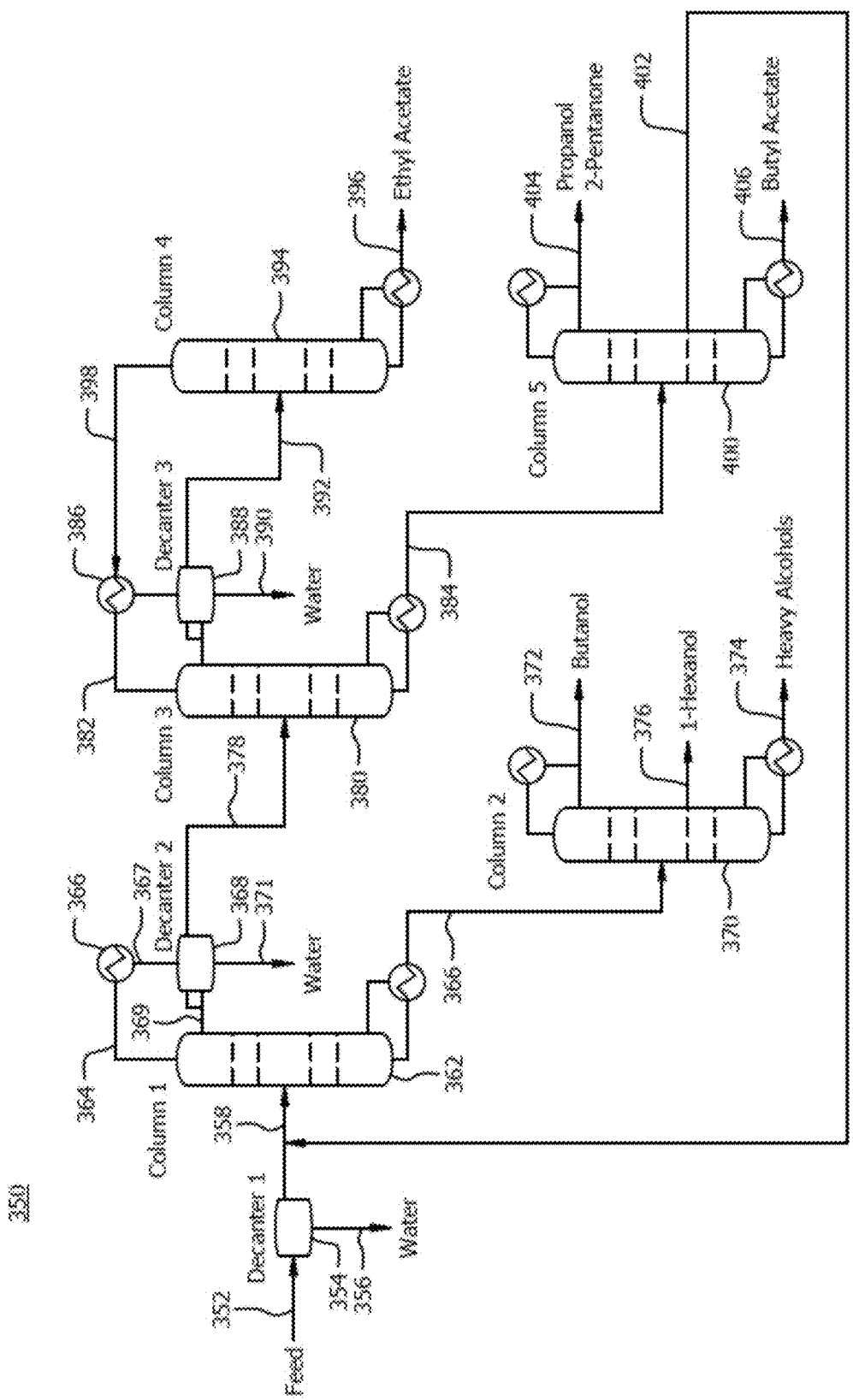
FIG. 9 illustrates a schematic flow diagram of a product separation system according to an embodiment.

Various separation schemes can then be used to separate a complex mixture such as the product stream from the reactive distillation process described herein. An embodiment of a separation scheme 350 for separating the components of a complex mixture is illustrated in FIG. 9. In this embodiment, the separation sequence may be used to recover one or more high purity product streams such as a butyl acetate stream, an ethyl acetate stream, and optionally one or more other valuable byproduct streams. In this embodiment, an inlet stream 352 may first be passed to a decanter 354. In an embodiment, the inlet stream 352 may be the product stream from any of the reactive distillation processes described herein. The inlet stream 352 may comprise a number of components including any of the products produced in the reactive distillation process described herein. In an embodiment, the inlet stream 352 to the separation sequence 350 comprises butyl acetate, one or more alcohols (e.g., propanol, butanol, 1-hexanol, 1-octanol, 2-ethyl-1-butanol, 2-ethyl-1-hexanol, butanediol, octanol, decanol, dodecanol, and heavier alcohols, etc.), ethyl acetate, ethyl butyrate, 2-pentanone, and possibly water. The inlet stream 352 can be passed through an optional inlet decanter 354 to remove any excess water that forms a separate liquid phase. The resulting water stream 356 comprising water and relatively minor amounts of dissolved organics can be passed out of the decanter 354 and discharged from the process. When the decanter 354 is used, the decanter 354 may be operated close to the bubble point of the inlet stream 352 mixture in order to minimize the amount of dissolved organics such as propanol and/or butanol in the aqueous phase.

The organic phase can exit the decanter 354 as liquid stream 358. The liquid stream 358 may be combined with a recycle stream 360 and the combined stream can be fed to a first distillation column 362. The first distillation column 362 may comprise any of the types of distillation columns described herein, and the first distillation column 362 may operate at a pressure ranging from about 0.1 atm to about 80 atm, or about 0.5 atm to about 40 atm. The first distillation column 362 may produce an overhead stream 364 and a bottoms stream 366. A portion of the bottoms stream 366 may pass through an exchanger to provide a vapor feed to the column 362, and the remaining portion may comprise one or more alcohols such as butanol, 1-hexanol, and/or the other higher alcohols.

The bottoms stream 366 from the first distillation column 362 can be further separated using one or more distillation columns to recover one or more high purity product streams. In an embodiment, the product streams can include product streams predominately comprising a single alcohol. For example, a further separation may produce product streams predominately comprising butanol and/or possibly 1-hexanol, and the remaining heavy alcohols can be produced individually or as a combined stream. In the embodiment shown in FIG. 9, the bottoms stream 366 can pass to a second distillation column 370, which is optional in some embodiments. The second distillation column 370 may comprise any of the types of distillation columns described herein, and the second distillation column 370 may operate at a pressure ranging from about 0.1 atm to about 80 atm, or about 0.5 atm to about 40 atm. The second distillation column 370 may produce a plurality of product streams. In an embodiment, the second distillation column 370 may produce a butanol product stream 372 as the overhead product, an intermediate side stream 376 predominately comprising hexanol, and a bottoms stream comprising one or more alcohols having a boiling point higher than that of hexanol (e.g., 1-hexanol). In an embodiment, the butanol recovered in the butanol product stream 372 may have a purity of greater than about 90%, greater than about 95%, greater than about 96%, greater than about 97%, greater than about 98%, greater than about 99%, or greater than about 99.5% butanol by weight. In some embodiments, one or more additional distillation columns may be combined with the first distillation column 362, and/or used to further purify the product streams from the second distillation column 370. For example, a further distillation column could be used to further separate out individual components of the bottoms product stream 374 from the second distillation column 370. In any of these columns, the desired products may be recovered as one or more side streams. In some embodiments, side rectifier or side stripper columns may also be used with the first distillation column 362 and/or the second distillation column 370 to improve the purity of the side stream products. In some embodiments, distillation column 370 may not be present when the butanol content of the feed stream to the separation section 350 is relatively low and/or when separation of the butanol is not desired. In this embodiment, the bottoms stream 366 from the first distillation column 362 can leave the system for various downstream uses and/or be used as fuel within the system.

The overhead stream 364 from the first distillation column 362 may pass through a heat exchanger 366 to at least partially condense the overhead stream 364. The heat exchanger 368 may comprise any of the heat exchanger types described herein. The at least partially condensed stream 367 may pass to a decanter 368. In some embodiments, the decanter 368 may comprise a series of decanters operating at the same or different temperatures. The decanter(s) 368 may generate an aqueous stream and an organic stream. A fraction of the organic stream, and possibly a fraction of the aqueous stream, can be refluxed to the first distillation column 362. For example, the stream 369 may comprise a portion of the organic stream, and optionally, a portion of the aqueous stream. The remainder of the aqueous stream 369, which may comprise water with a relatively small amount of dissolved organics, may be recovered and discharged from the system. As noted above, the presence of water may be important in facilitating the separation of two or more of the organic components in the inlet stream 352. Consequently, a fraction of the aqueous stream 369 may also be recycled to either the first distillation column 362 and/or to the inlet stream 352 of the separation system 350, and/or combined stream 358. Additional water may be added to the first distillation column 362 and/or the inlet stream 352 or the combined stream 358 to facilitate the separation. The organic product stream 378 from the decanter 368 may comprise the butyl acetate, ethyl acetate, one or more alcohols, ethyl butyrate, and potentially other side products. The organic product stream 378 may also comprise water.

A number of alternative separation sequences may be used to recover the butyl acetated, any ethyl acetate, and any butanol in the organic product stream 378. In the embodiment illustrated in FIG. 10, the organic product stream 378 can be sent to a distillation sequence comprising a decanter 388. The organic product stream 378 may first pass to a third distillation column 380. The third distillation column 380 may comprise any of the types of distillation columns described herein, and the third distillation column 380 may operate at a pressure ranging from about 0.1 atm to about 80 atm, or about 0.5 atm to about 40 atm. The third distillation column 380 may produce an overhead stream 382 and a bottoms stream 384.

The overhead stream 382 from the third distillation column 380 can be condensed in a heat exchanger 386 to at least partially condense the overhead stream 382. The heat exchanger 386 may comprise any of the heat exchanger types described herein. The at least partially condensed stream may pass a decanter 388, or possibly a series of decanter operating at the same or different temperatures. The decanter 388 may produce at least an organic phase stream and an aqueous phase stream. At least a portion of the organic phase stream, and also possibly a fraction of the aqueous phase, can be refluxed to the third distillation column 380. The remainder of the aqueous phase stream 390, which may comprise water with a relatively minor amount of dissolved organics, can be recovered and discharged from the system. The remainder of the organic phase stream 392, which can comprise organics including, but not limited to, ethyl acetate in addition to a minor amount of water, can be further separated to recover high purity ethyl acetate. In some embodiments, the organic phase stream 392 can be recycled to one or more reactors as a reactant.

Figure 10:
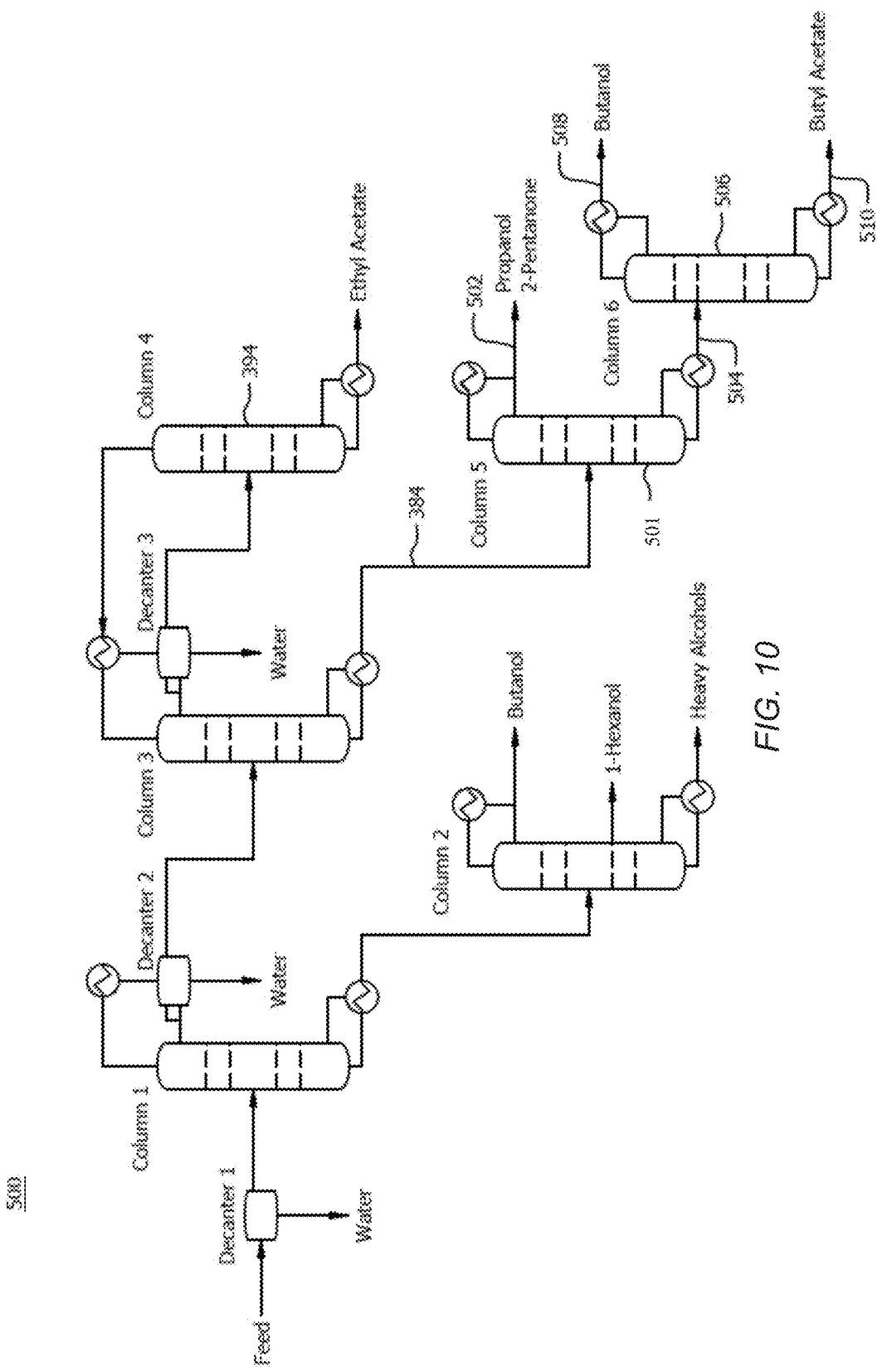
FIG. 10 illustrates a schematic flow diagram of a product separation system according to another embodiment.

The separation of the organic phase stream 392 may be achieved using a single distillation column (e.g., a fourth distillation column 394) as shown in FIG. 10. The fourth distillation column 394 may comprise any of the types of distillation columns described herein, and the fourth distillation column 394 may operate at a pressure ranging from about 0.1 atm to about 80 atm, or about 0.5 atm to about 40 atm. The fourth distillation column 394 may produce an overhead stream 398 and a bottoms stream 396. The bottoms stream 396 can comprise high purity ethyl acetate. In an embodiment, the ethyl acetate recovered in the bottoms stream may have a purity of greater than about 90%, greater than about 95%, greater than about 96%, greater than about 97%, greater than about 98%, greater than about 99%, or greater than about 99.5% ethyl acetate by weight. The overhead stream 398 can be passed to the heat exchanger 386, where at least a portion of the overhead stream 398 can be condensed and passed to at least one of the decanter 388 and/or the third distillation column 380.

The bottoms stream 384 from the third distillation column 380 can be passed to a fifth distillation column 400. The fifth distillation column 400 can be operated to produce a bottoms stream 406 comprising high purity butyl acetate. Additional product streams can comprise a mixture of organics, which can include, but is not limited to, ethyl butyrate, propanol, 2-pentanone, butanol, and/or ethyl butyrate. The fifth distillation column 400 may comprise any of the types of distillation columns described herein, and the fifth distillation column 400 may operate at a pressure ranging from about 0.1 atm to about 80 atm, or about 0.5 atm to about 40 atm. The fifth distillation column 400 may produce a plurality of streams comprising an overhead stream 404, a bottoms stream 406, and/or one or more side product streams 402. The bottoms stream 406 may comprise butyl acetate. The overhead stream may comprise propanol and/or 2-pentanone. The side product stream 402 may primarily comprise butanol, butyl acetate, and/or ethyl butyrate. The side product stream 402 can be recycled to the first distillation column 362, the feed 352, the combined stream 358, and/or to the decanter 368. In some embodiments, the fourth distillation column 394 and the fifth distillation column 400 may be combined into a single column operating at a pressure greater than about 3 atm, and the butanol can be recovered as a side product with an optional side rectifier used to improve the purity of the butanol product. In some embodiments, the ethyl acetate in stream 396 and/or the butanol in stream 372 can be recycled to the inlet of a reactive distillation column for the further product of butyl acetate.

Another embodiment of a separation process 500 is illustrated in FIG. 10. The separation process 500 is similar to the separation process 350 illustrated in FIG. 9 with the exception that the bottoms product stream 384 from the third distillation column 380 may pass to a different series of separation units. The remaining components of the separation process 500 may be the same or similar to those described with respect to FIG. 9, and the similar components will not be described with respect to FIG. 10 in the interest of brevity. In this embodiment, the bottoms stream 384 can pass to a fifth distillation column 501, which may be optional in some embodiments. The fifth distillation column 501 may comprise any of the types of distillation columns described herein, and the fifth distillation column 501 may operate at a pressure ranging from about 0.1 atm to about 80 atm, or about 0.5 atm to about 40 atm. The fifth distillation column 501 may produce an overhead stream 502 and a bottoms stream 504. The overhead stream 502 may comprise propanol and/or 2-pentanone. In some embodiments, the fifth distillation column 501 may not be present when the propanol/pentanone content of the product mixture is relatively low and/or when separation of the propanol/pentanone is not desired. In this embodiment, the bottoms product stream 384 from the third distillation column 380 can pass directly to the sixth distillation column 506.

The bottoms stream 504 from the fifth distillation column 501 can comprise butanol, ethyl butyrate, and/or butyl acetate, and the bottoms stream 504 can pass to a sixth distillation column 506, which may operate at a pressure of greater that about 3 atm. The sixth distillation column 506 may comprise any of the types of distillation columns described herein, and the sixth distillation column 506 may operate at a pressure ranging from about 3 atm to about 80 atm. In general, a butanol-butyl acetate azeotrope may limit the purity of any butanol recovered using distillation in a mixture of butanol and butyl acetate. However, the azeotrope is pressure sensitive and is not present at a pressure greater than about 3 atm. Operating the sixth distillation column at a pressure greater than about 3 atm can allow the overhead stream to comprise high purity butanol and the bottoms stream to comprise high purity butyl acetate. In an embodiment, the butanol recovered in the overhead stream 508 may have a purity of greater than about 90%, greater than about 95%, greater than about 96%, greater than about 97%, greater than about 98%, greater than about 99%, or greater than about 99.5% butanol by weight. The bottoms stream 510 may comprise butyl acetate In an embodiment, the butyl acetate recovered in the bottoms stream 510 may have a purity of greater than about 90%, greater than about 95%, greater than about 96%, greater than about 97%, greater than about 98%, greater than about 99%, or greater than about 99.5% butyl acetate by weight. As noted above, the fourth distillation column 394 and the fifth distillation column 501 may be combined into a single column operating at a pressure greater than about 3 atm, and the butyl acetate can be recovered as a bottoms product.

Figure 11:
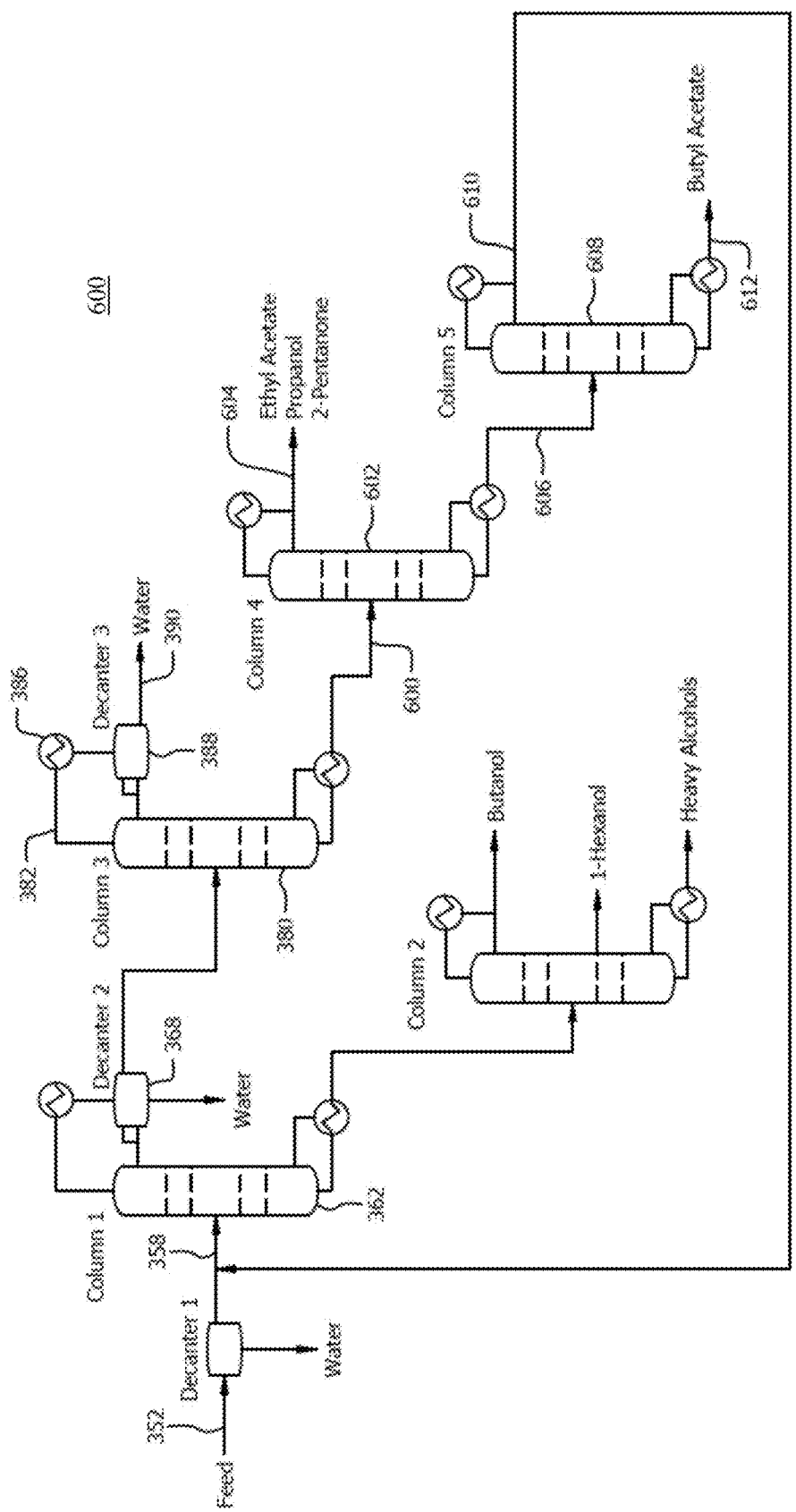
FIG. 11 illustrates a schematic flow diagram of a product separation system according to still another embodiment.

Another embodiment of a separation process 600 is illustrated in FIG. 11 for recovering various product streams such as butyl acetate from the organic phase stream from the decanter 368. The separation process 600 is similar to the separation process 350 illustrated in FIG. 9 with the exception that the organic phase stream from the decanter 388 is recycled to the third distillation column 380 and the bottoms stream 600 from the third distillation column 380 may pass to a different series of separation units. The remaining components of the separation process 600 may be the same or similar to those described with respect to FIG. 9, and the similar components will not be described with respect to FIG. 11 in the interest of brevity.

In this embodiment, the overhead stream from the third distillation column 380 can be at least partially condensed in the heat exchanger 386 and pass to the decanter 388. The organic phase, and optionally a fraction of the aqueous phase, can be refluxed to the third distillation column 380. The remainder of the aqueous phase can pass out of the decanter 388 and be discharged from the process as the aqueous phase stream 390. The aqueous phase stream 390 may predominately comprise water with a minor amount of dissolved organics.

In this embodiment, the bottoms stream 601 from the third distillation column 380 can pass to a fourth distillation column 602, where the bottoms stream 601 comprises organics that are substantially free of water. The fourth distillation column 602 may comprise any of the types of distillation columns described herein, and the fourth distillation column 602 may operate at a pressure ranging from about 0.1 atm to about 80 atm, or about 0.5 atm to about 40 atm. The fourth distillation column 602 may produce an overhead stream 604 and a bottoms stream 606. The bottoms stream 606 may comprise butanol, butyl acetate, and/or ethyl butyrate, while the remainder of the feed, which may potentially be added to a gasoline pool, can be recovered as the overhead stream 604. In an embodiment, the overhead stream 604 can comprise ethyl acetate, propanol, and/or 2-pentanone.

The bottoms stream 606 from the fourth distillation column 602 can be further separated in a fifth distillation column 608. The fifth distillation column 608 may comprise any of the types of distillation columns described herein, and the fifth distillation column 608 may operate at a pressure ranging from about 0.1 atm to about 80 atm, or about 0.5 atm to about 40 atm. The fifth distillation column 608 may produce an overhead stream 610 and a bottoms stream 612. The bottoms stream 612 may comprise butyl acetate. The overhead stream 610, depending on the pressure at which the fifth distillation column 608 is operating, may comprise high purity butanol (e.g., when the pressure is greater than about 3 atm) or a mixture comprising predominantly of butanol, butyl acetate, and/or ethyl butyrate (e.g., when the pressure is below about 3 atm). The overhead stream 610 can be recycled to the first distillation column 362, or inlet stream 352. In some embodiments, two or more of the columns (e.g., the third distillation column 380, the fourth distillation column 602, and/or the fifth distillation column 608) may be combined into a single column, with the desired streams recovered as side streams. In addition, side rectifiers/strippers may be used to enhance the purity of the side stream products.

The selection of the appropriate separation scheme may be based on the composition of the inlet mixture 352, the composition of the desired products (e.g., one or more high purity streams and/or one or more mixed streams), and/or the economics of the overall process. In addition, various modifications and alterations are contemplated when the relative proportion and compositions of the products change.

Suitable conversion catalysts and combinations thereof are capable of converting at least a portion of the ethanol in a feed stream to a higher valued product such as ethyl acetate and butanol and/or converting the ethyl acetate and butanol to butyl acetate and ethanol. Suitable conversion catalysts may comprise any catalyst capable of carrying out a dehydration, dehydrogenation, aldol condensation reaction, and/or a transesterification reaction, and may be used alone or in combination with additional catalytic materials in the reactors. In an embodiment, suitable conversion catalysts can generally comprise metals, oxides, or salts, or any combination thereof, of copper, barium, ruthenium, rhodium, platinum, palladium, rhenium, silver, cadmium, zinc, zirconium, gold, thallium, magnesium, manganese, aluminum, chromium, nickel, iron, molybdenum, sodium, strontium, tin, and mixtures thereof. In many cases, the conversion catalyst material will be provided on a support material. The conversion catalyst can be treated with a carbonate (e.g., sodium carbonate), reduced with hydrogen, and/or other suitable treatments prior to use.

Examples of suitable conversion catalysts include, but are not limited to, $CuO/SiO_2$, $CuO/SiO_2$—$Al_2O_3$, $CuO/ZnO$, $CuO/ZrO_2$, $CuO/SiO_2$—$ZrO_2$, $CuO/Al_2O_3$, $Cu/SiO_2$, $Cu/SiO_2$—$Al_2O_3$, $Cu/ZnO$, $Cu/ZrO_2$, $Cu/SiO_2$—$ZrO_2$, $Cu/Al_2O_3$ or any combination thereof. In an embodiment, these catalysts, or any combination thereof, may be prepared via impregnation of an oxide catalyst, such as, for example, by the impregnation techniques disclosed herein and described in more detail below. In general, a metal oxide catalyst can be converted to the elemental metal in situ during the reactive distillation process. The elemental metal may then serve as a catalytic component in the reaction. Accordingly, any description of a catalyst comprising a metal oxide may also include the same catalyst with the elemental metal in the catalyst rather than, or in addition to, the metal oxide.

Examples of suitable conversion catalysts also include, but are not limited to, $CuO/ZnO/SiO_2$, $CuO/ZrO_2/SiO_2$, $CuO/MgO/SiO_2$, $CuO/CaO/SiO_2$, $CuO/SrO/SiO_2$, $CuO/BaO/SiO_2$, $CuO/ZrO_2/Al_2O_3/SiO_2$, $CuO/Na_2O/SiO_2$, $CuO/MgO/Al_2O_3/SiO_2$ $CuO/CeO_2/MgO/Al_2O_3$ or any combination thereof. In an embodiment, the $CuO/ZnO/SiO_2$, $CuO/ZrO_2/SiO_2$, $CuO/MgO/SiO_2$, $CuO/CaO/SiO_2$, $CuO/SrO/SiO_2$, $CuO/BaO/SiO_2$, $CuO/ZrO_2/Al_2O_3/SiO_2$, $CuO/Na_2O/SiO_2$, or any combination thereof may be prepared via co-impregnation of a silica catalyst support, such as, for example, by the co-impregnation techniques disclosed herein and described in more detail below. In an another embodiment, the CuO/ZnO/SiO$_2$, CuO/ZrO$_2$/SiO$_2$, CuO/MgO/SiO$_2$, CuO/CaO/SiO$_2$, CuO/SrO/SiO$_2$, CuO/BaO/SiO$_2$, CuO/ZrO$_2$/Al$_2$O$_3$/SiO$_2$, CuO/Na$_2$O/SiO$_2$, CuO/K$_2$O/SiO$_2$, CuO/Rb$_2$O/SiO$_2$, CuO/Cs$_2$O/SiO$_2$, or any combination thereof may be prepared via sequential impregnation of a silica catalyst support, such as, for example, by the sequential impregnation techniques disclosed herein and described in more detail below.

Examples of suitable conversion catalysts also include, but are not limited to, CuO/ZnO/Al$_2$O$_3$, CuO/Cr$_2$O$_3$/Al$_2$O$_3$, CuO/ZrO$_2$/Al$_2$O$_3$, or any combination thereof. In an embodiment, the CuO/ZnO/Al$_2$O$_3$, CuO/Cr$_2$O$_3$/Al$_2$O$_3$, CuO/ZrO$_2$/Al$_2$O$_3$, or any combination thereof may be prepared via co-impregnation of an alumina support, such as, for example, by the co-impregnation techniques disclosed herein and described in more detail below.

In general, catalysts for the production of butyl acetate may produce ethyl acetate, butanol, and/or butyl acetate. Suitable catalysts for producing these reaction products with only minor amounts of by-products include Guerbet reaction catalysts, including but not limited to hydroxyapatite and solid base Guerbet reaction catalysts, solid base multicomponent oxide catalysts, zeolites with alkali counterions, magnesium oxide, or any combination thereof.

The conversion catalyst may comprise nickel or nickel oxide supported on alumina, and the conversion catalyst may have a nickel weight loading of between about 2% and about 20%. The conversion catalyst may comprise co-precipitated catalysts represented by the formula:

$$M/MgO/Al_2O_3,$$

wherein M represents palladium, rhodium, nickel, or copper, or oxides thereof.

The conversion catalyst may comprise oxide powders of copper, lead, zinc, chromium, molybdenum, tungsten, manganese, lead, salts thereof, and any combination thereof. In an embodiment, the conversion catalyst may comprise a zeolite with an alkali metal.

The conversion catalyst may comprise solid base catalysts and solid acid/base bifunctional catalysts. The conversion catalyst may comprise a hydroxyapatite represented by the formula $$Ca_{10}(PO_4)_6(OH)_2$$

wherein the ratio of calcium to phosphorus (Ca:P) is between about 1.5 and about 1.8 for nonstoichiometric hydroxyapatites. In some embodiments, the conversion catalyst may comprise an apatite structure satisfying the formula:

$$M_a(M'O_b)_cX_2,$$

wherein M represents calcium, strontium, magnesium, barium, lead, cadmium, iron, cobalt, nickel, or zinc, M' represents phosphorus, vanadium, arsenic, carbon, or sulfur, and X represents a fluorine, chlorine, bromine, or a hydroxide. In one embodiment, a, b, and c are whole numbers that balance the valence requirements of M, M', and X. In another embodiment, a is 10, b is 3, and c is 6. In another embodiment, $M_a(M'O_b)_cX_2$ is a non-stoichiometric apatite, and a is about 10, b is about 3, c is about 6, and the ratio of a to c (a:c) is between about 1.5 and about 1.8. The conversion catalyst may comprise a basic a calcium and/or magnesium phosphate compound including calcium and/or magnesium phosphates, phosphate carbonates, pyrophosphates, or the like. In an embodiment, the conversion catalyst may also comprise magnesium oxide, magnesium hydroxide, magnesium phosphate hydrate (Mg$_3$(PO$_4$)$_2$. 8H$_2$O), calcium oxide, calcium hydroxide, calcium fluoride, calcium silicate (wollastonite), calcium sulfate dihydrate (gypsum), lithium phosphate, aluminum phosphate, titanium dioxide, fluorapatite (Ca$_{10}$(PO$_4$)$_6$F$_2$), tetracalcium phosphate (e.g. Ca$_4$(PO$_4$)$_2$O), hydrotalcite, talc, kaolin, sepiolite, or any combination thereof.

In certain embodiments, the conversion catalyst may include a catalyst support. The catalyst support stabilizes and supports the catalyst. The type of catalyst support used depends on the chosen catalyst and the reaction conditions. Suitable supports may include, but are not limited to, carbon, silica, silica-alumina, alumina, zirconia, titania, ceria, vanadia, boron nitride, heteropolyacids, hydroxyapatite, zinc oxide, chromia, zeolites, carbon nanotubes, carbon fullerenes, and any combination thereof.

The conversion catalyst can be employed in any of the conventional types or structures known to the art. It may be employed in the form of extrudates, pills, pellets, granules, broken fragments, or various special shapes. In an embodiment, consideration of the use of the conversion catalyst in the reactive distillation system and/or as a mass transfer surface within the distillation column may be taken into account when determining a suitable shape. For example, the conversion catalyst may have a shape similar to structured packing material or suitable for insertion in a structured packing. When the conversion catalyst is used with one or more side reactors, the catalyst may be disposed within a reaction zone, and the feed may be passed therethrough in the liquid, vapor, or mixed phase, and in either upward or downward, or inward or outward flow.

The conversion catalyst may typically have a range of metal loadings. In an embodiment, the conversion catalysts may have a copper oxide weight loading (i.e., weight percentage) of between about 0.5% and about 80%, between about 10% and about 70%, between about 20% and about 65%, between about 30% and about 60%, or about 40% and about 50%. In an embodiment, the conversion catalysts may have an a aluminum oxide weight loading of between about 20% and about 60%, between about 30% and about 50%, or between about 40% and about 50%. In an embodiment, the conversion catalysts may have a zirconium dioxide weight loading of between about 20% and about 60%, or between about 30% and about 50%.

In an embodiment, the conversion catalysts may comprise CuO/Al$_2$O$_3$ disposed on a zirconium dioxide support. In this embodiment, the conversion catalysts may have a copper oxide weight loading of between about 0.5% and about 80%, between about 10% and about 70%, between about 20% and about 65%, between about 30% and about 60%, or about 40% and about 50%, and the alumina and zirconium dioxide may comprise the balance of the weight. In an embodiment, the conversion catalysts may comprise CuO/ZrO$_2$ disposed on an alumina support. In this embodiment, the conversion catalysts may have a copper oxide weight loading of between about 0.5% and about 80%, between about 10% and about 70%, between about 20% and about 65%, between about 30% and about 60%, or about 40% and about 50%, and the alumina and zirconium dioxide may comprise the balance of the weight.

In an embodiment, the conversion catalyst described herein may be capable of achieving a relatively high conversion and/or selectivity of ethanol to ethyl acetate and/or butanol, which may then be converted to butyl acetate. As used herein, the "conversion" of the ethanol to ethyl acetate and/or butanol refers to the amount of the ethanol consumed in the conversion reaction as represented by the formula:

$$X_{Ethanol} = 100\left(\frac{n_{Ethanol} - n_{Ethanol,0}}{n_{Ethanol,0}}\right) \quad \text{(Eq. 8)}$$

where $n_{Ethanol}$ represents the molar flow rates of the ethanol in the reactor effluent (e.g., the product stream comprising the ethyl acetate and/or butanol), and $n_{Ethanol,0}$ represents the molar flow rate of the ethanol into the reactor inlet. In an embodiment, the conversion catalyst described herein may be capable of achieving a conversion of the ethanol in the reactive distillation process described herein of at least about 10%, at least about 20%, at least about 30%, or at least about 40%. The catalyst may be produced using a variety of techniques as described in more detail below.

As used herein, the "total selectivity" of the conversion refers to the amount of the ethanol that is consumed in the conversion reaction that is converted to ethyl acetate and butanol as represented by the formula:

$$S_{total} = 100\left(\frac{3n_{Butyl\ acetate} + 2n_{Ethyl\ Acetate} + 2n_{Butanol}}{n_{Ethanol} - n_{Ethanol,0}}\right) \quad \text{(Eq. 9)}$$

where $n_{Butyl\ Acetate}$, $n_{Ethyl\ Acetate}$, and $n_{Butanol}$ represent the molar flow rate of the butyl acetate, the ethyl acetate, and the butanol in the reactor effluent (e.g., the product stream comprising the ethyl acetate and/or butanol), respectively, and the remaining terms are the same as described above with respect to the conversion of ethanol. Acetaldehyde is an intermediate product in the reaction to make ethyl acetate (and possibly for the reaction to make butanol) and is therefore included in the total selectivity calculation. In an embodiment, the conversion catalyst described herein may be capable of achieving a total selectivity ($S_{total}$) in the reactive distillation process described herein of at least about 60%, at least about 70%, at least about 80%, at least about 85%, at least about 90%, or at least about 95%.

It is to be understood that the catalysts may include a blend of one or more catalysts that convert the ethanol to pure or substantially pure butanol with one or more catalysts that convert the ethanol to pure or substantially pure ethyl acetate. Catalysts that convert the ethanol to pure or substantially pure ethyl acetate include, but are not limited to, the catalysts disclosed in U.S. Patent Publication No. 2013/0197266 entitled "Ethyl Acetate Production," to Gadewar, et al, which is incorporated herein by reference in its entirety. Various catalysts of U.S. Patent Publication No. 2013/0197266 suitable for use in the production of butanol and/or ethyl acetate are further described in Examples of the present application. The catalysts of the Examples, however, are not intended to be a complete listing of all catalysts from U.S. Patent Publication No. 2013/0197266 suitable for use in the production of butanol and/or ethyl acetate production processes, systems, and methods of the present application. The ability to blend the catalyst may allow a desired molar ratio of ethyl acetate to butanol to be achieved to aid in the conversion of the ethyl acetate and butanol to butyl acetate. In an embodiment, the molar ratio may be approximately balanced to between about 1.5:1 to about 1:1.5. The conversion catalysts may be produced using a variety of techniques as described in more detail below.

Various hydrogenation catalysts may be used as described above. The hydrogenation catalyst generally can include a Group VIII metal and/or a Group VI metal. Examples of such a catalyst can include, but are not limited to, Cu, Re, Ni, Fe, Co, Ru, Pd, Rh, Pt, Os, Ir, and alloys, oxides (e.g., $PtO_2$), or any combination thereof, either alone or with promoters such as W, Mo, Au, Ag, Cr, Zn, Mn, Sn, B, P, Bi, and alloys, oxides (e.g., $Cr_2O_3$, $Cu_2Cr_2O_5$), or any combination thereof. Other effective hydrogenation catalyst materials include either supported nickel or ruthenium modified with rhenium. In an embodiment, the hydrogenation catalyst also includes any one of the supports described below, depending on the desired functionality of the catalyst. The hydrogenation catalysts may be prepared by methods known to those of ordinary skill in the art.

In an embodiment, the hydrogenation catalyst includes a supported Group VIII metal catalyst and a metal sponge material (e.g., a sponge nickel catalyst such as Raney nickel). Raney nickel provides an example of an activated sponge nickel catalyst suitable for use in this invention. In an embodiment, the hydrogenation reaction in the invention is performed using a catalyst comprising a nickel-rhenium catalyst or a tungsten-modified nickel catalyst. One example of a suitable catalyst for the hydrogenation reaction of the invention is a carbon-supported nickel-rhenium catalyst.

In an embodiment, a suitable Raney nickel catalyst may be prepared by treating an alloy of approximately equal amounts by weight of nickel and aluminum with an aqueous alkali solution, e.g., containing about 25 wt % of sodium hydroxide. The aluminum is selectively dissolved by the aqueous alkali solution resulting in a sponge shaped material comprising mostly nickel with minor amounts of aluminum. The initial alloy includes promoter metals (e.g., molybdenum or chromium) in the amount such that 1 to 2 wt % remains in the formed sponge nickel catalyst.

In another embodiment, the hydrogenation catalyst is prepared using a solution of ruthenium(III) nitrosylnitrate or ruthenium (III) chloride in water to impregnate a suitable support material. The solution is then dried to form a solid having a water content of less than 1% by weight. The solid is then reduced at atmospheric pressure in a hydrogen stream at 300° C. (uncalcined) or 400° C. (calcined) in a rotary ball furnace for 4 hours. After cooling and rendering the catalyst inert with nitrogen, 5% by volume of oxygen in nitrogen is passed over the catalyst for 2 hours.

In certain embodiments, the hydrogenation catalyst may include a catalyst support, which may be the same or different than a catalyst support used with the conversion catalyst. In an embodiment, any of the catalyst supports discussed herein may be used to support a hydrogenation catalyst. The hydrogenation catalyst can be employed in any of the conventional types or structures known to the art. In an embodiment, any of the catalyst shapes and/or types discussed herein with respect to the conversion catalyst may be used with the hydrogenation catalyst.

Any of the materials useful as catalysts, may be synthesized using a variety of methods. In an embodiment, the catalyst may be prepared via wet impregnation of a catalyst support. Using the wet-impregnation technique, a metal salt (e.g., a metal nitrate, acetate, etc.) dissolved in a suitable solvent may be used to prepare the catalyst, however any soluble compound would be suitable. A sufficient amount of solvent should be used to fully dissolve the metal nitrate and appropriately wet the support. In one embodiment, copper nitrate and ethanol and/or water may be mixed in an amount sufficient such that the copper nitrate dissolves. Additional metal nitrates may also be added to provide a catalyst with additional components. The solute may then be combined with a suitable support material of appropriate particle size. The mixture may then be refluxed at a temperature of approximately 100° C. for approximately several hours (e.g., three to five hours) and then allowed to dry at a temperature of about 110° C. The dried material may then be heated to 200° C. to at least partially decompose the nitrates to the corresponding oxides, and then the materials may be calcined at about 400° C. to about 600° C. at a heating rate of about one to ten ° C./min over a period of about 2 to about 10 hours to fully remove the $NO_x$ component. The amount of metal nitrate used in the wet-impregnation technique can be adjusted to achieve a desired final metal weight loading of the catalyst support.

When multiple components are used to provide a catalyst disposed on a support, each component can be added via the wet-impregnation technique. The appropriate salts can be dissolved and impregnated on a support in a co-impregnation process or a sequential process. In a co-impregnation process, measured amount of the appropriate plurality of metal salts may be dissolved in a suitable solvent and used to wet the desired catalyst support. The impregnated support can then be dried and calcined to provide a final catalyst with a desired weight loading. In the sequential impregnation process, one or more measured amounts of salts may be dissolved in a suitable solvent and used to wet the desired catalyst support. The impregnated support can then be dried and calcined. The resulting material can then be wetted with one or more additional salts that are dissolved in a suitable solvent. The resulting material can then be dried and calcined again. This process may be repeated to provide a final catalyst material with a desired loading of each component. In an embodiment, a single metal may be added with each cycle. The order in which the metals are added in the sequential process can be varied. Various metal weight loadings may be achieved through the wet-impregnation technique. In an embodiment, the wet-impregnation technique may be used to provide a catalyst having a copper weight loading ranging from about 0.5% and about 50%, with one or more additional components having a weight loading between about 0.1% and about 40% each.

In some embodiments, each component can be added via a wet-impregnation technique to a catalyst material in paste form, which can then be incorporated onto a support. In this technique, the appropriate salt, acid, or base can be prepared and impregnated on a catalyst material to form a paste. The impregnated catalyst material can then be dried and calcined to provide a final catalyst with a desired weight loading. In the sequential impregnation process, one or more measured amounts of salts, acids, and/or bases may be dissolved in a suitable solvent and used to wet the desired catalyst material. The impregnated support can then be dried and calcined. The resulting material can then be wetted with one or more additional salts, acids, and/or bases that are dissolved in a suitable solvent. The resulting material can then be dried and calcined again. This process may be repeated to provide a final catalyst material with a desired loading of each component. The catalyst material may then be incorporated into a support and/or formed in a catalyst form such as a pellet for use in the reaction.

The catalysts may also be prepared via a co-precipitation technique. In this technique, a measured amount of one or more appropriate metal nitrates are dissolved in de-ionized water. The total metal concentration can vary and may generally be between about 0.01 M and about 3 M. The metal-nitrate solution may then be precipitated through the drop-wise addition of the solution to a stirred, equal volume of a sodium hydroxide solution at room temperature. The sodium hydroxide solution may generally have a concentration of about 4M, though other concentrations may also be used as would be known to one of skill in the art with the benefit of this disclosure. In some embodiments, the solutions may be combined in the opposite order. For example, the metal salt solution may be prepared and added (e.g., added drop-wise) to a basic solution such as a sodium hydroxide solution. The order of the addition (e.g., metal salt solution to the basic solution or the basic solution to the metal salt solution) may affect the composition of the precipitate formed during the precipitation process.

After addition of the metal nitrate solution or vice versa, the suspension may then be stirred over a period of about 1 to about 24 hours. The resulting suspension can then be filtered and washed with de-ionized water. The filtered solids can be dried overnight, for example, at a temperature of about 110° C., and then the materials may, optionally, be calcined at about 220° C. to about 500° C. at a heating rate of about one to ten ° C./min. The resulting mixed metal oxide can then be processed to a desired particle size. For example, the resulting mixed metal oxide can be pressed to a desired form, ground, and then sieved to recover a catalyst material with a particle size in a desired range. Catalysts prepared using the co-precipitation technique may have higher metal loadings than the catalysts prepared using the wet-impregnation technique.

Catalysts prepared via the co-precipitation technique may be used in the prepared form and/or a catalyst binder can be added to impart additional mechanical strength. In an embodiment, the prepared catalyst may be ground to a fine powder and then stirred into a colloidal suspension (e.g., a colloidal suspension of silica and/or alumina) in an aqueous and/or organic solution. The resulting suspension may be stirred while being heated and allowed to evaporate to dryness. The heating may take place at about 80° C. to about 130° C. The resulting solid can then be processed to a desired particle size. For example, the resulting solid can be extruded or pressed to a desired form, ground, and then sieved to recover a catalyst material with a particle size in a desired range. Alternatively, the colloidal suspension may be added to the 4M sodium hydroxide precipitation solution prior to addition of the metal nitrate solution in the co-precipitation technique. Other metal salts, such as acetates, chlorides, sulfates, and the like can be used in place of the metal nitrates.

Various metal weight loadings may be achieved through the co-precipitation technique. In an embodiment, the co-precipitation technique may be used to provide a catalyst having a copper weight loading ranging from about 2% to about 80%, with one or more additional component having a weight loading between about 2% and about 40%.

The resulting catalyst from either the wet-impregnation technique and/or the co-precipitation technique may be further treated prior to use in the reactive distillation system disclosed herein. In an embodiment, the catalyst may be treated with a basic solution such as a sodium carbonate solution or a diluted sodium hydroxide solution for a period of time to improve the selectivity of the catalyst. In this process, the catalyst may be soaked in an aqueous solution of sodium carbonate for a period of time ranging from about 1 hour to about 48 hours, or alternatively about 2 hours to about 24 hours. In an embodiment, the sodium carbonate solution may have a concentration of about 0.2 M. The catalyst may then be filtered and allowed to dry at about room temperature. In an embodiment, the sodium carbonate may comprise from about 0.2 to about 3.0 weight percent of the catalyst after being contacted with the sodium carbonate solution.

In another treatment process, the catalyst may be reduced with hydrogen prior to use. In this embodiment, the catalyst may be heated and contacted with hydrogen, which may be flowing over the catalyst, for a period of time sufficient to reduce the catalyst to a desired degree. In an embodiment, the catalyst may be contacted with hydrogen at a temperature of about 150° C. to about 240° C. The hydrogen treatment may be conducted in combination with the sodium carbonate treatment, and may be performed prior to and/or after the sodium carbonate treatment.

Without intending to be limited by theory, it is believed that the production of hydrogen during the dehydrogenation and dimerization reaction within the process may result in contact between the conversion catalyst and a hydrogen stream sufficient to at least partially reduce the catalyst. Thus, the process described herein may have the potential for the in-situ reduction of the catalyst during use. This may result in an initial break-in period in which the catalyst conversion and selectivity may change before reaching a steady state conversion and selectivity. This in-situ reduction may be taken into account when considering the degree to which a catalyst should be pre-reduced with hydrogen.

In some embodiments, the catalyst used to produce butanol, ethyl acetate, and/or butyl acetate from the butanol and ethyl acetate may comprise a multi-component catalyst: a first dehydrogenation catalyst component and a second solid base catalyst component. The first component of the multi-component catalyst may comprise any of the catalysts elements described herein with respect to the hydrogenation catalysts. The second component of the multi-component catalyst may comprise any of the catalysts elements described herein with respect to the catalysts for producing butanol, ethyl acetate, and/or butyl acetate.

The relative amount of each of the first and second component may vary in the multi-component catalyst to achieve the desired dehydrogenation/hydrogenation performance. In an embodiment, the amount of the first catalyst component may generally be less than about 30% by volume, less than about 25% by volume, less than about 20% by volume, less than about 15% by volume, less than about 10% by volume, or less than about 5% by volume. The amount of the first catalyst component may be greater than about 0.1% by volume, greater than about 1% by volume, greater than about 2% by volume, greater than about 3% by volume, greater than about 4% by volume, or greater than about 5% by volume. In an embodiment, the ratio of the volume of the first catalyst component to the volume of the second catalyst component may range from about 1:2 to about 1:100, from about 1:5 to about 1:90, or from about 1:10 to about 1:80.

In an embodiment, optional components such as binders and/or supports may also be present in the multi-component catalyst. The multi-component catalyst can be employed in any of the conventional types or structures known to the art. It may be employed in the form of extrudates, pills, pellets, granules, broken fragments, or various special shapes. In an embodiment, consideration of the use of the multi-component catalyst in the reactive distillation system and/or as a mass transfer surface within the distillation column may be taken into account when determining a suitable shape. For example, the multi-component catalyst may have a shape similar to structured packing material or suitable for insertion in a structured packing. In some embodiments, the catalyst may comprise a particular material that is dispersed in the reactants.

In some embodiments, the first catalyst component that catalyzes hydrogenation-dehydrogenation could be any common hydrogenation catalyst for example Cu, Pd, Pt, $Cr_2O_3$, $PtO_2$, and/or $Cu_2Cr_2O_5$ (e.g., a Lazier catalyst). Copper may be beneficial because of its lower cost and low byproduct formation. In some embodiments, the second catalyst component of the multi-component catalyst may be one or more of MgO, $Mg(OH)_2$, magnesium carbonates and calcium phosphates (e.g. $Ca_5(OH)(PO_4)_3$, $Ca_2P_2O_7$ and other calcium phosphates), layered double hydroxide minerals either natural or synthetic such as hydrotalcite, kaolinite as well as the products of their interaction with alkaline earth oxides or hydroxides such as MgO, $Mg(OH)_2$, CaO, $Ca(OH)_2$ or their carbonates at high temperatures. Strontium and barium oxides, hydroxides and phosphates can be potentially used in the process as solid base components as well.

The activity of the second component of the multi-component catalyst was found to depend on the method of preparation. The multi-component catalyst can be prepared by any of the methods described herein for preparing a catalyst, including, but not limited to, physically mixing the two components, sol-gel co-precipitation, or loading the dehydrogenation catalyst on the base catalyst component by impregnation. Each of these methods was found to lead to the creation of active catalyst. Physical mixing may be beneficial due to its simplicity, while an impregnation process resulted in higher performance.

In an embodiment, the second catalyst component of the multi-component catalyst may comprise MgO. As illustrated in the Examples accompanying this disclosure, the activity of a catalyst comprising MgO was observed to vary depending on its source, method of preparation and pretreatment. For example, purchased MgO was found to have conversions less than about 5%, high surface area MgO (e.g., catalysts made by an aerogel method, etc.) was found to have conversions up to about 26%, and MgO made from hydroxide and carbonate decomposition as described herein was found to have conversions up to about 65%.

Accordingly, the present application discloses the use of reactive distillation for the production of butyl acetate from ethanol. The present application discloses the use of Guerbet reaction catalysts and other catalysts in a reactive distillation process to produce butyl acetate from ethanol. The present application also discloses the production of butyl acetate from an ethanol feed in a single reactor. Still further, the present application discloses the use of supported catalysts, particularly $CuO/ZrO_2$ supported on $Al_2O_3$ and $CuO/Al_2O_3$ supported on $ZrO_2$, for the production of butyl acetate.

EXAMPLES

The disclosure having been generally described, the following examples are given as particular embodiments of the disclosure and to demonstrate the practice and advantages thereof. It is understood that the examples are given by way of illustration and are not intended to limit the specification or the claims in any manner.

Examples 1-5

Examples 1-5 relate to catalysts useful for the production of butanol, the production of butanol and/or ethyl acetate, or a combination thereof in various systems and methods described in the present application.

Example 1

Wet-Impregnation Catalyst Preparation $CuO/SiO_2$, $CuO/SiO_2$—$Al_2O_3$, $CuO/ZnO$, $CuO/ZrO_2$, $CuO/SiO_2$—$ZrO_2$ and $CuO/Al_2O_3$ catalysts were prepared via impregnation of an oxide catalyst support. In a typical co-impregnation, a measured amount of $Cu(NO_3)_2 \cdot 2.5H_2O$ is dissolved in an appropriate amount of de-ionized water to fill the pore volume of the support. The solution is added to the support and agitated until the liquid is fully absorbed. The impregnated support is then dried in air at 110° C., followed by calcination in air at 400 to 600° C. for 2 to 10 hours. The amount of $Cu(NO_3)_2 \cdot 2.5H_2O$ can be adjusted to achieve a desired final Cu weight loading. Typical Cu loadings are between 0.5 and 50 wt %.

Example 2

Co-Impregnation and Sequential Impregnation Catalyst Preparation $CuO/ZnO/SiO_2$, $CuO/ZrO_2/SiO_2$, $CuO/MgO/SiO_2$, $CuO/CaO/SiO_2$, $CuO/SrO/SiO_2$, $CuO/BaO/SiO_2$, $CuO/ZrO_2/Al_2O_3/SiO_2$ and $CuO/Na_2O/SiO_2$ catalysts were prepared via co-impregnation and sequential impregnation of a silica catalyst support. In a typical co-impregnation, measured amounts of $Cu(NO_3)_2 \cdot 2.5H_2O$ and $M(NO_3)_x \cdot YH_2O$ (M=Zn, ZrO, Mg, Ca, Sr, Ca, Al or Na; X=1, 2, 4; Y=2-6) is dissolved in an appropriate amount of de-ionized water to fill the pore volume of the silica support. The solution is added to the silica support and stirred until well mixed. The impregnated silica is then dried in air at 110° C., followed by calcination in air at 400-600° C. for 2-10 hours. Typical catalyst loadings range from 1-50 wt % CuO and 2 to 40 wt % $M_iO_j$.

$CuO/ZnO/Al_2O_3$, $CuO/Cr_2O_3/Al_2O_3$, and $CuO/ZrO_2/Al_2O_3$ catalysts were prepared via co-impregnation of an alumina support. A sample in which Cu, Zr and Al oxides were supported on alumina ($CuO/ZrO_2/Al_2O_3/Al_2O_3$) was also prepared. In a typical co-impregnation, measured amounts of $Cu(NO_3)_2 \cdot 2.5H_2O$ and $M(NO_3)_x \cdot YH_2O$ (M=Zn, ZrO, or Cr; X=1, 2, 3; Y=6 or 9) are dissolved in an appropriate amount of de-ionized water to fill the pore volume of the alumina support. The solution is added to the alumina support and agitated until the liquid is fully absorbed. The impregnated alumina is then dried in air at 110° C., followed by calcination in air at 400-600° C. for 2-10 hours. Typical catalyst loadings range from 1 to 50 wt % CuO and 2 to 40 wt % $M_iO_j$.

$CuO/MgO/Al_2O_3/SiO_2$ and $CuO/MgO/Al_2O_3/Al_2O_3$ catalysts were prepared via co-impregnation and sequential impregnation of a silica or alumina catalyst support. In a typical co-impregnation, measured amounts of $Cu(NO_3)_2 \cdot 2.5H_2O$ and $M(NO_3)_x \cdot YH_2O$ or $M(CH_3COO)_x \cdot YH_2O$ (M=Mg, Al; X=2, 4; Y=2-6) is dissolved in an appropriate amount of de-ionized water. The solution is added to the silica or alumina support slowly and gradually to achieve good salt distribution on the support (incipient wetting). The impregnated silica or alumina is then dried in air at 110° C., followed by calcination in air at 400-600° C. for 2-10 hours. Typical catalyst loadings range from 1-50 wt % CuO and 2 to 40 wt % $M_iO_j$. An example of final product is 1.5 wt. % Cu, 13 wt. % MgO and 2 wt. % $Al_2O_3$ on granulated silica or alumina.

Example 3

Co-Precipitation Catalyst Preparation

Mixed-metal oxide catalysts were prepared via co-precipitation from nitrate solutions. In a typical co-precipitation synthesis, a measured amount of the appropriate metal nitrates (Cu, Zn, Zr, Al, Cr, Fe, Ni, Ba) are dissolved in de-ionized water (total metal concentration range from 0.5 to 3 M). The metal-nitrate solution is then precipitated by drop-wise addition into a stirred, equal volume of 4 M aqueous NaOH at room temperature. After addition of all the metal nitrate solution, the suspension is stirred for 12 to 24 hours to ensure complete precipitation of the metal oxides. The precipitated solid is then filtered and washed with excess de-ionized water. The solids are then dried overnight at 110° C., followed by calcination at 220 to 500° C. Catalysts prepared in this manner have CuO loadings between 40 to 80 wt %. The loadings of other metal oxides range from 2 to 40 wt %.

A catalyst binder can be added to the mixed-metal oxide to impart additional mechanical strength. The metal oxide catalyst is ground to a fine powder and then stirred into a colloidal suspension of silica or alumina in water. The resulting suspension is stirred while heating at 80 to 130° C. to dryness. The resulting solid can then be either extruded or pressed, ground, and sieved to appropriate particle sizes. An alternative is to add the colloidal silica or alumina suspension to the 4 M NaOH precipitation solution prior to addition of the metal nitrate solution. Other metal salts, including acetates and carbonates can be used in place of the nitrates.

Example 4

Direct Synthesis of Butyl Acetate from Ethanol

Figure 12:
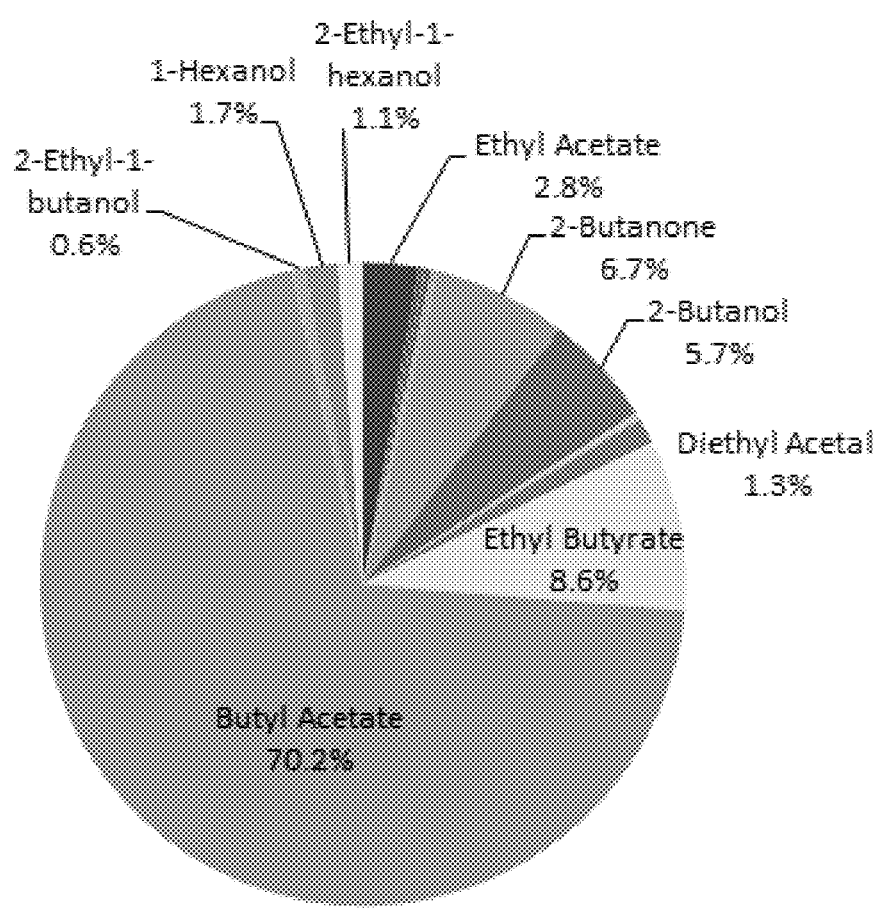
FIG. 12 illustrates an organic product distribution from a fixed bed reactor using an embodiment of a catalyst.
Figure 13:
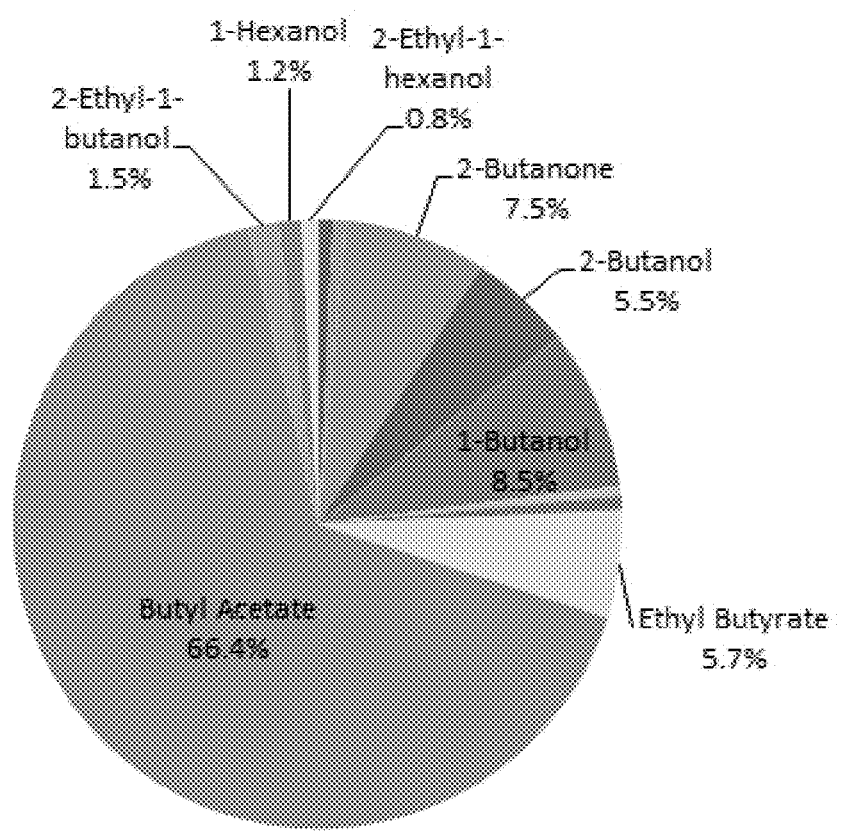
FIG. 13 illustrates another organic product distribution using another embodiment of a catalyst.

A portion of the catalysts prepared as described in Examples 1-3 were tested in butyl acetate synthesis reactions after being reduced in a stream of $H_2$ at a temperature between 175 and 240° C. Table 1 shows the conversion and selectivity of the catalysts butyl acetate synthesis reactions conducted in a fixed bed reactor. FIG. 12 illustrates a product distribution in wt % using CuO/MgO on $SiO_2$ with a 0.10 ml/min ethanol feed at 260° C. and 500 psig, and FIG. 13 show organic product distributions in wt % using $CuO/MgO/Al_2O_3$ on $SiO_2$ with a 0.10 ml/min ethanol feed at 260° C. and 500 psig. Conversion and selectivity for gas phase reactions were determined using a fixed bed reactor operating at 220-300° C. and 1-35 atm. Pure ethanol was fed to the reactor with a liquid hourly space velocity (LHSV) between 0.1-1.5 $hr^{-1}$. Conversion ($X_{ethanol}$), selectivity ($S_{BuOAc}$), and molar ratio of ethyl acetate to butanol (R) were calculated from the composition of the reactor effluent as $$X_{ethanol} = 100\left(\frac{n_{EtOH} - n_{EtOH,0}}{n_{EtOH,0}}\right),$$

$$S_{BuOAc} = 100\left(\frac{3n_{BuOAc} + 2n_{BuOH} + 2n_{EtOAc}}{n_{EtOH} - n_{EtOH,0}}\right), \text{ and}$$

$$R = \frac{n_{EtOAc}}{n_{BuOH}}$$

respectively, where $n_{BuOAc}$, $n_{EtOAc}$, $n_{BuOH}$, and $n_{EtOH}$ represent the molar flow rate of butyl acetate, ethyl acetate, butanol (e.g., n-butanol and/or 2-butanol), and ethanol in the reactor effluent (e.g., the product stream comprising the butanol), respectively, and $n_{EtOH,0}$ represents the molar flow rate of ethanol into the reactor inlet.

TABLE 1

Conversion and selectivity for selected catalysts in a
fixed bed reactor operating at 260° C. and 35 atm.

| Catalyst sample | $X_{ethanol}$ | $S_{BuOAc}$ | R |
|---|---|---|---|
| Co-Impregnated catalysts | | | |
| CuO/MgO on $SiO_2$ | 22.7 | 79.0 | 1.1 |
| CuO/MgO/$Al_2O_3$ on $Al_2O_3$ | 25.1 | 73.1 | 0.1 |
| CuO/MgO/CeO on $SiO_2$ | 21.9 | 83.3 | 0.3 |
| CuO on MgO/$Al_2O_3$ | 18.0 | 83.0 | 0.4 |
| CuO/MgO on $Al_2O_3$ | 29.8 | 78.1 | 1.1 |
| CuO/MgO/$Al_2O_3$ on $SiO_2$ | 18.8 | 76.0 | 1.9 |
| Sequentially-Impregnated catalysts | | | |
| CuO/MgO on $SiO_2$ | 17.8 | 82.3 | 2.0 |
| Co-precipitation catalysts | | | |
| CuO/MgO/$Al_2O_3$ | 28.6 | 85.5 | 4.5 |
| CuO/MgO/$Al_2O_3$ - high temp calcination | 28.5 | 82.8 | 0.6 |

Example 5

Preparation of Butyl Acetate Catalyst Based on Hydrotalcite

Hydrotalcite was treated with calcium hydroxide to increase its basicity. In this example, 15 grams of synthetic hydrotalcite (sourced from Sigma-Aldrich) was mixed well with 4 g $Ca(OH)_2$ and ~30 ml water to create a thick paste. Approximately 5-6 ml of ethanol was added as well to facilitate the wetting of the hydrophobic hydrotalcite. The paste was stirred very well and allowed to dry at 105° C. The resulting powder was heated to 475° C. at a rate of 1° C./min. and held at 475° C. for 2 hours. Once cooled to room temperature, the material was ground to fine powder, followed by the addition of 1.2 g Cu-nitrate hydrate (Cu$(NO_3)_2$. $2.5H_2O$) dissolved in ~30 ml DI water. The paste was stirred very well, dried and then heated in air to 475° C. at 1° C./min. and held at 475° C. for 2 hours. The powder was pressed in pellets for testing in a fixed bed reactor.

Figure 14:
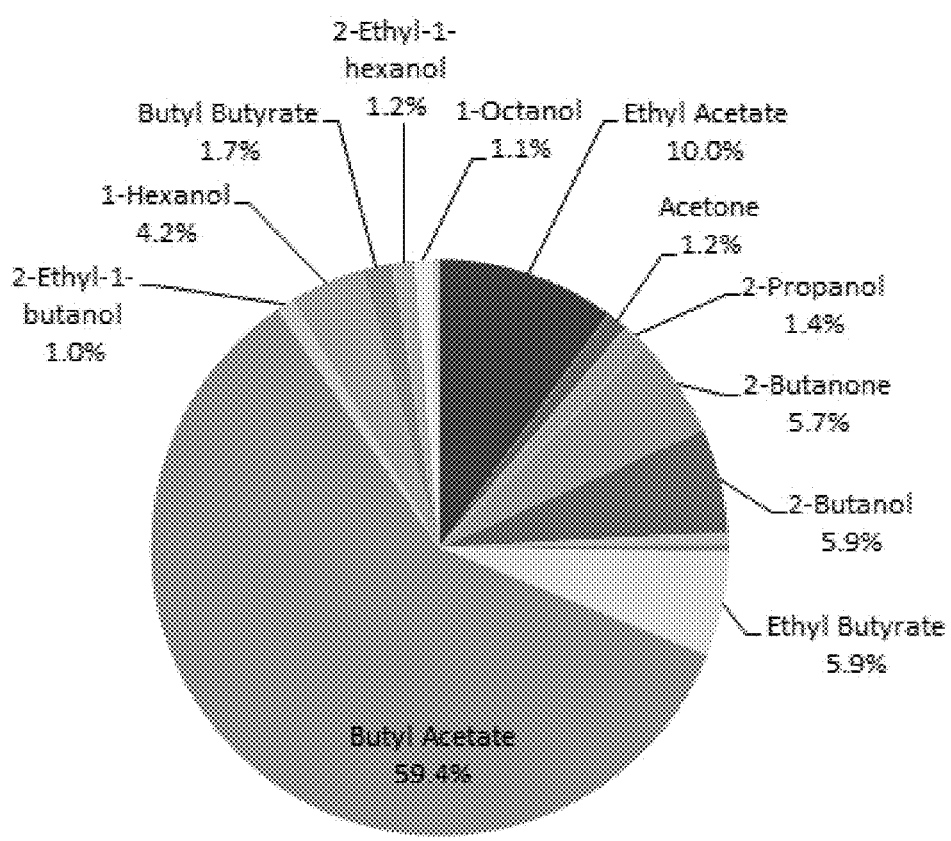
FIG. 14 illustrates still another organic product distribution using still another embodiment of a catalyst.

5.0 g of the pelletized catalyst was loaded into a fixed bed reactor and reduced in a stream of flowing hydrogen at 220° C. for 16 hrs (overnight). After reduction, the catalyst performance was evaluated at 220-280° C. at a pressure of 500 psig with a feed of pure ethanol into a reactor with an LHSV of 1.0 hr$^{-1}$. Table 2 shows the ethanol conversion and the ratio of ethyl acetate to n-butanol in the reactor effluent. FIG. 14 shows the organic product distribution (does not include water, hydrogen, or ethanol) in the reactor effluent at 280° C., which was representative of all of the temperatures tested.

TABLE 2

Ethanol Conversion and Product Molar Ratios

| Temperature (° C.) | Ethanol Conversion (%) | Molar Ratio of Ethyl Acetate to Butanol |
|---|---|---|
| 220 | 9.4 | 1.4 |
| 230 | 12.9 | 1.5 |
| 240 | 16.9 | 1.6 |
| 250 | 21.4 | 1.5 |
| 260 | 25.0 | 1.5 |
| 270 | 30.6 | 1.6 |
| 280 | 35.7 | 1.8 |

From Examples 1 through 5, it can be seen that a high total selectivity to butyl acetate can be attained using the conversion catalysts described herein. In particular, the CuO/MgO on $SiO_2$, CuO/MgO on $Al_2O_3$, and the hydrotalcite catalyst preparations each can simultaneously produce ethyl acetate and butanol, attain a total selectivity above 75%, while producing nearly identical molar ratios of ethyl acetate and butanol. Based on Examples 1 through 5, it can also be seen that a high total selectivity to butanol and ethyl acetate using the conversion catalysts described herein should enable the use of the system embodiments as illustrated in the Figures of the present disclosure. The reaction products can then be converted to butyl acetate in the systems described herein.

Examples 6-9

Examples 6-9 relate to catalysts useful for the production of ethyl acetate in various systems and methods for coproducing butanol and ethyl acetate described in the present application. Additional information regarding the preparation of the catalysts described in Examples 6-9 can be found in U.S. Patent Application Publication No. 2013/0197266 to Gadewar et al., which is incorporated by reference herein in its entirety.

Example 6

Wet-Impregnation Catalyst Preparation

Various catalysts including CuO/$SiO_2$, CuO/$SiO_2$—$Al_2O_3$, CuO/ZnO, CuO/$ZrO_2$, CuO/$SiO_2$—$ZrO_2$, CuO/ZnO/$Al_2O_3$, CuO/$Cr_2O_3$/BaO, CuO/$Cr_2O_3$ and CuO/$Al_2O_3$ were prepared via impregnation of the corresponding oxide catalyst support. The preparation involved dissolving 4 grams (g) of Cu$(NO_3)_2$.$2.5H_2O$ in 30 mL of de-ionized water, which was then added to 30 g of the appropriate oxide support and stirred until well mixed. The impregnated support was then dried in air at 110° C., followed by calcination in air at 450° C. The amount of Cu$(NO_3)_2$.$2.5H_2O$ was adjusted to achieve a desired final Cu weight loading. Enough water was used to wet the entire oxide support. Copper loadings between 0.5% and 20% by weight were achieved.

Example 7

Co-Impregnation and Sequential Impregnation Catalyst Preparation

Various catalysts including CuO/ZnO/$SiO_2$, CuO/$ZrO_2$/$SiO_2$, CuO/MgO/$SiO_2$, CuO/CaO/$SiO_2$, CuO/SrO/$SiO_2$, CuO/BaO/$SiO_2$, and CuO/$Na_2O$/$SiO_2$ were prepared via co-impregnation and sequential impregnation of a silica catalyst support. For the co-impregnation, measured amounts of Cu$(NO_3)_2$.$2.5H_2O$ and M$(NO_3)_x$.$YH_2O$ (M=Zn, ZrO, Mg, Ca, Sr, Ca, or Na; X=1, 2, 4; Y=2-6) were dissolved in de-ionized water. The solution was added to the silica support and stirred until well mixed. The impregnated silica was dried in air at 110° C., followed by calcination in air at 450° C.

For the sequential impregnation, a measured amount of M$(NO_3)_x$.$YH_2O$ (M=Mg, Ca, Sr, Ca, or Na; X=1 or 2; Y=2-6) was dissolved in de-ionized water. The solution was then added to the silica support and mixed well. The silica was dried at 110° C. and then calcined at 450° C. in air. This procedure was then repeated using Cu$(NO_3)_2$.$2.5H_2O$ in place of the first metal nitrate. Copper loadings between 0.5% and 20% by weight and an addition metal loading between 0.1% and 10% by weight were achieved.

Example 8

Co-Precipitation Catalyst Preparation

Mixed-metal oxide catalysts were prepared via co-precipitation from nitrate solutions. In the co-precipitation synthesis, a measured amount of the appropriate metal nitrate (Cu, Zn, Zr, Al, Cr, Fe, Ni, Ba, or any combination thereof) were dissolved in de-ionized water (total metal concentration ranges from 1-3 M). The metal-nitrate solution was then precipitated by drop-wise addition into a stirred, equal volume of 4 M aqueous NaOH at room temperature. After addition of all the metal nitrate solution, the suspension was stirred for an additional 12 to 24 hours to ensure complete precipitation of the metals. The precipitated solid was then filtered and washed with excess de-ionized water. The solids were then dried overnight at 110° C. The resulting mixed metal oxide was then pressed, ground, and sieved to recover a catalyst with particle sizes between 450 and 850 µm. Catalysts prepared in this manner had copper oxide loadings between 40% and 80% by weight. The loadings of other metal oxides ranged from 2% to 40% by weight.

In addition to the catalysts prepare above, various catalysts were prepared via co-precipitation and then a binder was incorporated. The catalyst binder was added to the mixed-metal oxide prepared as described above by first grinding the mixed-metal oxide to a fine powder and then stirring it into a colloidal suspension of silica or alumina in water. The resulting suspension was stirred while heating at 80-130° C. to dryness. The resulting solid was then be pressed, ground, and sieved to appropriate particle sizes.

Example 9

Dehydrogenative Dimerization of Ethanol

A portion of the catalysts prepared as described in Examples 6 to 8 were treated with a $Na_2CO_3$ solution by soaking the catalyst in a 0.2 M aqueous solution of $Na_2CO_3$ for 2-24 hrs. The catalyst was then filtered and allowed to dry in air at room temperature. Another portion of the catalysts were reduced in a hydrogen environment at 175-240° C. for a period of 4-12 hours. These catalysts were then tested in ethanol dehydrogenation reactions. Conversion and selectivity for gas phase reactions were determined from use in a fixed bed reactor operating at 190-240° C. and 1-24 atm. Pure ethanol was fed to the reactor with a weight hourly space velocity (WHSV) between 0.1-1.5 $hr^{-1}$. Conversion and selectivity for liquid phase and mixed liquid/vapor phase reactions were determined a fixed bed reactor, operating at 190-240° C. and at pressures above 25 atm. Liquid phase reactions were also conducted in a batch reactor at 180-200° C. and 20-31 atm (the reactor pressure was maintained above the vapor pressure of ethanol at the operating temperature).

Table 3 shows the conversion and selectivity of the catalysts in a dehydrogenative dimerization reaction conducted in a fixed bed reactor. The conversion of ethanol ($X_{ethanol}$) and "ethyl acetate selectivity" ($S_{ethyl\ acetate}$) were calculated from the composition of the reactor effluent as $$X_{ethanol} = 100\left(\frac{F_{EtOH,0} - F_{EtOH}}{F_{EtOH,0}}\right)$$

$$S_{ethyl\ acetate} = 100\left(\frac{2F_{EtOAc} + 2F_{AcH}}{F_{EtOH,0} - F_{EtOH}}\right)$$

where $F_{EtOH}$, $F_{EtOAc}$, and $F_{AcH}$ represent the molar flow rates of ethanol, ethyl acetate, and acetaldehyde in the reactor effluent, respectively, and $F_{EtOH,0}$ represents the molar flow rate of ethanol into the reactor inlet. Acetaldehyde is a reaction intermediate and so was included in the selectivity calculation. As used herein, the ethyl acetate selectivity of the conversion refers to the amount of ethanol that is consumed in the conversion reaction that is converted to ethyl acetate.

TABLE 3

Conversion and Selectivity for selected catalysts in a fixed bed reactor at 220° C. and 1 atm

| Catalyst sample | As prepared/received | | Reduced in $H_2$ | |
|---|---|---|---|---|
|  | X | S | X | S |
| Pellet catalysts |  |  |  |  |
| $CuO/ZnO/Al_2O_3$ | 18.9 | 92.4 | 35.0 | 89.7 |
| $CuO/Cr_2O_3/BaO$ | 43.5 | 89.4 | 36.0 | 74.6 |
| Impregnated catalysts |  |  |  |  |
| $CuO/SiO_2$ | 19.6 | 96.2 | 22.5 | 80.9 |
| $CuO/SiO_2$—$Al_2O_3$ | 43.0 | 17.0 |  |  |
| $CuO/Al_2O_3$ | 50.2 | 47.3 |  |  |
| $CuO/ZnO$ | 19.7 | 65.5 |  |  |
| $CuO/ZrO_2$ | 41.5 | 63.4 |  |  |
| $CuO/SiO_2$—$ZrO_2$ | 40.0 | 59.7 |  |  |
| $CuO/MgO/SiO_2$ | 37.9 | 70.0 | 32.1 | 65.7 |
| $CuO/CaO/SiO_2$ | 33.3 | 73.4 | 29.0 | 42.7 |
| $CuO/SrO/SiO_2$ | 25.1 | 77.2 | 31.5 | 69.6 |
| $CuO/BaO/SiO_2$ | 31.0 | 73.2 | 33.6 | 73.6 |
| $CuO/Na_2O/SiO_2$ | 19.4 | 95.9 |  |  |
| $CuO/ZrO_2/SiO_2$ | 39.1 | 58.7 | 54.0 | 61.6 |
| Co-precipitation catalysts |  |  |  |  |
| $CuO/ZnO/ZrO_2/Al_2O_3$ | 8.7 | 83.6 | 21.4 | 72.6 |
| $CuO/ZnO/ZrO_2/Al_2O_3/Na_2CO_3$ | 26.1 | 40.1 | 39.0 | 86.1 |
| $CuO/ZnO/ZrO_2/Cr_2O_3$ | 28.8 | 92.0 | 20.9 | 80.9 |
| $CuO/ZnO/ZrO_2/Cr_2O_3/Na_2CO_3$ | 37.0 | 90.2 | 35.9 | 87.5 |
| $CuO/ZnO/ZrO_2/Fe_2O_3$ | 34.1 | 92.1 | 17.0 | 94.2 |
| $CuO/ZnO/ZrO_2/Fe_2O_3/Na_2CO_3$ | 30.7 | 72.6 |  |  |
| $CuO/ZnO/ZrO_2/Al_2O_3/Cr_2O_3$ | 24.5 | 88.4 | 18.5 | 79.4 |
| $CuO/ZnO/ZrO_2/Al_2O_3/Cr_2O_3/Na_2CO_3$ | 33.2 | 86.3 |  |  |

Example 10

Conversion of Ethanol to n-Butanol Using a Ca-Pyrophosphate/Cu Catalyst

A catalyst was prepared by mixing 8 grams of $Ca_2P_2O_7$ with 0.2 g CuO as powders. The catalyst was treated with hydrogen at 220° C. The catalyst (8 grams catalyst) was placed in contact with ethanol at a flow rate of 0.04 ml/min at 260° C. in presence of 15.4 ml/min. co-fed hydrogen. The reaction was for carried out for 4 hours. The observed conversion was calculated to be about 15% and the resulting selectivities are listed in Table 4.

TABLE 4

Selectivities for example 10

| Compound | Selectivity, wt. % |
|---|---|
| Acetaldehyde | 27 |
| Acetone | 1.3 |
| 2-Propanol | 0.5 |
| Butyraldehyde | 5.2 |
| 2-Butanone | 1.1 |
| Ethyl Acetate | 0.7 |
| 2-Butanol | 0.5 |
| 1-Butanol | 49.2 |
| 2-Pentanone | 3.7 |
| Ethyl Butyrate | 2.1 |
| Butyl Acetate | 0.7 |
| 4-Hydroxy-2-butanone | 4.6 |
| 1,2-Butanediol | 2.5 |

Example 11

Conversion of Ethanol to n-Butanol Using a Nanoparticulate MgO/Cu Catalyst

A catalyst was prepared by mixing 8 grams of nanoparticulate Nanoactive® MgO (sourced from Nanoscale Materials Corp. of Manhattan, Kans.) with 0.2 grams CuO as powders. The catalyst was treated with hydrogen at 220° C. The catalyst (8 grams catalyst) was placed in contact with ethanol at a flow rate of 0.04 ml/min at 300° C. in the presence of 15.4 ml/min. co-fed hydrogen. The reaction was carried out for 4 hours. The observed conversion was calculated to be about 26% and the resulting selectivities are listed in Table 5.

TABLE 5

Selectivities for example 11

| Compound | Selectivity, wt. % |
|---|---|
| Acetaldehyde | 15.1 |
| Acetone | 2.1 |
| 2-Propanol | 2 |
| Butyraldehyde | 3.6 |
| 2-Butanone | 2.7 |
| Ethyl Acetate | 0.5 |
| 2-Butanol | 2.1 |
| 1-Butanol | 60.9 |
| 2-Pentanone | 8.9 |
| Ethyl Butyrate | 2.1 |
| Butyl Acetate | 0 |
| 4-Hydroxy-2-butanone | 0 |
| 1,2-Butanediol | 0 |

Example 12

Conversion of Ethanol to n-Butanol Using Synthetic Hydrotalcite/Cu Catalyst

A catalyst was prepared by mixing 8 grams of synthetic hydrotalcite with 0.2 grams CuO as powders. The catalyst was treated with hydrogen at 220° C. The catalyst (8 grams catalyst) was placed in contact with ethanol at a flow rate of 0.04 ml/min in the presence of 15.4 ml/min co-fed hydrogen. The reaction was carried out for 4 hours. The observed conversion was calculated to be about 2% and the resulting selectivities are listed in Table 6.

TABLE 6

Selectivities for example 12

| Compound | Selectivity, wt. % |
|---|---|
| Acetaldehyde | 71 |
| Acetone | 0 |
| 2-Propanol | 0 |
| Butyraldehyde | 0 |
| 2-Butanone | 0 |
| Ethyl Acetate | 2.1 |
| 2-Butanol | 0 |
| 1-Butanol | 26.9 |
| 2-Pentanone | 0 |
| Ethyl Butyrate | 0 |
| Butyl Acetate | 0 |
| 4-Hydroxy-2-butanone | 0 |
| 1,2-Butanediol | 0 |

Example 13

Conversion of Ethanol to n-Butanol Using a Mg(OH)$_2$/Cu Catalyst

A catalyst was prepared by mixing 9 grams of Mg(OH)$_2$ with 0.5 grams of CuO as powders. The catalyst was treated with hydrogen at 220° C. The catalyst (8 grams catalyst) was placed in contact with ethanol at a flow rate of 0.04 ml/min at 300° C. without a co-feed of hydrogen. The reaction was carried out for 4 hours. The observed conversion was calculated to be about 64% and the resulting selectivities are listed in Table 7.

TABLE 7

Selectivity for example 13

| Compound | Selectivity, wt. % |
|---|---|
| Acetaldehyde | 57.3 |
| Acetone | 2.4 |
| 2-Propanol | 0 |
| Butyraldehyde | 21.4 |
| 2-Butanone | 0.5 |
| Ethyl Acetate | 0.9 |
| 2-Butanol | 0 |
| 1-Butanol | 13.7 |
| 2-Pentanone | 2.5 |
| Ethyl Butyrate | 1.2 |
| Butyl Acetate | 0 |
| 4-Hydroxy-2-butanone | 0 |
| 1,2-Butanediol | 0 |

Example 14

Conversion of Ethanol to n-Butanol Using a Ca(OH)$_2$ Treated Synthetic Hydrotalcite/Cu Catalyst The catalyst was prepared by mixing 9 grams Ca-hydroxide treated synthetic hydrotalcite with 0.6 grams CuO as powders. The Ca-hydroxide treated hydrotalcite was prepared by mixing a slurry of 3 grams of Ca(OH)$_2$ in 30 ml of water with 20 grams of synthetic hydrotalcite. The mixture was then heated to dryness followed by heating to 300° C. for 2 hours. The catalyst was treated with hydrogen at 220° C.

The catalyst (8 grams catalyst) was placed in contact with ethanol at a flow rate of 0.04 ml/min at 300° C. without a co-feed of hydrogen. The reaction was carried out for 4 hours. The observed conversion was calculated to be about 58% and the resulting selectivities are listed in Table 8.

TABLE 8

Selectivity for example 14

| Compound | Selectivity, wt. % |
|---|---|
| Acetaldehyde | 45.6 |
| Acetone | 1.6 |
| 2-Propanol | 0 |
| Butyraldehyde | 27.2 |
| 2-Butanone | 0 |
| Ethyl Acetate | 1.7 |
| 2-Butanol | 0 |
| 1-Butanol | 21.2 |
| 2-Pentanone | 1.4 |
| Ethyl Butyrate | 0.8 |
| Butyl Acetate | 0 |
| 4-Hydroxy-2-butanone | 0 |
| 1,2-Butanediol | 0 |

Example 15

Conversion of Ethanol to n-Butanol Using a MgO (from Magnesium Basic Carbonate)/Cu Catalyst The catalyst was prepared by mixing 9 grams of MgO prepared from Mg basic carbonate (available from Fisher Scientific of Waltham, Mass.) with 1 gram of CuO as powders. The MgO was prepared by heating commercially available $MgCO_3 \cdot Mg(OH)_2$ to 450° C. at a heating rate of about 1° C./min. The mixture was held at 450° C. for 2 hours. The resulting catalyst was treated with hydrogen at 220° C.

The catalyst (8 grams catalyst) was placed in contact with ethanol at a flow rate of 0.04 ml/min at 260° C. without a co-feed of hydrogen. The reaction was carried out for 4 hours. The observed conversion was calculated to be about 52% and the resulting selectivities are listed in Table 9.

TABLE 9

Selectivity for example 15

| Compound | Selectivity, wt. % |
|---|---|
| Acetaldehyde | 38.3 |
| Acetone | 1.3 |
| 2-Propanol | 0 |
| Butyraldehyde | 21.2 |
| 2-Butanone | 0.5 |
| Ethyl Acetate | 2.8 |
| 2-Butanol | 0 |
| 1-Butanol | 31.8 |
| 2-Pentanone | 1.7 |
| Ethyl Butyrate | 2.1 |
| Butyl Acetate | 0 |
| 4-Hydroxy-2-butanone | 0 |
| 1,2-Butanediol | 0 |

Example 16

Conversion of Ethanol to n-Butanol Using a MgO (from Magnesium Hydroxide)/Cu Catalyst The catalyst was prepared by mixing 9 grams of MgO prepared from Mg hydroxide (available from Fisher scientific of Waltham, Mass.) with 1 gram of CuO as powders. The MgO was prepared by heating the $Mg(OH)_2$ in an open crucible to 450° C. at a heating rate of about 1° C./min. The $Mg(OH)_2$ was held at 450° C. for about 2 hours. The mixed MgO and CuO catalyst was treated with hydrogen at 220° C.

The catalyst (8 grams catalyst) was placed in contact with ethanol at a flow rate of 0.04 ml/min at 300° C. without a co-feed of hydrogen. The reaction was carried out for 4 hours. The observed conversion was calculated to be about 56% and the resulting selectivities are listed in Table 10.

TABLE 10

Selectivity for example 16

| Compound | Selectivity, wt. % |
|---|---|
| Acetaldehyde | 38.7 |
| Acetone | 1.1 |
| 2-Propanol | 0 |
| Butyraldehyde | 27.5 |
| 2-Butanone | 0.5 |
| Ethyl Acetate | 0.6 |
| 2-Butanol | 0 |
| 1-Butanol | 25.1 |
| 2-Pentanone | 2.1 |
| Ethyl Butyrate | 0.8 |
| Butyl Acetate | 0 |
| 4-Hydroxy-2-butanone | 2.3 |
| 1,2-Butanediol | 1.2 |

Example 17

Conversion of Ethanol to n-Butanol Using a MgO (from Magnesium Hydroxide)/Cu Catalyst Loaded Through a Cu-Salt Precursor The catalyst was prepared by gradually mixing 10 grams of MgO prepared from Mg hydroxide (available from Fisher scientific of Waltham, Mass.) with 1.5 grams of Cu-acetate hydrate as ethanol solution. Once all of the acetate salt was transferred and the ethanol was evaporated, the material was heated to 415° C. to generate the final catalyst. The MgO used in the mixture was prepared by heating $Mg(OH)_2$ in a crucible to 450° C. at a heating rate of about 1° C./min and holding the $Mg(OH)_2$ at 450° C. for 2 hours. The mixed catalyst was treated with hydrogen at 220° C.

The catalyst (8 grams catalyst) was placed in contact with ethanol at a flow rate of 0.04 ml/min at 260° C. without a co-feed of hydrogen. The reaction was carried out for 4 hours. The observed conversion was calculated to be about 55% and the resulting selectivities are listed in Table 11.

TABLE 11

Selectivity for example 17

| Compound | Selectivity, wt. % |
|---|---|
| Acetaldehyde | 53.3 |
| Acetone | 1.2 |
| 2-Propanol | 0 |
| Butyraldehyde | 23.9 |
| 2-Butanone | 0 |
| Ethyl Acetate | 1 |
| 2-Butanol | 0 |
| 1-Butanol | 17.4 |
| 2-Pentanone | 1.7 |
| Ethyl Butyrate | 0.9 |
| Butyl Acetate | 0 |
| 4-Hydroxy-2-butanone | 0 |
| 1,2-Butanediol | 0 |

Example 18

Direct Synthesis of Alcohols from Ethanol

Catalysts were tested for higher alcohol synthesis reactions in a fixed bed reactor operating at about 200-300° C. and about 1-35 atm. Catalysts were reduced in a stream of $H_2$ at a temperature between 175° C. and 240° C. prior to use in reactions.

Table 12 shows the reactor effluent composition using two different supported catalysts at different temperatures. The first catalyst was a mixture of CuO and MgO co-impregnated onto a $SiO_2$ support and the second was CuO, $ZrO_2$ and $Al_2O_3$ co-impregnated onto an $Al_2O_3$ support. The reactor effluent composition shown in Table 12 resulted from the use of 5.0 g catalyst with a 0.10 ml/min ethanol feed at 500 psig. As expected, increasing temperature also increased the conversion of ethanol to alcohols. Significant amounts of acetaldehyde and butyraldehyde were also observed, but no crotonaldehyde was observed in the reactor effluent. In Table 12, the "hexanols" include both 1-hexanol and 2-ethylbutanol, and the "octanols" include 1-octanol and 2-ethylhexanol.

TABLE 12

| Catalyst | Temperature (° C.) | Effluent Composition (wt %) | | | |
|---|---|---|---|---|---|
| | | Ethanol | 1-Butanol | Hexanols | Octanols |
| CuO/MgO on $SiO_2$ | 240 | 88.8 | 4.3 | 1.8 | 1.1 |
| | 260 | 85.4 | 6.3 | 1.9 | 0.8 |
| | 280 | 76.9 | 12.3 | 2.6 | 1.1 |
| | 300 | 68.4 | 14.8 | 4.2 | 1.2 |
| CuO/$ZrO_2$/$Al_2O_3$ on $Al_2O_3$ | 220 | 90.2 | 5.3 | 1.3 | 0.5 |
| | 240 | 84.6 | 8.2 | 2.2 | 0.8 |
| | 260 | 78.8 | 11.1 | 2.7 | 0.9 |
| | 280 | 56.3 | 19.9 | 7.0 | 2.2 |
| | 300 | 43.0 | 23.0 | 10.1 | 3.5 |

Figure 15:
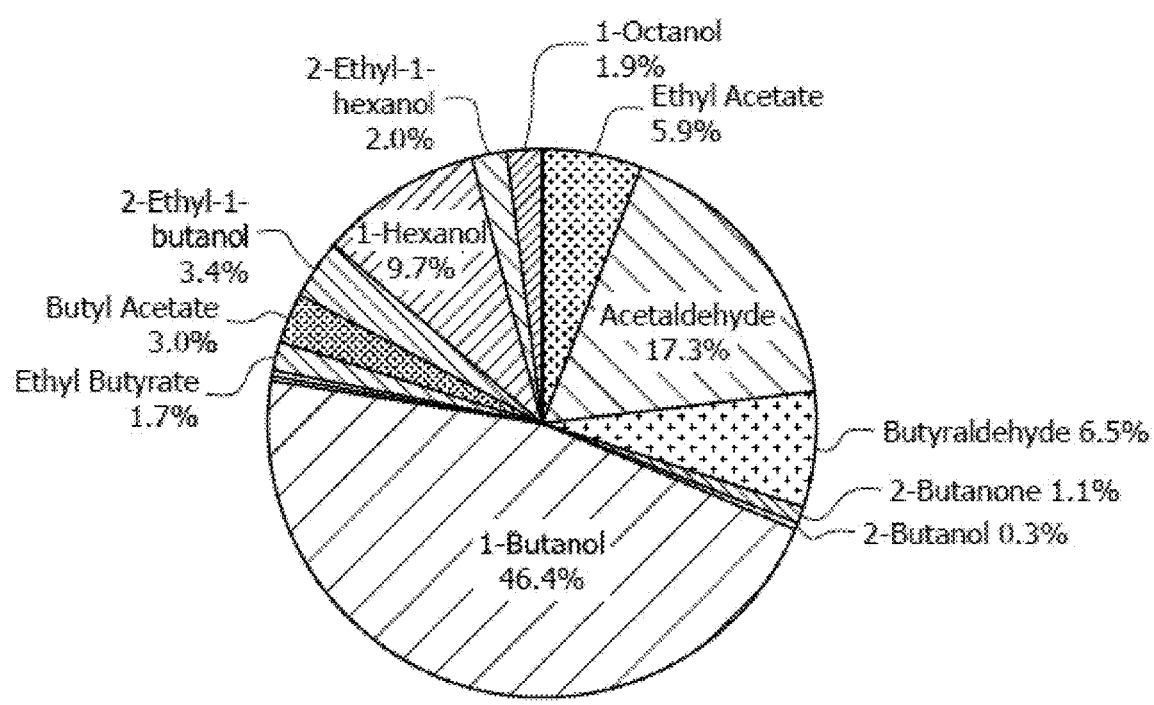
FIG. 15 illustrates another organic product distribution using yet another embodiment of a catalyst.
Figure 16:
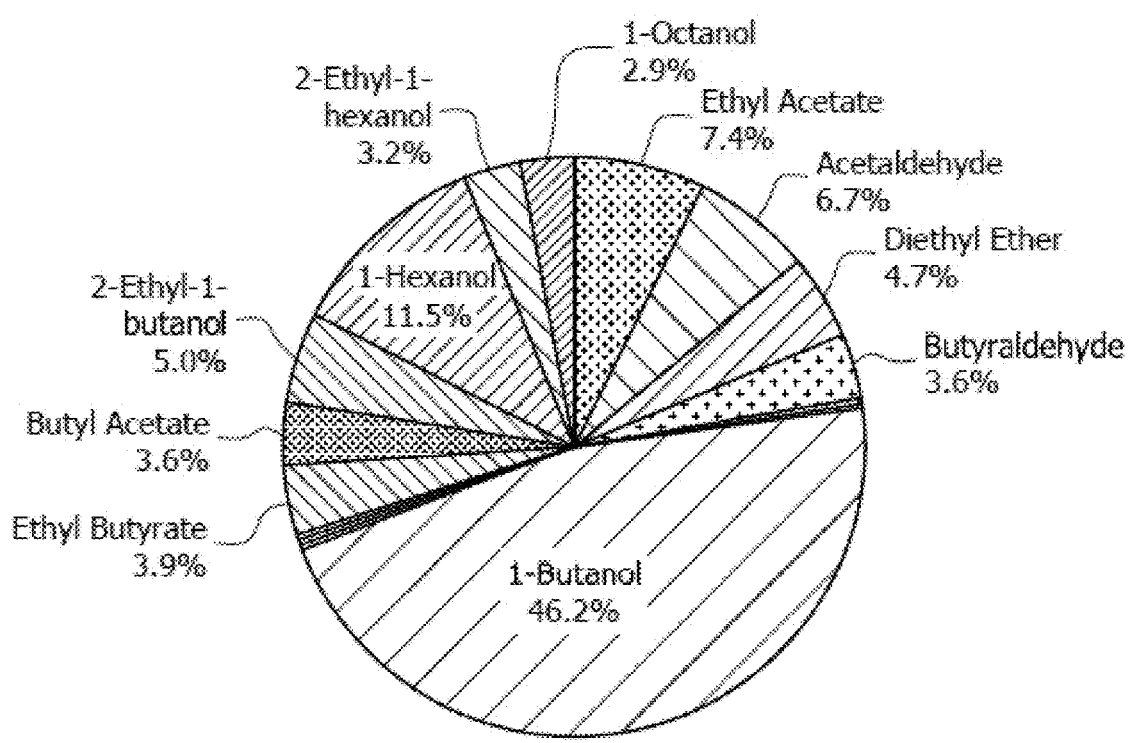
FIG. 16 illustrates still another organic product distribution using another embodiment of a catalyst.

FIG. 15 shows a typical product distribution from the CuO/MgO on $SiO_2$ catalyst with a 0.10 ml/min of ethanol feed at 300° C. and 500 psig. Including the intermediates acetaldehyde and butyraldehyde along with all of the product alcohols, the overall reaction selectivity is above 85% (the percent of the total ethanol consumed that is converted into the desired product or reaction intermediates). Other reaction products include mostly esters such as ethyl acetate, butyl acetate, and ethyl butyrate, although some 2-butanone and 2-butanol are also present in the reactor effluent. The product distribution using the CuO/$ZrO_2$/$Al_2O_3$ on $Al_2O_3$ catalyst with a 0.10 ml/min of ethanol feed at 280° C. and 500 psig is shown in FIG. 16, displays a similar breakdown of reaction byproducts, except a significant amount of diethyl ether is produced over this catalyst.

Example 19

Direct Synthesis of Alcohols from Ethanol

The catalyst was prepared by mixing 10.7 grams of $Mg(CH_3COO)_2 \cdot 4H_2O$ with 0.6 gram of $Al(OH)(OAc)_2$ and 0.6 g Cu-acetate hydrate. The solids were dissolved in ~150 ml de-ionized water with the addition of 10 ml glacial acetic acid. The solution was loaded on either 15 g Saint Gobain 61138 silica(A) or 15 g WR Grace 2720 alumina(B). The resulted loaded supports were heated to 350° C. at 1° C./min and held at 350° C. for 3 h. The resulting catalysts (5 grams each catalyst) were placed in contact with ethanol at a flow rate of 0.1 ml/min at 260° C. without a co-feed of hydrogen at a pressure of 500 psig. The reaction was carried out for 2 hours. The observed conversion for (A) was calculated to be about 30% and the resulting selectivity is listed in Table 13.

TABLE 13

| Compound | Selectivity, wt. % |
|---|---|
| Acetaldehyde | 10.4 |
| Acetone | 0 |
| 2-Propanol | 0 |
| Butyraldehyde | 3.7 |
| 2-Butanone | 1 |
| Ethyl Acetate | 6.8 |
| 2-Butanol | 0 |
| 1-Butanol | 51.9 |
| 2-Pentanone | 1.7 |
| Ethyl Butyrate | 2.8 |
| Butyl Acetate | 2.4 |

TABLE 13-continued

| Compound | Selectivity, wt. % |
|---|---|
| 2-ethyl-1-butanol | 5.5 |
| 1-hexanol | 10.7 |
| 2-ethyl-1-hexanol | 2.4 |
| 1-octanol | 1.3 |

When loaded on WR Grace alumina the observed conversion was 31% with observed product distribution selectivity listed in Table 14.

TABLE 14

| Compound | Selectivity, wt. % |
|---|---|
| Acetaldehyde | 7.7 |
| Acetone | 0 |
| 2-Propanol | 0 |
| Butyraldehyde | 3.5 |
| 2-Butanone | 0.5 |
| Ethyl Acetate | 9.7 |
| 2-Butanol | 0 |
| 1-Butanol | 55.5 |
| 2-Pentanone | 0 |
| Ethyl Butyrate | 3.6 |
| Butyl Acetate | 2.4 |

TABLE 14-continued

| Selectivity | |
|---|---|
| Compound | Selectivity, wt. % |
| 2-ethyl-1-butanol | 3.2 |
| 1-hexanol | 9.6 |
| 2-ethyl-1-hexanol | 1.7 |
| 1-octanol | 1.4 |

Example 20

Synthesis of Butyl Acetate

Experiments were conducted in order to simulate the lower sections of a reactive distillation column to demonstrate the feasibility of producing butyl acetate. The reactions were conducted in a batch reactor with 15 g of a co-precipitated $CuO/ZrO_2/Al_2O_3$ catalyst and ~70 ml of a 10.5 wt % ethanol 89.5 wt % ethyl acetate mix. The catalyst was reduced at 220° C. in $H_2$ overnight, before the ethanol/ethyl acetate mixture was added to the reactor. The reactor was then heated to the desired reaction temperature and held for 24 hrs. After 24 hrs a liquid sample was collected from the reactor. The composition of the final reaction mixture after 24 hrs is shown in Table 15.

TABLE 15

Final compositions after 24 hrs at reaction temperatures in batch reactions simulating lower sections of RD column

| Reaction Temperature (° C.) | Final reaction mixture composition wt % | | | |
|---|---|---|---|---|
| | Ethyl acetate | butyl acetate | 1-butanol | ethanol |
| 200 | 93.0 | 0.44 | 0.04 | 5.8 |
| 220 | 93.7 | 1.3 | 0.05 | 3.8 |
| 240 | 94.5 | 2.4 | 0.04 | 1.7 |

Table 15 demonstrates that at elevated temperatures a significant portion of the ethanol in the feed is consumed to make butyl acetate. It also shows that the intermediate in this reaction, 1-butanol, is nearly quantitatively consumed to make the butyl acetate.

Example 21

Simulation of a Butyl Acetate Production Process

A process simulator was used to model the production of butyl acetate in a reactive distillation column as described herein. In this example, an Aspen Plus simulation of a process for producing butyl acetate from ethanol using a reactive distillation was performed. The feed comprised ethanol (99.5 mol % ethanol) and water. The major constraints for the process were on the selectivity of the final product. The column configuration used in the simulation showed that 100% conversion and above 99% selectivity towards butyl acetate can be achieved.

The following reactions were modeled for the production of butyl acetate from ethanol:

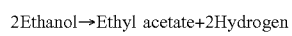

2Ethanol→Ethyl acetate+2Hydrogen

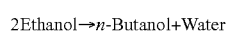

2Ethanol→n-Butanol+Water

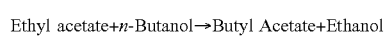

Ethyl acetate+n-Butanol→Butyl Acetate+Ethanol

Figure 17:
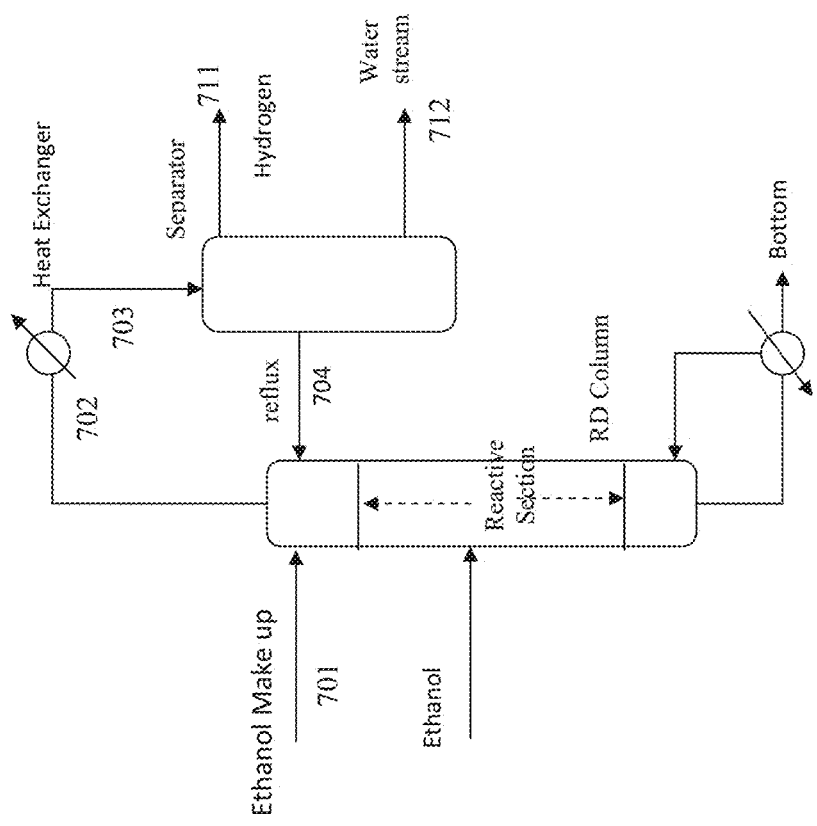
FIG. 17 illustrates a schematic view of a simulated reactive distillation system according to an embodiment.

A power law kinetic model was used for the reaction scheme. The process was simulated using Aspen plus as a simulation tool, and the simulated process consists of reactive distillation (RD) column, heat exchanger and component separator for the production of butyl acetate from ethanol as shown in FIG. 17. The simulated reactive distillation column was operated at 40 bar and had total 26 stages, out of which 15 stages were modeled as being reactive (between stage 8 to 22). The feed was modeled as being on stage 7. Here, the reboiler is mentioned as stage 1. The total catalyst loading was 12,200 liters with a feed stream of ethanol of 175,000 kg/day.

In the modeled system, the vapor stream 702 comes from the top of the reactive distillation column and condensed in the heat exchanger. The condensed liquid and non-condensed vapor (hydrogen) stream 703 is sent to the component separator, where hydrogen (gas) in stream 711, water in stream 712, and other organic liquid in stream 704 get separated. The organic liquid stream 704 was sent back to the column as reflux. Stream 701 (0.001 kmol/hr), ethanol makeup at the top stage of the column, is provided to the simulator to help in converging the simulation, this stream has a negligible flow rate. The model simulation results for several streams are shown in Table 16.

TABLE 16

| | Mole Flow (kmol/hr) | | | |
|---|---|---|---|---|
| | 11 Hydrogen Out Vapor | 12 Water Out Liquid | BOTTOM Liquid | INPUT Liquid |
| Ethanol | 0 | 0 | 0 | 157.97 |
| Ethyl Acetate | 0 | 0 | 0.42 | 0 |
| Hydrogen | 105.59 | 0 | 0 | 0 |
| Water | 0 | 51.7 | 1.47 | 0.79 |
| 1-Butanol | 0 | 0 | 0 | 0 |
| Butyl Acetate | 0 | 0 | 52.4 | 0 |

The Aspen Plus simulation results confirm the feasibility of using a reactive distillation process for the production of butyl acetate from ethanol. High purity butyl acetate can be obtained as the bottoms stream and a close to complete conversion of ethanol may be possible.

Example 22

Synthesis of Butyl Acetate from Ethanol

Figure 18:
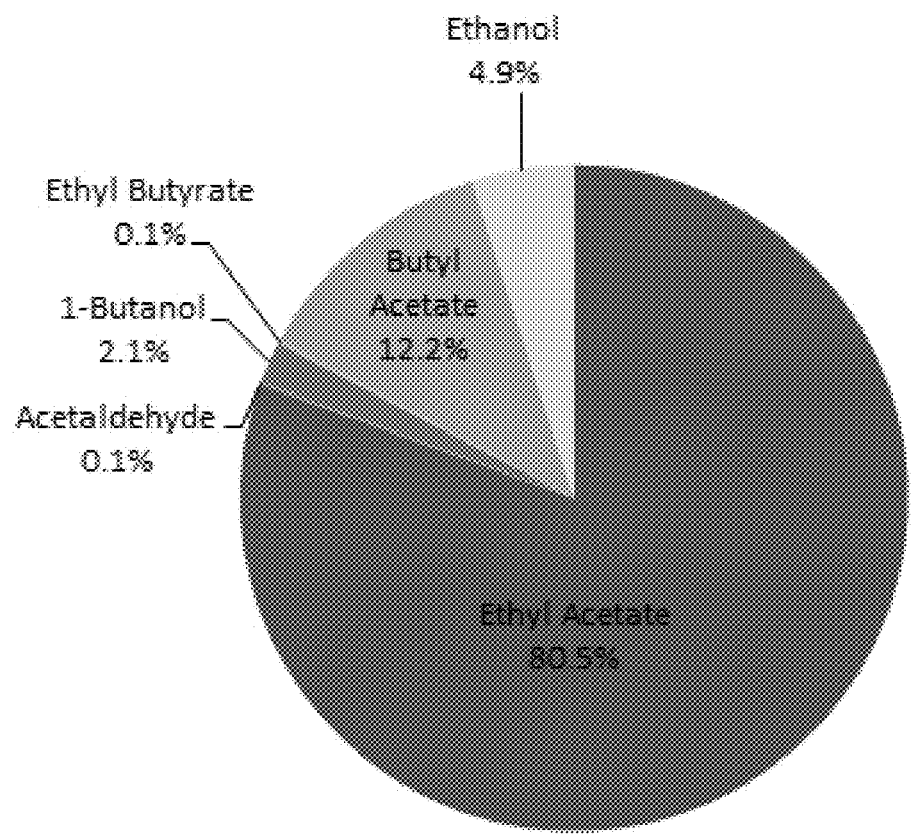
FIG. 18 illustrates another organic product distribution from a reactor using an embodiment of a catalyst.

A reaction was conducted to demonstrate the use of the same catalyst in both the ethanol dehydrogenation reactor to make ethyl acetate and the trans-esterification reactor to make butyl acetate. The suitability of the ethanol dehydrogenation catalyst was demonstrated by using a plug flow reactor operating at 35 atm and 200° C. with a feed of 9.7 wt % 1-butanol and 90.3 wt % ethyl acetate at 0.16 ml/min. 11.0 g of $CuO/ZrO_2/Al_2O_3$ was loaded into the fixed bed reactor and reduced overnight at 200° C. in flowing $H_2$ prior to starting the feed. The composition of the liquid effluent collected is shown in FIG. 18. As shown, the 1-butanol and ethyl acetate reacted selectively to give butyl acetate and ethanol.

Having described numerous systems and methods herein, various embodiments of can include, but are not limited to:

In a first embodiment, a reactive distillation method comprises introducing a feed stream to a reactive distillation column, wherein the feed stream comprises ethanol; contacting the feed stream with one or more catalysts in the reactive distillation column during a distillation, wherein the feed stream reacts in the presence of the one or more catalysts to produce a reaction product comprising ethyl acetate, butanol, and water, wherein the butanol and the ethyl acetate react to produce a reaction product comprising butyl acetate; and removing butyl acetate during the distillation from the reactive distillation column as a bottoms stream.

A second embodiment includes the method of the first embodiment, further comprising removing ethyl acetate, butanol, or both during the distillation from the reactive distillation column in the bottoms stream.

A third embodiment includes the method of the second embodiment, further comprising increasing a ratio of the amount of the butyl acetate to the ethyl acetate, butanol, or both in the bottoms stream by increasing the pressure in the reactive distillation column.

A fourth embodiment includes the method of the second embodiment, further comprising increasing a ratio of the amount of the butyl acetate to the ethyl acetate, butanol, or both in the bottoms stream by providing a non-reactive packing in a lower portion of the reactive distillation column.

A fifth embodiment includes the method of the first embodiment, further comprising: contacting the bottoms stream with a hydrogenation catalyst and hydrogen to hydrogenate at least a portion of a contaminant in the bottoms stream, and separating the hydrogenated portion of the contaminant from the bottoms stream.

A sixth embodiment includes the method of the fifth embodiment, wherein the hydrogenation catalyst comprises a Group VIII metal, a Group VI metal, or any combination thereof.

A seventh embodiment includes the method of any of the first to sixth embodiments, wherein the catalyst comprises a Guerbet reaction catalyst, a solid base multicomponent oxide catalyst, a solid acid/base bifunctional catalyst, a zeolite with alkali counterions, a magnesium oxide catalyst, an oxide powder catalyst, or any combination thereof.

An eighth embodiment includes the method of any of the first to seventh embodiments, wherein the catalyst comprises a hydroxyapatite Guerbet reaction catalyst, a solid base Guerbet reaction catalyst, or a combination thereof.

A ninth embodiment includes the method of any of the first to eighth embodiments, wherein the catalyst comprises a catalyst component represented by the formula:

$M/MgO/Al_2O_3$, where M represents palladium, rhodium, nickel, or copper, or oxides thereof.

A tenth embodiment includes the method of any of the first to ninth embodiments, wherein the catalyst comprises a hydroxyapatite represented by the formula:

$Ca_{10}(PO_4)_6(OH)_2$ where the ratio of calcium to phosphorus (Ca:P) is between about 1.5 and about 1.8.

An eleventh embodiment includes the method of any of the first to tenth embodiments, wherein the catalyst comprises an apatite structure satisfying the formula:

$M_a(M'O_b)_cX_2$, where M represents calcium, strontium, magnesium, barium, lead, cadmium, iron, cobalt, nickel, zinc, or hydrogen, wherein M' represents phosphorus, vanadium, arsenic, carbon, or sulfur, wherein X represents a fluorine, chlorine, bromine, or a hydroxide, and where a is about 10, b is about 3, c is about 6, and the ratio of a to c is between about 1.5 and about 1.8.

A twelfth embodiment includes the method of any of the first to eleventh embodiments, wherein the catalyst comprises a calcium phosphate, a calcium phosphate carbonate, a calcium pyrophosphate, a magnesium phosphate, a magnesium phosphate carbonate, a magnesium pyrophosphate or any combination thereof.

A thirteenth embodiment includes the method of any of the first to twelfth embodiments, wherein the catalyst comprises magnesium oxide, magnesium hydroxide, magnesium phosphate hydrate ($Mg_3(PO_4)_2.8H_2O$), calcium oxide, calcium hydroxide, calcium fluoride, calcium silicate (wollastonite), calcium sulfate dihydrate (gypsum), lithium phosphate, aluminum phosphate, titanium dioxide, fluorapatite ($Ca_{10}(PO_4)_6F_2$), tetracalcium phosphate ($Ca_4(PO_4)_2O$), hydrotalcite, talc, kaolin, sepiolite, or any combination thereof.

A fourteenth embodiment includes the method of any of the first to thirteenth embodiments, wherein the catalyst comprises at least one catalytic component selected from the group consisting of: copper, copper oxide, barium, barium oxide, ruthenium, ruthenium oxide, rhodium, rhodium oxide, platinum, platinum oxide, palladium, palladium oxide, rhenium, rhenium oxide, silver, silver oxide, cadmium, cadmium oxide, zinc, zinc oxide, zirconium, zirconium oxide, gold, gold oxide, thallium, thallium oxide, magnesium, magnesium oxide, manganese, manganese oxide, aluminum, aluminum oxide, chromium, chromium oxide, nickel, nickel oxide, iron, iron oxide, molybdenum, molybdenum oxide, sodium, sodium oxide, sodium carbonate, strontium, strontium oxide, tin, tin oxide, and any mixture thereof.

A fifteenth embodiment includes the method of any of the first to fourteenth embodiments, wherein the catalyst comprises a multi-component catalyst.

A sixteenth embodiment includes the method of the fifteenth embodiment, wherein the multi-component catalyst comprises a first catalyst component and a second catalyst component, wherein the first catalyst component is configured to convert at a portion of the ethanol in the feed stream to the ethyl acetate, and wherein the second catalyst component is configured to convert at least a portion of the ethanol in the feed stream into the butanol and water.

A seventeenth embodiment includes the method of any of the first to sixteenth embodiments, further comprising: removing a side stream from the reactive distillation column; contacting the side stream with a side reactor catalyst, wherein the side stream reacts in the presence of the side reactor catalyst to produce butyl acetate; and reintroducing the butyl acetate produced in the presence of the side reactor catalyst to the reactive distillation column.

An eighteenth embodiment includes the method of any of the first to seventeenth embodiments, further comprising: removing a side stream from the reactive distillation column; contacting the side stream with a side reactor catalyst, wherein the side stream reacts in the presence of the side reactor catalyst to produce at least one of ethyl acetate or butanol; and reintroducing the at least one of ethyl acetate or butanol produced in the presence of the side reactor catalyst to the reactive distillation column.

A nineteenth embodiment includes the method of any of the first to seventeenth embodiments, further comprising: removing a plurality of side streams from the reactive distillation column; introducing each of the plurality of side streams into a corresponding plurality of side reactors, wherein each side reactor of the plurality of side reactors comprise a side reactor catalyst; contacting each respective side stream with a side reactor catalyst in the corresponding side reactor, wherein each respective side stream reacts in the presence of the side reactor catalyst to produce at least one of ethyl acetate, butanol, or butyl acetate; and reintroducing the at least one of ethyl acetate, butanol, or butyl acetate produced in each side to the reactive distillation column.

A twentieth embodiment includes the method of any of the first to nineteenth embodiments, further comprising introducing a second feed stream comprising hydrogen to the reactive distillation column.

In a twenty first embodiment, a reactive distillation method comprises introducing a feed stream to a reactive distillation column, wherein the feed stream comprises ethanol; contacting the feed stream with one or more catalysts during a distillation, wherein the feed stream reacts in the presence of the one or more catalysts; producing a reaction product comprising butyl acetate based on the contacting; and removing butyl acetate during the distillation from the reactive distillation column as a bottoms stream.

A twenty second embodiment includes the method of the twenty first embodiment, wherein the one or more catalysts are disposed in the reactive distillation column.

A twenty third embodiment includes the method of the twenty first embodiment, wherein the one or more catalysts are disposed in a side reactor in fluid communication with the reactive distillation column.

A twenty fourth embodiment includes the method of the twenty third embodiment, further comprising: removing a side stream from the reactive distillation column; contacting the side stream with the one or more catalysts in the side reactor, wherein the side stream reacts in the presence of the one or more catalysts to produce butyl acetate; and reintroducing the butyl acetate produced in the presence of the one or more catalysts to the reactive distillation column.

A twenty fifth embodiment includes the method of the twenty third embodiment, further comprising: removing a side stream from the reactive distillation column; contacting the side stream with the one or more catalysts in the side reactor, wherein the side stream reacts in the presence of the one or more catalysts to produce at least one of ethyl acetate or butanol; and reintroducing the at least one of ethyl acetate or butanol produced in the presence of the one or more catalysts to the reactive distillation column.

A twenty sixth embodiment includes the method of the twenty first embodiment, further comprising: removing a plurality of side streams from the reactive distillation column; introducing each of the plurality of side streams into a corresponding plurality of side reactors, wherein each side reactor of the plurality of side reactors comprise a catalyst of the one or more catalysts; contacting each respective side stream with the catalyst in the corresponding side reactor, wherein each respective side stream reacts in the presence of the catalyst to produce at least one of ethyl acetate, butanol, or butyl acetate; and reintroducing the at least one of ethyl acetate, butanol, or butyl acetate produced in each side to the reactive distillation column.

A twenty seventh embodiment includes the method of any of the twenty first to twenty sixth embodiments, further comprising: removing the bottoms stream from the reactive distillation column, wherein the bottoms stream comprises the butyl acetate and ethyl acetate; separating at least a portion of the ethyl acetate from the butyl acetate; and recycling the ethyl acetate to the reactive distillation column.

A twenty eighth embodiment includes the method of any of the twenty first to twenty seventh embodiments, further comprising: adjusting a pressure of the reactive distillation column to increase butyl acetate production.

A twenty ninth embodiment includes the method of any of the twenty first to twenty eighth embodiments, further comprising: producing butanol and ethyl acetate based on the contacting of the feed stream with the one or more catalysts during the distillation; contacting the butanol and the ethyl acetate with the one or more catalysts; and producing the butyl acetate based on the contacting of the butanol and the ethyl acetate with the one or more catalysts.

In a thirtieth embodiment, a reactive distillation system comprises a feed stream comprising ethanol; a reactive distillation column, wherein the reactive distillation column comprises: one or more catalysts disposed within the reactive distillation column, an ethanol feed configured to pass the feed stream comprising ethanol over at least a portion of the one or more catalysts to produce ethyl acetate and butanol, wherein the one or more catalysts are configured to cause ethyl acetate and butanol to react in the presence of the one or more catalysts to produce butyl acetate; an overhead product hydrogen removal passage, and a bottoms product butyl acetate removal passage.

A thirty first embodiment includes the system of the thirtieth embodiment, further comprising: a side reactor in fluid communication with the reactive distillation column, wherein the side reactor comprises a second catalyst; an inlet in fluid communication with the side reactor and the reactive distillation column, and configured to pass a fluid from the reactive distillation column over the second catalyst, and an outlet in fluid communication with the side reactor and the reactive distillation column, and configured to pass the fluid from the outlet of the side reactor to the reactive distillation column.

A thirty second embodiment includes the system of the thirty first embodiment, wherein the inlet is coupled to the reactive distillation column below the outlet.

A thirty third embodiment includes the system of the thirty second embodiment, wherein the fluid is a vapor.

A thirty fourth embodiment includes the system of the thirty first embodiment, wherein the inlet is coupled to the reactive distillation column above the outlet.

A thirty fifth embodiment includes the system of the thirty first embodiment, wherein the fluid is a liquid.

A thirty sixth embodiment includes the system of the thirty first embodiment, further comprising: a second side reactor in fluid communication with the reactive distillation column, wherein the second side reactor comprises a third catalyst; a second inlet in fluid communication with the second side reactor and the reactive distillation column, and configured to pass a second fluid from the reactive distillation column over the third catalyst, and a second outlet in fluid communication with the second side reactor and the reactive distillation column, and configured to pass the second fluid from the second outlet of the second side reactor to the reactive distillation column.

A thirty seventh embodiment includes the system of any of the thirtieth to thirty sixth embodiments, wherein the distillation column further comprises a hydrogenation catalyst disposed within the reactive distillation column; and wherein the reactive distillation system further comprises: a hydrogen feed in fluid communication with the reactive distillation column and configured to pass hydrogen over at least a portion of the hydrogenation catalyst.

In a thirty eight embodiment, a reactive distillation method comprises: contacting a first feed stream comprising ethanol with a first catalysts; producing ethyl acetate in a first product stream in response to contacting the first feed stream with the first catalyst; separating at least a portion of the ethyl acetate from the first product stream; contacting a second feed stream comprising ethanol with a second catalysts; producing butanol in a second product stream in response to contacting the second feed stream with the second catalyst; separating at least a portion of the butanol from the second product stream; introducing the portion of the ethyl acetate and the portion of the butanol into a reactive distillation column as one or more feed streams; contacting the ethyl acetate and butanol within the reactive distillation column; producing a reaction product comprising butyl acetate based on the contacting; and removing butyl acetate during the distillation from the reactive distillation column as a bottoms stream.

A thirty ninth embodiment includes the method of the thirty eighth embodiment, wherein contacting the ethyl acetate and butanol within the reactive distillation column occurs in the presence of one or more catalysts.

A fortieth embodiment includes the method of the thirty eighth or thirty ninth embodiment, wherein the one or more catalysts are disposed in one or more side reactors.

A forty first embodiment includes the method of any of the thirty eighth to fortieth embodiments, wherein contacting the first feed stream with the first catalyst occurs within a first reactive distillation column.

A forty second embodiment includes the method of any of the thirty eighth to forty first embodiments, wherein contacting the second feed stream with the second catalyst occurs within a second reactive distillation column.

In the preceding discussion and in the claims, the terms "including" and "comprising" are used in an open-ended fashion, and thus should be interpreted to mean "including, but not limited to . . . ". At least one embodiment is disclosed and variations, combinations, and/or modifications of the embodiment(s) and/or features of the embodiment(s) made by a person having ordinary skill in the art are within the scope of the disclosure. Alternative embodiments that result from combining, integrating, and/or omitting features of the embodiment(s) are also within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, $R_l$, and an upper limit, $R_u$, is disclosed, any number falling within the range is specifically disclosed. In particular, the following numbers within the range are specifically disclosed: $R=R_l+k*(R_u-R_l)$, wherein k is a variable ranging from 1 percent to 100 percent with a 1 percent increment, i.e., k is 1 percent, 2 percent, 3 percent, 4 percent, 5 percent, . . . , 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim means that the element is required, or alternatively, the element is not required, both alternatives being within the scope of the claim. Use of broader terms such as comprises, includes, and having should be understood to provide support for narrower terms such as consisting of, consisting essentially of, and comprised substantially of.

Accordingly, the scope of protection is not limited by the description set out above but is only limited by the claims which follow, that scope including all equivalents of the subject matter of the claims. Each and every claim is incorporated into the specification as an embodiment of the present disclosure. Thus, the claims are a further description and are an addition to the embodiments of the present disclosure. The discussion of a reference herein is not an admission that it is prior art to the present disclosure, especially any reference that may have a publication date after the priority date of this application. The disclosures of all patents, patent applications, and publications cited herein are hereby incorporated by reference, to the extent that they provide exemplary, procedural, or other details supplementary to those set forth herein.

What is claimed is:

1. A reactive distillation method comprising:
introducing a feed stream to a reactive distillation column, wherein the feed stream comprises ethanol;
contacting the feed stream with one or more catalysts during a distillation, wherein the one or more catalyst are capable of carrying out a dehydration reaction, a dehydrogenation reaction, and aldol condensation reaction, a transesterification reaction, or a combination thereof, wherein the feed stream reacts in the presence of the one or more catalysts to produce a reaction product comprising ethyl acetate, butanol, and water, wherein the butanol and the ethyl acetate react to produce a reaction product comprising butyl acetate; and
removing butyl acetate during the distillation from the reactive distillation column as a bottoms stream.

2. The method of claim 1, further comprising removing ethyl acetate, butanol, or both during the distillation from the reactive distillation column in the bottoms stream.

3. The method of claim 2, further comprising increasing a ratio of the amount of the butyl acetate to the ethyl acetate, butanol, or both in the bottoms stream by increasing the pressure in the reactive distillation column.

4. The method of claim 2, further comprising increasing a ratio of the amount of the butyl acetate to the ethyl acetate, butanol, or both in the bottoms stream by providing a non-reactive packing in a lower portion of the reactive distillation column.

5. The method of claim 1, further comprising:
contacting the bottoms stream with a hydrogenation catalyst and hydrogen to hydrogenate at least a portion of a contaminant in the bottoms stream; and
separating the hydrogenated portion of the contaminant from the bottoms stream.

6. The method of claim 5, wherein the hydrogenation catalyst comprises a Group VIII metal, a Group VI metal, or any combination thereof.

7. The method of claim 1, wherein the catalyst comprises a Guerbet reaction catalyst, a solid base multicomponent oxide catalyst, a solid acid/base bifunctional catalyst, a zeolite with alkali counterions, a magnesium oxide catalyst, an oxide powder catalyst, or any combination thereof.

8. The method of claim 1, wherein the catalyst comprises a hydroxyapatite Guerbet reaction catalyst, a solid base Guerbet reaction catalyst, or a combination thereof.

9. The method of claim 1, wherein the catalyst comprises a catalyst component of the formula:

M/MgO/Al$_2$O$_3$, wherein M is palladium, rhodium, nickel, or copper, or oxides thereof.

10. The method of claim 1, wherein the catalyst comprises a hydroxyapatite of the formula:

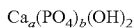
Ca$_a$(PO$_4$)$_b$(OH)$_2$ wherein a is about 10, wherein b is about 6, and wherein the ratio of a to b (a:b) is between about 1.5 and about 1.8.

11. The method of claim 1, wherein the catalyst comprises an apatite structure of the formula:

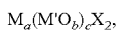
M$_a$(M'O$_b$)$_c$X$_2$, wherein M is calcium, strontium, magnesium, barium, lead, cadmium, iron, cobalt, nickel, zinc, or hydrogen, wherein M' represents phosphorus, vanadium, arsenic, carbon, or sulfur, wherein X is a fluorine, chlorine, bromine, or a hydroxide, and wherein a is about 10, b is about 3, c is about 6, and the ratio of a to c is between about 1.5 and about 1.8.

12. The method of claim 1, wherein the catalyst comprises a calcium phosphate, a calcium phosphate carbonate, a calcium pyrophosphate, a magnesium phosphate, a magnesium phosphate carbonate, a magnesium pyrophosphate or any combination thereof.

13. The method of claim 1, wherein the catalyst comprises magnesium oxide, magnesium hydroxide, magnesium phosphate hydrate (Mg$_3$(PO$_4$)$_2$.8H$_2$O), calcium oxide, calcium hydroxide, calcium fluoride, calcium silicate (wollastonite), calcium sulfate dihydrate (gypsum), lithium phosphate, aluminum phosphate, titanium dioxide, fluorapatite (Ca$_{10}$(PO$_4$)$_6$F$_2$), tetracalcium phosphate (Ca$_4$(PO$_4$)$_2$O), hydrotalcite, talc, kaolin, sepiolite, or any combination thereof.

14. The method of claim 1, wherein the catalyst comprises at least one catalytic component selected from the group consisting of: copper, copper oxide, barium, barium oxide, ruthenium, ruthenium oxide, rhodium, rhodium oxide, platinum, platinum oxide, palladium, palladium oxide, rhenium, rhenium oxide, silver, silver oxide, cadmium, cadmium oxide, zinc, zinc oxide, zirconium, zirconium oxide, gold, gold oxide, thallium, thallium oxide, magnesium, magnesium oxide, manganese, manganese oxide, aluminum, aluminum oxide, chromium, chromium oxide, nickel, nickel oxide, iron, iron oxide, molybdenum, molybdenum oxide, sodium, sodium oxide, sodium carbonate, strontium, strontium oxide, tin, tin oxide, and any mixture thereof.

15. The method of claim 1, wherein the catalyst comprises a multi-component catalyst.

16. The method of claim 15, wherein the multi-component catalyst comprises a first catalyst component and a second catalyst component, wherein the first catalyst component is configured to convert at a portion of the ethanol in the feed stream to the ethyl acetate, and wherein the second catalyst component is configured to convert at least a portion of the ethanol in the feed stream into the butanol and water.

17. The method of claim 1, further comprising:
removing a side stream from the reactive distillation column;
contacting the side stream with the catalyst in at least one side reactor, wherein the side stream reacts in the presence of the catalyst to produce butyl acetate; and
reintroducing the butyl acetate produced in the presence of the catalyst to the reactive distillation column.

18. The method of claim 1, further comprising:
removing a side stream from the reactive distillation column;
contacting the side stream with a side reactor catalyst, wherein the side stream reacts in the presence of the side reactor catalyst to produce at least one of ethyl acetate or butanol; and
reintroducing the at least one of ethyl acetate or butanol produced in the presence of the side reactor catalyst to the reactive distillation column.

19. The method of claim 1, further comprising:
removing a plurality of side streams from the reactive distillation column;
introducing each of the plurality of side streams into a corresponding plurality of side reactors, wherein each side reactor of the plurality of side reactors comprise at least one of the one or more catalysts;
contacting each respective side stream with the at least one of the one or more catalysts in the corresponding side reactor, wherein each respective side stream reacts in the presence of the at least one of the one or more catalysts to produce at least one of ethyl acetate, butanol, or butyl acetate; and
reintroducing the at least one of ethyl acetate, butanol, or butyl acetate produced in each side reactor to the reactive distillation column.

20. The method of claim 1, further comprising introducing a second feed stream comprising hydrogen to the reactive distillation column.

21. The method of claim 1, wherein the one or more catalysts are disposed in the reactive distillation column.

22. The method of claim 1, wherein the one or more catalysts are disposed in a side reactor in fluid communication with the reactive distillation column.

23. A reactive distillation system comprising:
a feed stream comprising ethanol;
a reactive distillation column, wherein the reactive distillation column comprises:
one or more catalysts disposed within the reactive distillation column, wherein the one or more catalysts are capable of carrying out a dehydration reaction, a dehydrogenation reaction, an aldol condensation reaction, a transesterification reaction, or a combination thereof,
an ethanol feed configured to pass the feed stream comprising ethanol over at least a portion of the one or more catalysts to produce ethyl acetate and butanol, wherein the one or more catalysts are configured to cause ethyl acetate and butanol to react in the presence of the one or more catalysts to produce butyl acetate;
an overhead product hydrogen removal passage, and
a bottoms product butyl acetate removal passage.

24. The system of claim 23, further comprising:
a side reactor in fluid communication with the reactive distillation column, wherein the side reactor comprises a second catalyst;
an inlet in fluid communication with the side reactor and the reactive distillation column, and configured to pass a fluid from the reactive distillation column over the second catalyst, and
an outlet in fluid communication with the side reactor and the reactive distillation column, and configured to pass the fluid from the outlet of the side reactor to the reactive distillation column.

25. The system of claim 24, wherein the inlet is coupled to the reactive distillation column below the outlet.

26. The system of claim 25, wherein the fluid is a vapor.

27. The system of claim 24, wherein the inlet is coupled to the reactive distillation column above the outlet.

28. The system of claim 24, wherein the fluid is a liquid.

29. The system of claim 24, further comprising:
a second side reactor in fluid communication with the reactive distillation column, wherein the second side reactor comprises a third catalyst;
a second inlet in fluid communication with the second side reactor and the reactive distillation column, and configured to pass a second fluid from the reactive distillation column over the third catalyst, and
a second outlet in fluid communication with the second side reactor and the reactive distillation column, and configured to pass the second fluid from the second outlet of the second side reactor to the reactive distillation column.

30. The system of claim 23, wherein the distillation column further comprises a hydrogenation catalyst disposed within the reactive distillation column; and wherein the reactive distillation system further comprises:
a hydrogen feed in fluid communication with the reactive distillation column and configured to pass hydrogen over at least a portion of the hydrogenation catalyst.

* * * * *